United States Patent
Lee et al.

(10) Patent No.: US 6,777,422 B2
(45) Date of Patent: Aug. 17, 2004

(54) SUBSTITUTED TETRAHYDROISOQUINOLINES AS C5A RECEPTOR MODULATORS

(75) Inventors: Kyungae Lee, Guilford, CT (US); Scott Mitchell, East Haven, CT (US); Robert Ohliger, Madison, CT (US); Lu Yan Zhang, Branford, CT (US); He Zhao, Branford, CT (US); Kevin Currie, North Branford, CT (US)

(73) Assignee: Neurogen Corp., Branford, CT (US)

( * ) Notice: Subject to any disclaimer, the term of this patent is extended or adjusted under 35 U.S.C. 154(b) by 0 days.

(21) Appl. No.: 10/401,135

(22) Filed: Mar. 27, 2003

(65) Prior Publication Data

US 2004/0006069 A1 Jan. 8, 2004

Related U.S. Application Data

(60) Provisional application No. 60/368,199, filed on Mar. 28, 2002.

(51) Int. Cl.[7] .................... C07D 217/00; A61K 31/47
(52) U.S. Cl. .................... 514/278; 546/15; 546/144; 546/146; 514/307
(58) Field of Search .................... 546/15, 144, 146; 514/278, 307

(56) References Cited

FOREIGN PATENT DOCUMENTS

| EP | 1308438 A1 | 5/2003 |
|---|---|---|
| EP | 1318140 A1 | 6/2003 |
| WO | WO 02/49993 | 6/2002 |

*Primary Examiner*—Zinna Northington Davis
(74) *Attorney, Agent, or Firm*—Ann T. Kaklecek; Seth A. Fidel

(57) ABSTRACT

Substituted tetrahydroisoquinolines and related compounds are provided. Such compounds are ligands that may be used to modulate C5a receptor activity in vivo or in vitro, and are particularly useful in the treatment of conditions associated with pathological C5a receptor activation in humans, domesticated companion animals and livestock animals. Pharmaceutical compositions and methods for using them to treat such disorders are provided, as are methods for using such ligands for receptor localization studies.

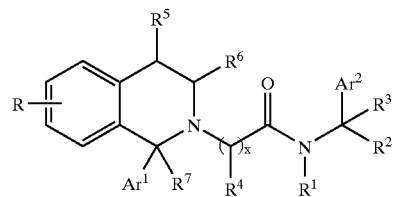

20 Claims, No Drawings

SUBSTITUTED TETRAHYDROISOQUINOLINES AS C5A RECEPTOR MODULATORS

CROSS-REFERENCE TO RELATED APPLICATION

This application claims priority to U.S. Provisional Application 60/368,199, filed Mar. 28, 2002.

FIELD OF THE INVENTION

This invention relates generally to substituted tetrahydroisoquinolines that act as modulators of mammalian complement C5a receptors, and to the use of such compounds for treating a variety of inflammatory and immune system disorders. The invention further relates to the use of such compounds as probes for the localization of C5a receptors.

BACKGROUND OF THE INVENTION

C5a, a 74 amino acid peptide, is generated in the complement cascade by the cleavage of the complement protein C5 by the complement C5 convertase enzyme. C5a has both anaphylatoxic (e.g., bronchoconstricting and vascular spasmogenic) and chemotactic effects. Therefore, it is active in engendering both the vascular and cellular phases of inflammatory responses. Because it is a plasma protein and, therefore, generally almost instantly available at a site of an inciting stimulus, it is a key mediator in terms of initiating the complex series of events that results in augmentation and amplification of an initial inflammatory stimulus. The anaphylatoxic and chemotactic effects of the C5a peptide are believed to be mediated through its interaction with the C5a receptor (CD88 antigen), a 52 kD membrane bound G-protein coupled receptor (GPCR). C5a is a potent chemoattractant for polymorphonuclear leukocytes, bringing neutrophils, basophils, eosinophils and monocytes to sites of inflammation and/or cellular injury. C5a is one of the most potent chemotactic agents known for a wide variety of inflammatory cell types. C5a also "primes" or prepares neutrophils for various antibacterial functions (e.g., phagocytosis). Additionally, C5a stimulates the release of inflammatory mediators (e.g., histamines, TNF-α, IL-1, IL-6, IL-8, prostaglandins, and leukotrienes) and the release of lysosomal enzymes and other cytotoxic components from granulocytes. Among its other actions, C5a also promotes the production of activated oxygen radicals and the contraction of smooth muscle.

Considerable experimental evidence implicates increased levels of C5a in a number of autoimmune diseases and inflammatory and related disorders.

Agents that block the binding of C5a to its receptor other agents, including inverse agonists, which modulate signal transduction associated with C5a-receptor interactions, can inhibit the pathogenic events, including chemotaxis, associated with anaphylatoxin activity contributing to such inflammatory and autoimmune conditions.

SUMMARY OF THE INVENTION

The present invention provides substituted tetrahydroisoquinolines and related compounds that are modulators of C5a receptor. Such modulators preferably inhibit C5a receptor activation and/or C5a receptor-mediated signal transduction. Within certain aspects, compounds provided herein and the pharmaceutically acceptable salts thereof are characterized by Formula I:

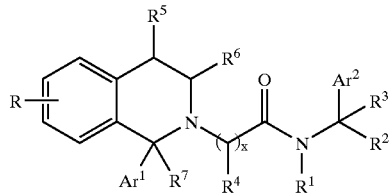

Formula I wherein: x is 1, 2 or 3.

R, in Formula I, represents from 0 to 4 substituents independently chosen from halogen, hydroxy, optionally substituted alkoxy, optionally substituted alkyl, optionally substituted alkenyl, optionally substituted alkynyl, cyano, amino, nitro, —COOH, carboxamide, optionally substituted mono- and di-alkyl amino, optionally substituted haloalkyl, and optionally substituted haloalkoxy.

$R^1$ is selected from alkyl, alkenyl, alkynyl, cycloalkyl, (cycloalkyl)alkyl, aryl, heteroaryl, (aryl)alkyl, (heteroaryl)alkyl, and indanyl, each of which is optionally substituted.

$R^2$, $R^3$ and each occurrence of $R^4$ are independently selected from hydrogen, halogen, optionally substituted alkyl, and optionally substituted alkoxy.

$R^5$ and $R^6$ are independently selected from (i) hydrogen, halogen, hydroxy, amino, and cyano; and (ii) alkyl, alkenyl, alkynyl, alkoxy, haloalkyl, haloalkoxy, and mono- and di-(alkyl)amino, each of which is optionally substituted.

$R^7$ is (a) (i) hydrogen; or (ii) alkyl, alkenyl, alkynyl, alkoxy or arylalkyl, each of which is optionally substituted; and $Ar^1$ is: (i) phenyl, naphthyl, biphenyl, or heterocycle, each of which is optionally substituted; or (ii) optionally substituted phenyl fused to a 5- to 7-membered saturated or partially unsaturated ring having from 5 to 7 ring atoms, with 0, 1, or 2 ring atoms independently chosen from N, O and S, and with remaining ring atoms being carbon, or $R^7$ is (b) taken together with $Ar^1$ and the carbon atom to which $R^7$ and $Ar^1$ are attached to form an optionally substituted group of the formula:

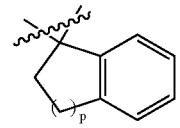

wherein p is an integer from 1 to about 3.

$Ar^2$ is (i) optionally substituted aryl or (ii) optionally substituted heteroaryl having 5 to 7 ring atoms and from 1 to 3 ring heteroatoms independently selected from N, O and S.

Within certain aspects, compounds as described above exhibit an $IC_{50}$ value no greater than 1 μM, 500 nM, 200 nM, 100 nM, 50 nM, 25 nM, 10 nM or 5 nM in a standard C5a receptor-mediated chemotaxis assay, radioligand binding assay, or calcium mobilization assay. Preferred C5a receptors are mammalian receptors that and may either be cloned, recombinantly expressed receptors or naturally expressed receptors. In certain embodiments the C5a receptors are primate C5a receptors, including human C5a receptors. In certain embodiments, C5a receptor modulators described herein exhibit an affinity for human C5a receptors that is higher than for non-primate C5a receptors; for example in certain embodiments compounds of Formula I exhibit 5-fold or 10-fold greater affinity for human C5a receptors that for most or all non-primate C5a receptors.

Certain aspects of the invention are directed to compounds of Formula I, above, that bind specifically to C5a receptors, and preferably also exhibit an $IC_{50}$ value no greater than 1 µM, 500 nM, 200 nM, 100 nM, 50 nM, 25 nM, 10 nM or 5 nM in a standard C5a receptor-mediated chemotaxis assay, radioligand binding assay, calcium mobilization assay.

The invention further provides, within certain embodiments, compounds of Formula I, that exhibit less than 5% agonist activity in a GTP binding assay.

The present invention further provides, within other aspects, pharmaceutical compositions comprising at least one compound or salt as described above (or a prodrug or hydrate thereof) in combination with a physiologically acceptable carrier or excipient.

The present invention provides, within further aspects, methods for treating a patient suffering from a condition responsive to C5a receptor modulation (e.g., a human or non-human animal, such as a domesticated companion animal or livestock animal). Such methods generally comprise administering to the patient a C5a receptor modulatory amount of at least one compound or salt as described above. For example, the invention comprises methods for treating a patient in need of anti-inflammatory treatment or immune treatment with an effective amount of a compound of the invention, e.g. an amount of a compound of the invention sufficient to yield a plasma concentration of the compound (or its active metabolite, if a pro-drug) or high enough to inhibit white blood cell (e.g., neutrophil) chemotaxis in vitro. Treatment of humans, domesticated companion animals (pets) or livestock animals suffering such conditions with an effective amount of a compound of the invention is contemplated by the invention. For treating non-human animals of any particular species, a compound exhibiting high affinity for the C5a receptor of that particular species is preferred.

Within further aspects, methods are provided for inhibiting signal transduction activity of a cellular C5a receptor, comprising contacting a cell expressing a C5a receptor with an effective amount of at least one compound or salt as described above. Such contact may occur in vivo or in vitro. In certain embodiments, the signal transduction activity inhibited is calcium conductance. In other embodiments, the signal transduction activity inhibited is C5a receptor-mediated cellular chemotaxis, and the method comprises contacting mammalian white blood cells with a C5a receptor modulatory amount of a compound or salt as described above.

Methods are further provided, within other aspects, for inhibiting binding of C5a to a C5a receptor. Within certain such aspects, the inhibition takes place in vitro. Such methods comprise contacting a C5a receptor with at least one compound or salt as described above, under conditions and in an amount sufficient to detectably inhibit C5a binding to the receptor. Within other such aspects, the C5a receptor is in a patient. Such methods comprise contacting cells expressing a C5a receptor in a patient with at least one compound or salt as described above at a concentration that would be sufficient to detectably inhibit C5a binding to cells expressing a cloned C5a receptor in vitro.

Compounds as described above are also, in certain aspects, labeled with a detectable marker (e.g., radiolabeled or fluorescein conjugated). The invention provides methods of using appropriately labeled compounds of the invention as probes for localization of receptors, particularly C5a receptors, for example in tissue sections (e.g., via autoradiography) or in vivo (e.g., via positron emission tomography, PET, or single positron emission computed tomography, SPECT, scanning and imaging).

In a separate aspect, the invention provides methods of using compounds of the invention as positive controls in assays for receptor activity, such as radioligand binding, calcium mobilization, and C5a-mediated chemotaxis assays.

The present invention further provides packaged pharmaceutical preparation, comprising: (a) a pharmaceutical composition as described herein in a container; and (b) instructions for using the composition to treat one or more conditions responsive to C5a receptor modulation.

In yet another aspect, the invention provides methods of preparing the compounds disclosed herein, including the intermediates.

These and other aspects of the present invention will become apparent upon reference to the following detailed description.

DETAILED DESCRIPTION OF THE INVENTION

Chemical Description and Terminology

Compounds of the present invention are generally described using standard nomenclature.

The term "substituted tetrahydroisoquinoline," as used herein, encompasses all compounds that satisfy one or more of Formulas I, IA, II, IIA, III, IV, V, VI, VII, VIII, IX and X herein, as well as pharmaceutically acceptable salts, prodrugs and hydrates of such compounds.

Certain compounds described herein contain one or more asymmetric elements such as stereogenic centers, stereogenic axes and the like (e.g., asymmetric carbon atoms) so that the compounds can exist in different stereoisomeric forms. These compounds can be, for example, racemates or optically active forms. For compounds with two or more asymmetric elements, these compounds can additionally be mixtures of diastereomers. Unless otherwise specified all optical isomers and mixtures thereof are encompassed for compounds having asymmetric centers. In addition, compounds with carbon-carbon double bonds may occur in Z- and E- forms, with all isomeric forms of the compounds being included in the present invention unless otherwise specified. Where a compound exists in various tautomeric forms, the invention is not limited to any one of the specific tautomers, but rather encompasses all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula, such as Formula I, that includes variables, such as various R groups, $Ar^1$, $Ar^2$, and x. Unless otherwise specified, each variable within such a formula is defined independently of other variables. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

A "substituent," as used herein, refers to a molecular moiety that is covalently bonded to an atom within a molecule of interest. For example, a "ring substituent" may be a moiety such as a halogen, alkyl group, haloalkyl group or other substituent discussed herein that is covalently bonded to an atom (preferably a carbon or nitrogen atom) that is a ring member. The term "substituted," as used herein, means that any one or more hydrogens on the designated atom is replaced with a selection from the indicated substituents, provided that the designated atom's normal valence is not exceeded, and that the substitution results in a stable compound (i.e., a compound that can be isolated, characterized and tested for biological activity). When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a tetrahydropyridone.

The phrase "optionally substituted" indicates that a group may either be unsubstituted or substituted at one or more of any of the available positions, typically 1, 2, 3, 4, or 5 positions, by one or more suitable substituents such as those disclosed herein. Various groups within the compounds and formulae set forth herein are "optionally substituted" including, for example, $R^1$, $R^2$, and $Ar^1$. Optional substitution may also be indicated by the phrase "substituted with from 0 to X substituents," in which X is the maximum number of substituents.

Suitable substituents include, for example, halogen, cyano, amino, hydroxy, nitro, azido, carboxamide, —COOH, $SO_2NH_2$, alkyl (e.g., $C_1$–$C_8$alkyl), alkenyl (e.g., $C_2$–$C_8$alkenyl), alkynyl (e.g., $C_2$–$C_8$alkynyl), alkoxy (e.g., $C_1$–$C_8$alkoxy), alkyl ether (e.g., $C_2$–$C_8$alkyl ether), alkylthio (e.g., $C_1$–$C_8$alkylthio), mono- or di-($C_1$–$C_8$alkyl)amino, haloalkyl (e.g., $C_1$–$C_6$haloalkyl), hydroxyalkyl (e.g., $C_1$–$C_6$hydroxyalkyl), aminoalkyl (e.g., $C_1$–$C_6$aminoalkyl), haloalkoxy (e.g., $C_1$–$C_6$haloalkoxy), alkanoyl (e.g., $C_1$–$C_8$alkanoyl), alkanone (e.g., $C_1$–$C_8$alkanone), alkanoyloxy (e.g., $C_1$–$C_8$alkanoyloxy), alkoxycarbonyl (e.g., $C_1$–$C_8$alkoxycarbonyl), mono- and di-($C_1$–$C_8$alkyl)amino, mono- and di-($C_1$–$C_8$alkyl)amino$C_1$–$C_8$alkyl, mono- and di-($C_1$–$C_8$alkyl)carboxamide, mono- and di-($C_1$–$C_8$alkyl) sulfonamido, alkylsulfinyl (e.g., $C_1$–$C_8$alkylsulfinyl), alkylsulfonyl (e.g., $C_1$–$C_8$alkylsulfonyl), aryl (e.g., phenyl), arylalkyl (e.g., ($C_6$–$C_{18}$aryl)$C_1$–$C_8$alkyl, such as benzyl and phenethyl), aryloxy (e.g., $C_6$–$C_{18}$aryloxy such as phenoxy), arylalkoxy (e.g., ($C_6$–$C_{18}$aryl)$C_1$–$C_8$alkoxy) and/or 3- to 8-membered heterocyclic groups. Certain groups within the formulas provided herein are optionally substituted with from 1 to 3, 1 to 4 or 1 to 5 independently selected substituents.

A dash ("-") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups, and where specified, having the specified number of carbon atoms. Thus, the term $C_1$–$C_6$alkyl, as used herein, indicates an alkyl group having from 1 to 6 carbon atoms. "$C_0$–$C_4$alkyl" refers to a bond or a $C_1$–$C_4$alkyl group. Alkyl groups include groups having from 1 to 8 carbon atoms ($C_1$–$C_8$alkyl), from 1 to 6 carbon atoms ($C_1$–$C_6$alkyl) and from 1 to 4 carbon atoms ($C_1$–$C_4$alkyl), such as methyl, ethyl, n-propyl, isopropyl, n-butyl, sec-butyl, tert-butyl, pentyl, 2-pentyl, isopentyl, neopentyl, hexyl, 2-hexyl, 3-hexyl, and 3-methylpentyl. "Aminoalkyl" is an alkyl group as defined herein substituted with one or more —$NH_2$ groups. "Hydroxyalkyl" is a hydroxy group as defined herein substituted with one or more —OH groups.

"Alkenyl" refers to a straight or branched hydrocarbon chain comprising one or more unsaturated carbon-carbon bonds, such as ethenyl and propenyl. Alkenyl groups include $C_2$–$C_8$alkenyl, $C_2$–$C_6$alkenyl and $C_2$–$C_4$alkenyl groups (which have from 2 to 8, 2 to 6 or 2 to 4 carbon atoms, respectively), such as ethenyl, allyl or isopropenyl.

"Alkynyl" refers to straight or branched hydrocarbon chains comprising one or more triple carbon-carbon bonds. Alkynyl groups include $C_2$–$C_8$alkynyl, $C_2$–$C_6$alkynyl and $C_2$–$C_4$alkynyl groups, which have from 2 to 8, 2 to 6 or 2 to 4 carbon atoms, respectively. Alkynyl groups include for example groups such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

The term "alkanoyl" refers to an acyl group in a linear or branched arrangement (e.g., —(C=O)-alkyl). Alkanoyl groups include $C_2$–$C_8$alkanoyl, $C_2$–$C_6$alkanoyl and $C_2$–$C_4$alkanoyl groups, which have from 2 to 8, 2 to 6, or 2 to 4 carbon atoms, respectively. "$C_1$alkanoyl" refers to —(C=O)—H, which (along with $C_2$–$C_8$alkanoyl) is encompassed by the term "$C_1$–$C_8$alkanoyl."

The term, "alkyl ether" refers to a linear or branched ether substituent linked via a carbon-carbon bond. Alkyl ether groups include $C_2$–$C_8$alkyl ether, $C_2$–$C_6$alkyl ether and $C_2$–$C_6$alkyl ether groups, which have 2 to 8, 2 to 6, or 2 to 4 carbon atoms, respectively. By way of example, a $C_2$alkyl ether group has the structure —$CH_2$—O—$CH_3$.

The term "alkoxycarbonyl" refers to an alkoxy group linked via a carbonyl (i.e., a group having the general structure —C(=O)—O-alkyl). Alkoxycarbonyl groups include $C_2$–$C_8$, $C_2$–$C_6$, and $C_2$–$C_4$alkoxycarbonyl groups, which have from 2 to 8, 2 to 6, or 2 to 4 carbon atoms, respectively. "$C_1$alkoxycarbonyl" refers to —C(=O)OH, and is encompassed by "$C_1$–$C_8$alkoxycarbonyl."

"Alkanoyloxy," as used herein, refers to an alkanoyl group linked via an oxygen bridge (i.e., a group having the general structure —O—C(=O)-alkyl). Alkanoyloxy groups include $C_2$–$C_8$, $C_2$–$C_6$, and $C_2$–$C_4$alkanoyloxy groups, which have from 2 to 8, 2 to 6, or 2 to 4 carbon atoms, respectively.

As used herein, the term "alkylthio" refers to an alkyl group attached via a thioether linkage. Alkylthio groups include $C_1$–$C_8$alkylthio, $C_1$–$C_6$alkylthio and $C_1$–$C_4$alkylthio, which have from 1 to 8, 1 to 6 or 1 to 4 carbon atoms, respectively.

"Alkylsulfinyl," as used herein, refers to an alkyl group attached via a sulfinyl linkage. Alkylsulfinyl groups include $C_1$–$C_8$alkylsulfinyl, $C_1$–$C_6$alkylsulfinyl, and $C_1$–$C_4$alkylsulfinyl, which have from 1 to 8, 1 to 6, and 1 to 4 carbon atoms, respectively.

By "alkylsulfonyl," as used herein, is meant an alkyl group attached via a sulfonyl linkage. Alkylsulfonyl groups include $C_1$–$C_8$alkylsulfonyl, $C_1$–$C_6$alkylsulfonyl, and $C_1$–$C_4$alkylsulfonyl, which have from 1 to 8, 1 to 6, and 1 to 4 carbon atoms, respectively.

"Alkylamino" refers to a secondary or tertiary amine having the general structure —NH-alkyl or —N(alkyl)(alkyl), wherein each alkyl may be the same or different. Such groups include, for example, mono- and di-($C_1$–$C_8$alkyl)amino groups, in which each alkyl may be the same or different and may contain from 1 to 8 carbon atoms, as well as mono- and di-($C_1$–$C_6$alkyl)amino groups and mono- and di-($C_1$–$C_4$alkyl)amino groups. Alkylaminoalkyl refers to an alkylamino group linked via an alkyl group (i.e., a group having the general structure -alkyl-NH-alkyl or -alkyl-N(alkyl)(alkyl)). Such groups include, for example, mono- and di-($C_1$–$C_8$alkyl)amino$C_1$–$C_8$alkyl, mono- and di-($C_1$–$C_6$alkyl)amino$C_1$–$C_6$alkyl, and mono- and di- ($C_1$–$C_4$alkyl)amino$C_1$–$C_4$alkyl, in which each alkyl may be the same or different.

The term "carboxamide" or "amido" refers to an amide group (i.e., —(C=O)NH$_2$). "Alkylcarboxamide" refers to —NHC(=O)alkyl, preferably —NHC(=O)$C_1$–$C_2$alkyl.

The term "cycloalkyl" refers to hydrocarbon ring groups, having the specified number of carbon atoms, usually from 3 to about 8 ring carbon atoms, or from. Cycloalkyl groups include $C_3$–$C_8$, and $C_3$–$C_7$ cycloalkyl groups, which have from 3 to 8 and 3 to 7 carbon atoms, respectively. Examples of cycloalkyl groups include cyclopropyl, cyclobutyl, cyclopentyl, and cyclohexyl groups, as well as bridged and caged saturated ring groups such as norbornane or adamantane and the like.

In the term "(cycloalkyl)alkyl," "cycloalkyl" and "alkyl" are as defined above, and the point of attachment is on the alkyl group. This term encompasses, but is not limited to, cyclopropylmethyl, cyclohexylmethyl, and cyclohexylethyl.

The term "halogen" indicates fluorine, chlorine, bromine, or iodine.

"Haloalkyl" refers to both branched and straight-chain saturated aliphatic hydrocarbon groups having the specified number of carbon atoms, substituted with 1 or more halogen atoms. Examples of haloalkyl include, but are not limited to, trifluoromethyl, difluoromethyl, 2-fluoroethyl, and pentafluoroethyl.

"Haloalkoxy" indicates a haloalkyl group as defined above attached through an oxygen bridge.

As used herein, the term "aryl" indicates aromatic groups containing only carbon in the aromatic ring(s). Such aromatic groups may be further substituted with carbon or non-carbon atoms or groups. Typical aryl groups contain 1 to 3 separate or fused rings, at least one of which is aromatic, and from 6 to about 18 ring atoms, without heteroatoms as ring members. Specifically preferred carbocyclic aryl groups include phenyl and napthyl, including 1-naphthyl and 2-naphthyl. When indicated, carbon atoms present within a carbocyclic ring may be optionally substituted with any of variety of ring substituents, as described above, or with specifically listed substituents.

The term "arylalkyl" refers to an aryl group is linked via an alkyl group. Certain arylalkyl groups are ($C_6$–$C_{18}$aryl)$C_1$–$C_8$alkyl groups (i.e., groups in which a 6- to 18-membered aryl group is linked via a $C_1$–$C_8$alkyl group). Such groups include, for example, groups in which phenyl or naphthyl is linked via a bond or $C_1$–$C_8$alkyl, preferably via $C_1$–$C_4$alkyl, such as benzyl, 1-phenyl-ethyl, 1-phenyl-propyl and 2-phenyl-ethyl.

The term "aryloxy" refers to an aryl group linked via a carbonyl (i.e., a group having the general structure —C(=O)—O-aryl). Phenoxy is a representative aryloxy group.

As used herein, the term "heteroaryl" is intended to indicate a stable 5-to 7-membered monocyclic or bicyclic or 7-to 10-membered bicyclic heterocyclic ring which contains at least 1 aromatic ring that contains from 1 to 4 heteroatoms selected from N, O, and S, with remaining ring atoms being carbon. When the total number of S and O atoms in the heteroaryl group exceeds 1, then these heteroatoms are not adjacent to one another. It is preferred that the total number of S and O atoms in the heterocycle is not more than 1, 2, or 3, more typically 1 or 2. It is particularly preferred that the total number of S and O atoms in the aromatic heterocycle is not more than 1. Examples of heteroaryl groups include pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, and 5,6,7,8-tetrahydroisoquinoline.

The term "heterocyclic group" or "heterocycle" is used to indicate saturated, partially unsaturated, or aromatic groups having 1 or 2 rings, 3 to 8 atoms in each ring and in at least one ring between 1 and 3 heteroatoms selected from N, O, and S. Any nitrogen or sulfur heteroatoms may optionally be oxidized. The heterocyclic group may be attached to its pendant group at any heteroatom or carbon atom that results in a stable structure. The heterocyclic groups described herein may be substituted on a carbon or nitrogen atom if the resulting compound is stable. A nitrogen in the heterocycle may optionally be quaternized.

Representative examples of heteroaryl groups and heterocyclic groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl;- 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"A C5a receptor" is a G-coupled protein receptor that specifically binds C5a protein. Preferably the C5a receptor is a human C5a receptor such as the protein product of the sequence of the resulting PCR product described by Gerard and Gerard, (1991) Nature 349:614–17. The human C5a receptor may also be that described by Boulay (1991) Biochemistry, 30(12): 2993–9 (GENBANK Accession No. M62505). Non-primate C5a receptors may be a rat C5a receptor such as a rat C5a receptor, GENBANK Accession Nos. X65862, Y09613, and AB003042, a canine C5a receptor, GENBANK Accession No. X65860, or a guinea pig C5a receptor, GENBANK Accession No. U86103.

A "C5a receptor modulator" is any compound that modulates C5a receptor activation and/or activity (i.e., C5a receptor-mediated signal transduction, as measured using a C5a receptor-mediated chemotaxis, radioligand binding assay, or calcium mobilization assay as provided herein). In certain embodiments, such a modulator may be exhibit an affinity constant or $IC_{50}$ for binding to a C5a receptor of less than 1 micromolar. In other embodiments the a C5a receptor modulator may exhibit an affinity constant or $IC_{50}$ of less than 500 nM, 200 nM, 100 nM, 50 nM, 25 nM, 10 nM or 5 nM in a standard C5a receptor-mediated chemotaxis assay, radioligand binding assay, or calcium mobilization assay. A modulator may be a C5a receptor agonist or antagonist, although, for certain purposes described herein, a modulator preferably inhibits C5a activation resulting from binding of C5a (i.e., the modulator is an antagonist). Preferred antagonists exhibit an antagonist $IC_{50}$ (which is used herein interchangeably with $EC_{50}$) of less than 1 micromolar, preferably less than 100 nanomolar, in an assay of C5a receptor-mediated chemotaxis, radioligand binding, and/or calcium mobilization. In addition, or alternatively, a modulator may act as an inverse agonist of C5a receptor. In certain embodiments, modulators provided herein modulate activation and/or activity of a primate C5a receptor, such as human C5a receptor, which may be a cloned, recombinantly expressed receptor or a naturally expressed receptor. For treating non-human animals of any particular species, a compound exhibiting high affinity for the C5a receptor of that particular species is preferred.

An "inverse agonist" of the C5a receptor is a compound which inhibits the activity of C5a at the C5a receptor, and reduces the activity of the C5a receptor below its basal activity level in the absence of added C5a. Inverse agonists of the C5a receptor may also inhibit binding of C5a to the C5a receptor. The ability of a compound to inhibit the binding of C5a to the C5a receptor may be measured by a binding assay, such as the radioligand binding assay given in Example 18. The basal activity of the C5a receptor may be determined from a GTP binding assay, such as the assay of Example 19. The reduction of C5a activity may also be determined from a GTP binding assay such as the assay of Example 19 or a calcium mobilization assay such as the assay of Example 20.

A "neutral antagonist" of the C5a receptor is a compound which inhibits the activity of C5a at the C5a receptor, but does not significantly change the basal activity of the C5a receptor. Neutral antagonists of the C5a receptor may inhibit the binding of C5a to the C5a receptor.

A "partial agonist" of the C5a receptor elevates the activity of the C5a receptor above the basal activity level of the receptor in the absence of C5a, but does not elevate the activity of the C5a receptor to the level brought about by saturating levels of the natural agonist, C5a. Partial agonist compounds may inhibit the binding of C5a to the C5a receptor. Partial agonists of the C5a receptor usually elevate the active of the C5a receptor from 5% to 90% of the activity level brought about by saturated concentrations of the natural agonist, C5a.

A "C5a receptor modulatory amount" of a compound is an amount that is sufficient to yield a plasma concentration of the compound (or its active metabolite, if a prodrug) high enough to detectably alter (modulate) C5a receptor activity and/or ligand binding, when that concentration is used in an in vitro assay. Suitable in vitro assays include the standard in vitro C5 receptor-mediated chemotaxis assay (described in Example 13 herein); C5a receptor-mediated calcium mobilization assay (described in Example 20 herein); and/or radioligand binding assay such as the assay provided in Example 18.

A "therapeutically effective amount" of a compound is an amount that is sufficient to result in a discernible patient benefit. For example, a therapeutically effective amount may reduce symptom severity or frequency. Alternatively, or in addition, a therapeutically effective amount may improve patient outcome and/or prevent or delay disease or symptom onset.

As used herein, a "pharmaceutically acceptable salt" is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, $HOOC-(CH_2)_n-COOH$ where n is 0–4 and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). Accordingly, the present disclosure should be construed to include all pharmaceutically acceptable salts of the compounds specifically recited. A wide variety of synthetic procedures is available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water, an organic solvent, or a mixture of the two; generally, nonaqueous media like ether, ethyl acetate, ethanol, isopropanol or acetonitrile are preferred.

A "prodrug" is a compound that may not fully satisfy the structural requirements of the compounds provided herein, but is modified in vivo, following administration to a patient, to produce a substituted tetrahydroisoquinoline. For example, a prodrug may be an acylated derivative of a compound as provided herein. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, and benzoate derivatives of alcohol and amine functional groups within the compounds provided herein. Preferred prodrugs include acylated derivatives. Prodrugs may be prepared by modifying functional groups present in the compounds in such a way that the modifications are cleaved to the parent compounds. Those of ordinary skill in the art will recognize various synthetic methods that may be employed to prepare prodrugs of the compounds provided herein.

A "patient" is any individual treated with a C5a modulator as provided herein. Patients include humans, as well as other animals such as companion animals (e.g., dogs and cats) and livestock. Patients may be experiencing one or more symptoms of a condition responsive to C5an receptor modulation, or may be free of such symptom(s) (i.e., treatment may be prophylactic).

C5a Receptor Modulators

As noted above, the present invention provides C5a receptor modulators (i.e., compounds that modulate C5a receptor-mediated signal transduction; preferably compounds that also detectably bind to C5a receptor). C5a receptor modulators may be used to modulate C5a receptor activity in a variety of contexts, including in the treatment of patients suffering from diseases or disorders responsive to C5a receptor modulation, such as autoimmune disorders and inflammatory conditions. C5a receptor modulators may also be used within a variety of in vitro assays (e.g., assays for receptor activity), as probes for detection and localization of C5a receptor and as standards in assays of ligand binding and C5a receptor-mediated signal transduction.

C5a receptor modulators provided herein are substituted tetrahydroisoquinolines of Formula I (as well as pharmaceutically acceptable salts and prodrugs thereof) that detectably alter, preferably decrease, C5a receptor activation and/or signal transduction activity at submicromolar concentrations. Such an alteration in C5a receptor activity may be measured using a standard in vitro C5a receptor-mediated chemotaxis assay (Example 13), a C5a receptor-mediated calcium mobilization assay (Example 20) and/or a radioligand binding assay (Example 18). The present invention is based, in part, on the discovery that small molecules of Formula I act as antagonists and/or inverse agonists of C5a receptors.

The invention includes compounds of Formula I

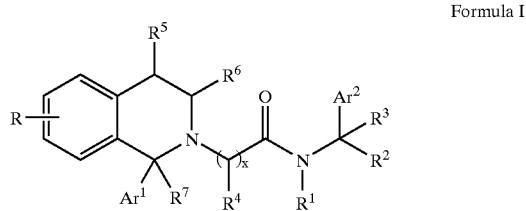

Formula I and the pharmaceutically acceptable salts thereof.

In this embodiment, x is 1.

R, in this embodiment, represents from 0 to 4 substituents independently chosen from halogen, hydroxy, cyano, amino, nitro, —COOH, carboxamide, $C_1$–$C_6$alkoxy, $C_1$–$C_6$alkyl, $C_2$–$C_6$alkenyl, $C_2$–$C_6$alkynyl, mono- and di-($C_1$–$C_6$alkyl) amino, $C_1$–$C_6$haloalkyl, and $C_1$–$C_6$haloalkoxy.

$R^1$ is selected from (aryl)$C_0$–$C_6$alkyl, (heteroaryl)$C_0$–$C_6$alkyl, and indanyl, each of which is substituted with from 0 to 3 substituents independently selected from halogen, hydroxy, cyano, amino, nitro, —COOH, carboxamide, $C_1$–$C_6$alkoxy, $C_1$–$C_6$alkyl, $C_2$–$C_6$alkenyl, $C_2$–$C_6$alkynyl, mono- and di-($C_1$–$C_6$alkyl)amino, $C_1$–$C_6$haloalkyl, and $C_1$–$C_6$haloalkoxy.

$R^2$, $R^3$, and each occurrence of $R^4$ are independently selected from hydrogen, halogen, $C_1$–$C_6$alkyl, and $C_1$–$C_6$alkoxy.

$R^5$ and $R^6$ are independently selected from hydrogen, halogen, cyano, $C_1$–$C_6$alkyl, $C_2$–$C_6$alkenyl, $C_2$–$C_6$alkynyl, $C_1$–$C_6$alkoxy, $C_1$–$C_6$haloalkyl, $C_1$–$C_6$haloalkoxy, hydroxy, amino, and mono- and di-($C_1$–$C_6$alkyl)amino.

Either:

(a) $R^7$ is (i) hydrogen; or (ii) $C_1$–$C_6$alkyl, $C_2$–$C_6$alkenyl, $C_1$–$C_6$alkynyl, $C_1$–$C_6$alkoxy or (aryl)$C_1$–$C_6$alkyl, each of which is optionally substituted; and $Ar^1$ is (i) phenyl; (ii) naphthyl; (iii) biphenyl; (iv) a heterocyclic group having 1 or 2 rings, 3 to 8 atoms in each ring and in at least one ring from 1 to 3 heteroatoms independently selected from N, O and S; or (v) phenyl fused to a 5- to 7-membered saturated or partially unsaturated ring having from 5 to 7 ring atoms, with 0, 1 or 2 ring atoms chosen from N, O and S, and with remaining ring atoms being carbon; wherein each of (i), (ii), (iii), (iv) and (v) is substituted with from 0 to 4 substituents independently selected from halogen, hydroxy, cyano, amino, nitro, $C_1$–$C_6$alkoxy, $C_1$–$C_6$alkyl, $C_2$–$C_6$alkenyl, $C_2$–$C_6$alkynyl, $C_1$–$C_6$alkoxycarbonyl, —COOH, carboxamide, mono- and di-($C_1$–$C_6$alkyl)amino, $C_1$–$C_6$haloalkyl, and $C_1$–$C_6$haloalkoxy; or (b) $R^7$ is taken together with $Ar^1$ and the carbon atom to which $R^7$ and $Ar^1$ are attached to form a group of the formula:

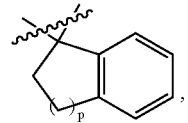

substituted with from 0 to 4 substituents independently chosen from halogen, hydroxy, cyano, amino, nitro, —COOH, carboxamide, $C_1$–$C_6$ alkoxy, $C_1$–$C_6$alkyl, $C_2$–$C_6$alkenyl, $C_2$–$C_6$alkynyl, mono- and di-($C_1$–$C_6$alkyl) amino, $C_1$–$C_6$haloalkyl, and $C_1$–$C_6$haloalkoxy, wherein p is an integer from 1 to about 3.

$Ar^2$ is aryl or heteroaryl, each of which is substituted with from 0 to 5 substituents independently selected from halogen, hydroxy, cyano, amino, nitro, —COOH, $C_1$–$C_6$alkoxy, $C_1$–$C_6$alkyl, $C_2$–$C_6$alkenyl, $C_2$–$C_6$alkynyl, $C_1$–$C_6$alkoxycarbonyl, carboxamide, mono- and di-($C_1$–$C_6$alkyl)carboxamide, mono- and di-($C_1$–$C_6$alkyl) amino, $C_1$–$C_6$haloalkyl, and $C_1$–$C_6$haloalkoxy.

Such compounds will be referred to as compounds of Formula IA.

In certain embodiments the invention includes compounds and salts of Formula I and Formula IA in which $R^1$ is indanyl, substituted with 0, 1, or 2 substituents independently selected from halogen, hydroxy, $C_1$–$C_2$alkoxy, $C_1$–$C_2$alkyl, halo$C_1$–$C_2$alkyl, and halo$C_1$–$C_2$alkoxy.

$R^1$, in other compounds and salts of Formula I and Formula IA, is phenyl($C_0$–$C_4$alkyl), pyridyl($C_0$–$C_4$alkyl), $C_0$–$C_4$alkyl, or indolyl($C_0$–$C_4$alkyl), each of which is substituted with from 0 to 3 substituents independently selected from halogen, hydroxy, $C_1$–$C_2$alkoxy, $C_1$–$C_2$alkyl, $C_1$–$C_2$haloalkyl, and $C_1$–$C_2$haloalkoxy.

$R^1$, in for still other compounds and salts of Formula IA, is phenyl($C_0$–$C_2$alkyl) substituted with from 0 to 3 substituents independently selected from halogen, hydroxy, $C_1$–$C_2$alkoxy, $C_1$–$C_2$alkyl, $C_1$–$C_2$haloalkyl, and $C_1$–$C_2$haloalkoxy.

The present invention also pertains to compounds and salts of Formula I and Formula IA in which $R^2$ and $R^3$ are hydrogen.

$R^4$, for certain compounds and salts of Formula I and Formula IA, is independently hydrogen or $C_1$–$C_6$alkyl.

$R^5$ and $R^6$, for particular compounds and salts of Formula I and Formula IA, are independently selected from hydrogen, halogen, $C_1$–$C_2$alkyl and $C_1$–$C_2$alkoxy.

Other embodiments of the invention include compounds and salts of Formula I and Formula IA in which R represents 0, 1, or 2 substituents independently selected from $C_1$–$C_6$alkyl, $C_1$–$C_6$alkoxy, $C_1$–$C_2$haloalkyl, $C_1$–$C_2$haloalkoxy, fluoro, and chloro.

In another aspect the invention includes compounds and salts of Formula I and Formula IA in which:

R represents 0, 1, or 2 substituents independently selected from hydrogen, methyl, ethyl, methoxy, trifluoromethyl, trifluoromethoxy, fluoro, and chloro, $R^2$, $R^3$, and $R^6$ are hydrogen; and $R^5$, $R^7$, and each $R^4$ are independently selected from hydrogen, methyl, and ethyl.

The present invention also pertains to compound and pharmaceutically acceptable salts of Formula II

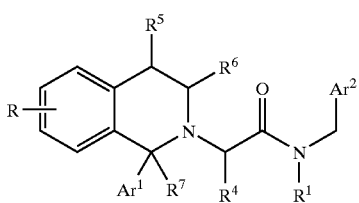

Formula II

R, Ar¹, and Ar² in Formula II carry the definitions given for these variables in Formula I or in certain embodiments carry the definitions given in Formula IA.

R, in Formula II, represents from 0 to 4 substituents independently chosen from fluoro, chloro, hydroxy, optionally substituted $C_1$–$C_6$alkoxy and optionally substituted $C_1$–$C_6$alkyl.

$R^4$ is hydrogen, optionally substituted $C_1$–$C_6$alkyl, $C_1$–$C_6$haloalkyl, fluoro, or chloro.

$R^5$ and $R^6$ are independently selected from hydrogen, fluoro, chloro, optionally substituted $C_1$–$C_6$alkyl, optionally substituted $C_1$–$C_6$alkoxy, $C_1$–$C_6$haloalkyl, and $C_1$–$C_6$haloalkoxy.

$R^7$ is hydrogen or $C_1$–$C_6$ alkyl.

Certain embodiments of the invention pertain to compounds and salts of Formula II in which:

Ar¹ and Ar² carry the definitions given for these variables in Formula I or in certain embodiments carry the definitions given in Formula IA.

R represents from 0 to 4 substituents independently chosen from fluoro, chloro, hydroxy, $C_1$–$C_6$alkoxy, and $C_1$–$C_6$alkyl.

$R^1$ is selected from $C_3$–$C_7$cycloalkyl, ($C_3$–$C_7$cycloalkyl) $C_1$–$C_4$alkyl, (heteroaryl)$C_0$–$C_4$alkyl, (aryl)$C_0$–$C_4$alkyl, and indanyl, each of which is substituted with from 0 to 3 substituents independently selected from halogen, hydroxy, cyano, amino, nitro, C–$C_6$alkoxy, $C_1$–$C_6$alkyl, $C_2$–$C_6$alkenyl, $C_2$–$C_6$alkynyl, —COOH, carboxamide, mono- and di-($C_1$–$C_6$alkyl)amino, $C_1$–$C_6$haloalkyl, and $C_1$–$C_6$haloalkoxy;

$R^4$ is hydrogen, $C_1$–$C_6$alkyl, $C_1$–$C_6$haloalkyl, fluoro, or chloro.

$R^5$ and $R^6$ are independently selected from hydrogen, fluoro, chloro, $C_1$–$C_6$alkyl, $C_1$–$C_6$alkoxy, halo$C_1$–$C_6$alkyl, and $C_1$–$C_6$haloalkoxy.

$R^7$ is hydrogen or $C_1$–$C_6$ alkyl.

The invention also includes compounds and salts of Formula II in which:

Ar¹ is: (i) phenyl substituted with from 0 to 4 substituents independently selected from halogen, hydroxy, cyano, amino, nitro, —COOH, carboxamide, $C_1$–$C_3$alkoxy, $C_1$–$C_3$alkyl, $C_1$–$C_2$haloalkyl, $C_1$–$C_2$alkoxycarbonyl, mono- and di-($C_1$–$C_2$alkyl)amino, and $C_1$–$C_2$haloalkoxy; (ii) naphthyl; (iii) heterocyclic groups having 1 or 2 rings, 3 to 8 atoms in each ring and in at least one ring from 1 to 3 heteroatoms independently selected from N, O and S; (iv) biphenyl, wherein each phenyl group is substituted with 0 to 2 groups independently selected from halogen, $C_1$–$C_2$alkyl, and $C_1$–$C_2$alkoxy; or (v) phenyl fused to a 5- to 7-membered saturated or partially unsaturated ring having from 5 to 7 ring atoms, with 0, 1, or 2 ring atoms independently chosen from N, O and S, and with remaining ring atoms being carbon; wherein each of (ii), (iii), (iv) and (v) is substituted with from 0 to 4 substituents independently selected from halogen, hydroxy, $C_1$–$C_2$alkyl, $C_1$–$C_2$alkoxy, $C_1$–$C_2$haloalkyl, and halo$C_1$–$C_2$alkoxy.

Additional embodiments of the invention pertain to compounds and salts of Formula II in which Ar² is phenyl or heteroaryl having about 5 to 7 ring atoms and between 1 and 3 ring heteroatoms independently selected from N, O and S, each of which is substituted with from 0 to 5 substituents independently selected from halogen, hydroxy, cyano, amino, nitro, —COOH, $C_1$–$C_3$alkoxy, $C_1$–$C_3$alkyl, carboxamide, dimethylcarboxamide, mono- and di-($C_1$–$C_2$alkyl)amino, $C_1$–$C_2$haloalkyl, and $C_1$–$C_2$haloalkoxy.

In certain embodiments the invention pertains to compounds and salts of Formula II in which Ar² is phenyl or heteroaryl having about 5 to 7 ring atoms and between 1 and 3 ring heteroatoms independently selected from N, O and S, each of which is substituted with from 0 to 5 substituents independently selected from halogen, hydroxy, cyano, amino, nitro, —COOH, $C_1$–$C_3$alkoxy, $C_1$–$C_3$alkyl, carboxamide, dimethylcarboxamide, mono- and di-($C_1$–$C_2$alkyl)amino, $C_1$–$C_2$haloalkyl, and $C_1$–$C_2$haloalkoxy.

Other embodiments of the invention include compounds and salts of Formula II in which:

R represents from 0 to 2 substituents independently chosen from fluoro, chloro, hydroxy, methoxy, ethoxy, methyl, and ethyl.

$R^1$ is 1-indanyl or 2-indanyl, each of which is substituted with from 0 to 3 substituents independently selected from halogen, hydroxy, cyano, amino, nitro, $C_1$–$C_6$alkoxy, $C_1$–$C_6$alkyl, $C_2$–$C_6$alkenyl, $C_2$–$C_6$alkynyl, —COOH, carboxamide, mono- and di-($C_1$–$C_6$alkyl) amino, $C_1$–$C_6$haloalkyl, and $C_1$–$C_6$haloalkoxy.

$R^4$ is hydrogen, $C_1$–$C_6$alkyl, $C_1$–$C_6$haloalkyl, fluoro, or chloro; and $R^5$ and $R^6$ are independently selected from hydrogen, fluoro, chloro, $C_1$–$C_6$alkyl, $C_1$–$C_6$alkoxy, halo$C_1$–$C_6$alkyl, and $C_1$–$C_6$haloalkoxy.

$R^7$ is hydrogen, methyl or ethyl.

Ar¹ is (i) phenyl substituted with from 0 to 5 substituents independently selected from halogen, hydroxy, cyano, amino, nitro, —COOH, carboxamide, $C_1$–$C_3$alkoxy, $C_1$–$C_3$alkyl, $C_1$–$C_2$alkoxycarbonyl, mono- and di-($C_1$–$C_2$alkyl)amino, halo$C_1$–$C_2$alkyl, and halo$C_1$–$C_2$alkoxy;

(ii) naphthyl;

(iii) heterocyclic groups having 1 or 2 rings, 3 to 8 atoms in each ring, and in at least one ring from 1 to 3 heteroatoms independently selected from N, O and S;

(iv) biphenyl; or (v) phenyl fused to a 5- to 7-membered saturated or partially unsaturated ring having from 5 to 7 ring atoms, with 0, 1, or 2 ring atoms independently chosen from N, O and S, and with remaining ring atoms being carbon; wherein each of (ii), (iii), (iv) and (v) is substituted with from 0 to about 4 substituents independently selected from halogen, hydroxy, $C_1$–$C_2$alkyl, $C_1$–$C_2$alkoxy, $C_1$–$C_2$haloalkyl, and $C_1$–$C_2$haloalkoxy.

Ar² is phenyl, pyridyl, thiazolyl, pyrimidyl, pyridizinyl, imidazolyl, oxazolyl, isoxazolyl and triazolyl, each of which is substituted with from 0 to 3 substituents independently chosen from halogen, hydroxy, cyano, amino, nitro, —COOH, $C_1$–$C_3$alkoxy, $C_1$–$C_3$alkyl, carboxamide, dimethylcarboxamide, mono- and di-($C_1$–$C_2$alkyl)amino, $C_1$–$C_2$haloalkyl, and $C_1$–$C_2$haloalkoxy.

The invention also includes as additional embodiments, compounds and salts of Formula II in which:

R represents from 0 to 2 substituents independently chosen from fluoro, chloro, hydroxy, methoxy, ethoxy, methyl and ethyl.

$R^1$ is 2-indanyl, substituted with 0, 1, or 2 substituents independently selected from fluoro, chloro, hydroxy, methyl, ethyl, methoxy, ethoxy, mono-, di- and tri-fluoromethyl, and mono-, di-, and tri-fluoromethoxy.

$R^4$ is hydrogen, fluoro, chloro, methyl, ethyl, methoxy, mono-, di-, or tri-fluoromethyl, or mono-, di- or tri-fluoromethoxy.

$R^5$ and $R^6$ are independently selected from hydrogen, fluoro, chloro, methyl, ethyl, methoxy, ethoxy, mono-, di- and tri-fluoromethyl, and mono-, di-, and tri-fluoromethoxy.

$R^7$ is hydrogen, methyl or ethyl.

$Ar^1$ is: (i) phenyl, substituted with from 0 to 3 substituents independently selected from fluoro, chloro, bromo, hydroxy, methyl, methoxy, ethyl, ethoxy, mono-, di- and tri-fluoromethyl, and mono-, di-, and tri-fluoromethoxy; or (ii) naphthyl, substituted with from 0 to 3 substituents independently selected from fluoro, chloro, hydroxy, methyl, ethyl, methoxy, and ethoxy.

$Ar^2$ is phenyl, 2-pyridyl, 3-pyridyl, 4-pyridyl, 2-thienyl, 3-thienyl or 1,3-thiazol-2-yl, each of which is substituted with from 0 to 3 substituents independently chosen from halogen, hydroxy, cyano, amino, nitro, —COOH, $C_1$–$C_3$alkoxy, $C_1$–$C_3$alkyl, carboxamide, dimethylcarboxamide, mono- and di-($C_1$–$C_2$alkyl)amino, $C_1$–$C_2$haloalkyl, and $C_1$–$C_2$haloalkoxy.

Other embodiments of the invention pertain to compounds and salts of Formula II in which:

R represents from 0 to 2 substituents independently chosen from fluoro, chloro, hydroxy, methoxy, ethoxy, methyl, and ethyl.

$R^1$ is phenyl($C_0$–$C_2$alkyl), substituted with from 0 to 3 substituents independently selected from halogen, hydroxy, $C_1$–$C_6$alkoxy, $C_1$–$C_6$alkyl, $C_2$–$C_6$alkenyl, $C_2$–$C_6$alkynyl, cyano, amino, nitro, —COOH, carboxamide, mono- and di-($C_1$–$C_6$alkyl) amino, $C_1$–$C_6$haloalkyl, and $C_1$–$C_6$haloalkoxy. Or preferably, $R^1$ is phenyl($C_0$–$C_1$alkyl), substituted with from 0 to 3 substituents independently selected from halogen, hydroxy, $C_1$–$C_4$alkoxy, $C_1$–$C_4$alkyl, —COOH, carboxamide, mono- and di-($C_1$–$C_4$alkyl) amino, $C_1$–$C_2$haloalkyl, and $C_1$–$C_2$haloalkoxy.

$R^4$ is hydrogen, $C_1$–$C_6$alkyl, $C_1$–$C_6$haloalkyl, fluoro, or chloro; and $R^5$ and $R^6$ are independently selected from hydrogen, fluoro, chloro, $C_1$–$C_6$alkyl, $C_1$–$C_6$alkoxy, halo$C_1$–$C_6$alkyl, and $C_1$–$C_6$haloalkoxy.

$R^7$ is hydrogen, methyl, or ethyl. $Ar_1$ is: (i) phenyl substituted with from 0 to 5 substituents independently selected from halogen, hydroxy, cyano, amino, nitro, —COOH, carboxamide, $C_1$–$C_3$alkoxy, $C_1$–$C_3$alkyl, $C_1$–$C_2$alkoxycarbonyl, mono- and di-($C_1$–$C_2$alkyl)amino, $C_1$–$C_2$haloalkyl, and $C_1$–$C_2$halo$C_1$–$C_2$alkoxy; (ii) naphthyl; (iii) a heterocyclic group having 1 or 2 rings, 3 to 8 atoms in each ring, and in at least one ring from 1 to 3 heteroatoms independently selected from N, O and S; (iv) biphenyl; or (v) phenyl fused to a 5- to 7-membered saturated or partially unsaturated ring having from 5 to 7 ring atoms, with 0, 1 or 2 ring atoms independently chosen from N, O and S, and with remaining ring atoms being carbon; wherein each of (ii), (iii), (iv) and (v) is substituted with from 0 to about 4 substituents independently selected from halogen, hydroxy, $C_1$–$C_2$alkyl, $C_1$–$C_2$alkoxy, halo$C_1$–$C_6$alkyl, and halo$C_1$–$C_2$alkoxy.

$Ar^2$ is phenyl, pyridyl, thiazolyl, pyrimidyl, pyridizinyl, imidazolyl, oxazolyl, isoxazolyl or triazolyl, each of which is substituted with from 0 to 3 substituents independently chosen from halogen, hydroxy, cyano, amino, nitro, —COOH, $C_1$–$C_3$alkoxy, $C_1$–$C_3$alkyl, carboxamide, dimethylcarboxamide, mono- and di-($C_1$–$C_2$alkyl)amino, halo$C_1$–$C_2$alkyl and halo$C_1$–$C_2$alkoxy.

The present invention also includes compounds and pharmaceutically acceptable salts of Formula III:

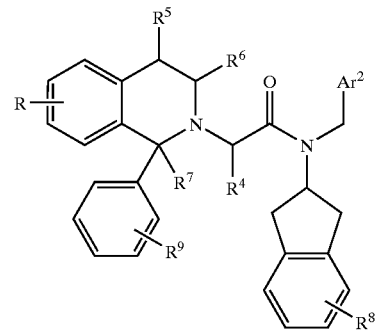

Formula III

R, in Formula III, represents from 0 to 4 substituents independently chosen from fluoro, chloro, hydroxy, $C_1$–$C_6$alkoxy, and $C_1$–$C_6$alkyl.

$R^4$ is hydrogen, $C_1$–$C_6$alkyl, $C_1$–$C_6$haloalkyl, fluoro, or chloro.

$R^8$ represents from 0 to 4 substituents independently chosen from $C_1$–$C_6$alkyl, $C_1$–$C_6$alkoxy, $C_1$–$C_6$haloalkyl, $C_1$–$C_6$haloalkoxy, fluoro, and chloro.

$R^5$ and $R^6$ are independently selected from hydrogen, fluoro, chloro, $C_1$–$C_6$alkyl, optionally substituted $C_1$–$C_6$alkoxy, and halo$C_1$–$C_6$alkyl.

$R^7$ is hydrogen or $C_1$–$C_6$alkyl.

$R^9$ represents from 0 to 5 substituents independently chosen from halogen, hydroxy, $C_1$–$C_6$alkyl, $C_1$–$C_6$alkoxy, $C_1$–$C_6$haloalkyl, and $C_1$–$C_6$haloalkoxy.

$Ar^2$ is (i) phenyl or (ii) heteroaryl having 5 to 7 ring atoms and from 1 to 3 ring heteroatoms independently selected from N, O and S, wherein each of (i) and (ii) is optionally substituted with from 1 to 5 substituents independently selected from halogen, hydroxy, cyano, amino, nitro, —COOH, carboxamide, dimethylcarboxamide, $C_1$–$C_3$alkoxy, $C_1$–$C_3$alkyl, mono- and di-($C_1$–$C_2$alkyl) amino, $C_1$–$C_2$haloalkyl, and $C_1$–$C_2$haloalkoxy.

In another aspect the invention pertains to compounds and pharmaceutically acceptable salts of Formula IV:

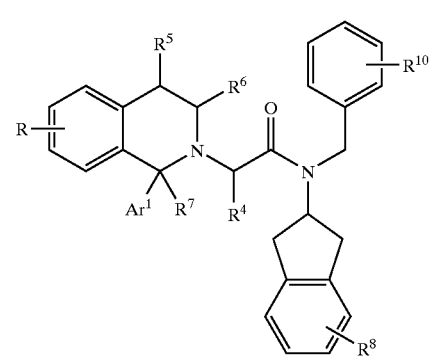

Formula IV

R, in Formula IV represents from 0 to 4 substituents independently chosen from fluoro, chloro, hydroxy, $C_1$–$C_6$alkoxy, and $C_1$–$C_6$alkyl.

$R^4$ is hydrogen, $C_1$–$C_6$alkyl, $C_1$–$C_6$haloalkyl, fluoro, or chloro.

$R^8$ represents from 0 to 4 substituents independently chosen from $C_1$–$C_6$alkyl, $C_1$–$C_6$haloalkyl, fluoro, and chloro.

$R^5$ and $R^6$ are independently selected from hydrogen, fluoro, chloro, $C_1$–$C_6$alkyl, optionally substituted $C_1$–$C_6$alkoxy, and $C_1$–$C_6$haloalkyl.

$R^7$ is hydrogen or $C_1$–$C_6$alkyl.

$R^{10}$ represents from 0 to 5 substituents independently chosen from fluoro, chloro, bromo, iodo, hydroxy, nitro, cyano, —COOH, carboxamide, dimethylcarboxamide, $C_1$–$C_6$alkyl, $C_1$–$C_6$alkoxy, $C_1$–$C_6$haloalkyl, and $C_1$–$C_6$haloalkoxy.

$Ar_1$, in Formula IV, is: (i) phenyl substituted with from 0 to 5 substituents independently selected from halogen, hydroxy, cyano, amino, nitro, —COOH, carboxamide, $C_1$–$C_3$alkoxy, $C_1$–$C_3$alkyl, $C_1$–$C_2$haloalkyl, $C_1$–$C_2$alkoxycarbonyl, mono- and di-($C_1$–$C_2$alkyl)amino, and $C_1$–$C_2$haloalkoxy; (ii) naphthyl; (iii) heterocyclic groups having 1 or 2 rings, 3 to 8 atoms in each ring and in at least one ring from 1 to 3 heteroatoms independently selected from N, O and S; (iv) biphenyl; or (v) phenyl fused to a 5- to 7-membered saturated or partially unsaturated ring having from 5 to 7 ring atoms, with 0, 1, or 2 ring atoms independently chosen from N, O and S, and with remaining ring atoms being carbon; wherein each of (ii), (iii), (iv) and (v) is substituted with from 0 to 4 substituents independently selected from halogen, hydroxy, $C_1$–$C_2$alkyl, $C_1$–$C_2$alkoxy, $C_1$–$C_2$haloalkyl, and $C_1$–$C_2$haloalkoxy.

The present invention also includes compounds and pharmaceutically acceptable salts of Formula V.

Formula V

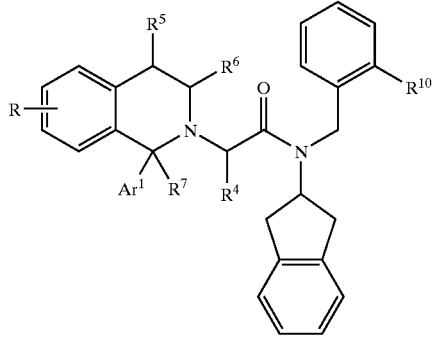

R, in Formula V, represents from 0 to 4 substituents independently chosen from fluoro, chloro, hydroxy, methyl, ethyl, methoxy, or ethoxy.

$R^4$ is hydrogen, fluoro, chloro, methyl, ethyl, methoxy, mono-, di- or tri-fluoromethyl, or mono-, di-, or tri-fluoromethoxy.

$R^5$ and $R^6$ are independently chosen from hydrogen, fluoro, chloro, methyl, methoxy, mono-, di- and tri-fluoromethyl, and mono-, di- and tri-fluoromethoxy.

$R^7$ is hydrogen, methyl, or ethyl; and $R^{10}$ is hydrogen, fluoro, chloro, bromo, hydroxy, methyl, ethyl, methoxy, or ethoxy.

Also included within the invention are compounds and pharmaceutically acceptable salts of Formula VI:

Formula VI

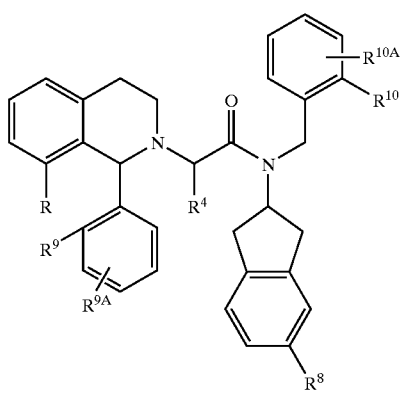

R, in Formula VI, is hydrogen, fluoro, chloro, hydroxy, methyl, or methoxy.

$R^4$ is hydrogen, methyl, or ethyl; $R^8$ is hydrogen, fluoro, chloro, methyl, or methoxy.

$R^9$ is fluoro, chloro, methyl, ethyl, methoxy, ethoxy, mono-, di- or tri-fluoromethyl, or mono-, di-, or tri-fluoromethoxy; $R^{9A}$ represents 0, 1, or 2 substituents independently selected from hydrogen, fluoro, chloro, methyl, methoxy, mono-, di- and tri-fluoromethyl, and mono-, di-, and tri-fluoromethoxy.

$R^{10}$ is hydrogen, fluoro, chloro, hydroxy, methyl, methoxy, mono-, di-, or tri-fluoromethyl, or mono-, di-, or tri-fluoromethoxy; and $R^{10A}$ represents from 0 to 3 substituents independently selected from hydrogen, fluoro, chloro, hydroxy, methyl, methoxy, mono-, di- and tri-fluoromethyl, and mono-, di-, and tri-fluoromethoxy.

The invention further pertains to compounds and pharmaceutically acceptable salts of Formula VII.

Formula VII

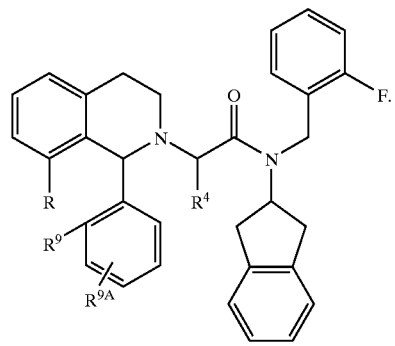

Wherein, the variables $R^4$, $R^9$, and $R^{9A}$ carry the definitions given in Formula VI.

The invention further pertains to compounds and pharmaceutically acceptable salts of Formula VIII Formula VIII

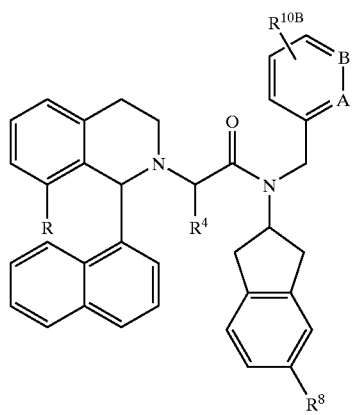

In Formula VIII, A is N or $CR^{10}$ and B is N or $CR^{10A}$, wherein at least one of A and B is not N.

R is hydrogen, fluoro, chloro, hydroxy, methyl, or methoxy.

$R^4$ is hydrogen, methyl, or ethyl.

$R^8$ is hydrogen, fluoro, chloro, methyl or methoxy.

$R^{10}$, if present, is hydrogen, fluoro, chloro, hydroxy, nitro, cyano, methyl, methoxy, mono-, di- or tri-fluoromethyl, or mono-, di-, or tri-fluoromethoxy; $R^{10A}$, if present, is hydrogen, fluoro, chloro, hydroxy, nitro, cyano, methyl, methoxy, mono-, di- or tri-fluoromethyl, or mono-, di-, or tri-fluoromethoxy; and $R^{10B}$ represents from 0 to 3 substituents independently selected from fluoro, chloro, hydroxy, nitro, cyano, methyl, methoxy, mono-, di- and tri-fluoromethyl, and mono-, di-, and tri-fluoromethoxy.

The invention also pertains to compounds and pharmaceutically acceptable salts of Formula IX:

Formula IX

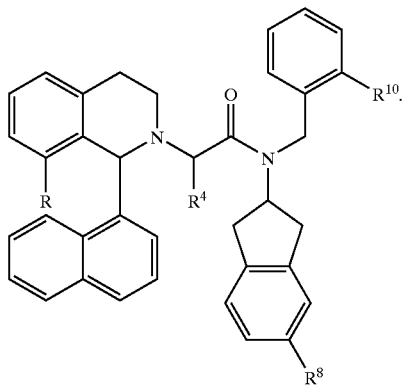

In Formula IX, R is hydrogen, fluoro, chloro, hydroxy, methyl or methoxy; $R^4$ is hydrogen, methyl, or ethyl; $R^8$ is hydrogen, fluoro, chloro, methyl or methoxy; and $R^{10}$ is hydrogen, fluoro, chloro, hydroxy, methyl, methoxy, mono-, di- or tri-fluoromethyl, or mono-, di-, or tri-fluoromethoxy.

In yet another embodiment, the invention pertains to compounds and pharmaceutically acceptable salts of Formula X Formula X

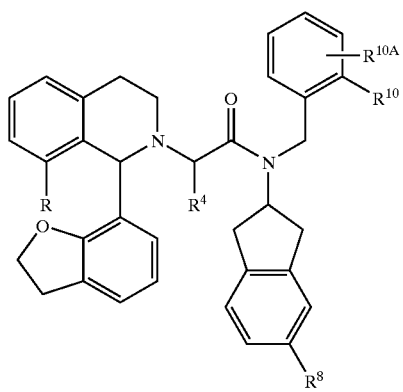

R, in Formula X, is hydrogen, fluoro, chloro, hydroxy, methyl or methoxy; $R^4$ is hydrogen, methyl, or ethyl; $R^8$ is hydrogen, fluoro, chloro, methyl or methoxy; $R^{10}$ is hydrogen, fluoro, chloro, hydroxy, methyl, methoxy, mono-, di- or tri-fluoro methyl, or mono-, di- or tri-fluoromethoxy; and $R^{10A}$ represents from 0 to 3 substituents independently selected from hydrogen, fluoro, chloro, hydroxy, methyl, methoxy, mono-, di- and tri-fluoromethyl, and mono-, di-, and tri-fluoromethoxy.

The invention also pertains to compounds and pharmaceutically acceptable salts of Formula XI:

Formula XI

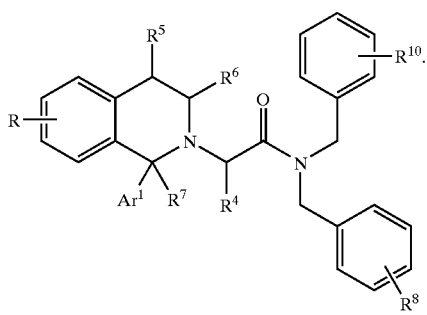

R represents from 0 to 4 substituents independently chosen from fluoro, chloro, hydroxy, $C_1$–$C_6$alkoxy, and $C_1$–$C_6$alkyl.

$R^4$ is hydrogen, $C_1$–$C_6$alkyl, $C_1$–$C_6$haloalkyl, fluoro, or chloro.

$R^8$ represents from 0 to 4 substituents independently chosen from $C_1$–$C_6$alkyl, $C_1$–$C_6$haloalkyl, fluoro, and chloro.

$R^5$ and $R^6$ are independently selected from hydrogen, fluoro, chloro, $C_1$–$C_6$alkyl, optionally substituted $C_1$–$C_6$alkoxy, and $C_1$–$C_6$haloalkyl.

$R^7$ is hydrogen or $C_1$–$C_6$alkyl.

$R^{10}$ represents from 0 to 5 substituents independently chosen from fluoro, chloro, bromo, iodo, hydroxy, nitro, cyano, —COOH, carboxamide, dimethylcarboxamide, $C_1$–$C_6$alkyl, $C_1$–$C_6$alkoxy, $C_1$–$C_6$haloalkyl, and $C_1$–$C_6$haloalkoxy.

$Ar_1$ is: (i) phenyl optionally substituted with from 1 to 5 substituents independently selected from halogen, hydroxy, cyano, amino, nitro, —COOH, carboxamide, $C_1$–$C_3$alkoxy, $C_1$–$C_3$alkyl, $C_1$–$C_2$haloalkyl, $C_1$–$C_2$alkoxycarbonyl, mono- and di-($C_1$–$C_2$alkyl)amino, and $C_1$–$C_2$haloalkoxy; (ii) naphthyl; (iii) heterocyclic groups having 1 or 2 rings, 3 to 8 atoms in each ring and in at least one ring from 1 to 3 heteroatoms independently selected from N, O and S; (iv) biphenyl; or (v) phenyl fused to a 5- to 7-membered saturated or partially unsaturated ring having from 5 to 7 ring atoms, with 0, 1, or 2 ring atoms independently chosen from N, O and S, and with remaining ring atoms being carbon; wherein each of (ii), (iii), (iv) and (v) is optionally substituted with from 1 to 4 substituents independently selected from halogen, hydroxy, $C_1$–$C_2$alkyl, $C_1$–$C_2$alkoxy, $C_1$–$C_2$haloalkyl, and $C_1$–$C_2$haloalkoxy.

In another aspect the invention pertains to compounds of Formula XII

Formula XII

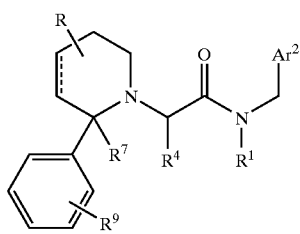

and the pharmaceutically acceptable salt thereof.

R, in Formula XII, represents from 0 to 4 substituents independently chosen from fluoro, chloro, hydroxy, $C_1$–$C_6$alkoxy, $C_1$–$C_6$alkyl, $C_1$–$C_2$haloalkyl, and $C_1$–$C_2$haloalkoxy;

$R^1$ and $Ar^2$ are independently chosen from: (i) phenyl ($C_0$–$C_1$alkyl), substituted with from 0 to 3 substituents independently selected from halogen, hydroxy, $C_1$–$C_6$alkoxy, $C_1$–$C_6$alkyl, $C_2$–$C_6$alkenyl, $C_2$–$C_6$alkynyl, cyano, amino, nitro, —COOH, carboxamide, mono- and di-($C_1$–$C_6$alkyl)amino, $C_1$–$C_6$haloalkyl and $C_1$–$C_6$haloalkoxy; and (ii) 2-indanyl, substituted with 0, 1 or 2 substituents independently selected from fluoro, chloro, hydroxy, methyl, ethyl, methoxy, ethoxy, mono-, di- and tri-fluoromethyl, and mono-, di- and tri-fluoromethoxy.

$R^4$ is $C_1$–$C_6$alkyl, $C_1$–$C_2$haloalkyl, fluoro or chloro; and $R^7$ is hydrogen or $C_1$–$C_6$alkyl.

$R^9$ represents from 0 to 5 substituents independently chosen from hydrogen, halogen, hydroxy, $C_1$–$C_6$alkyl, $C_1$–$C_6$alkoxy, $C_1$–$C_6$haloalkyl, and $C_1$–$C_6$haloalkoxy; and ⁞ represents a single or double bond.

In a separate aspect the invention pertains to Compounds of Formula XIII

Formula XIII

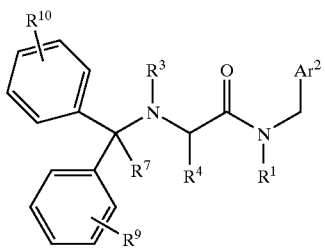

and the pharmaceutically acceptable salts thereof.

$R^1$ and $Ar^2$, in this embodiment, are independently chosen from: (i) phenyl($C_0$–$C_1$alkyl), substituted with from 0 to 3 substituents independently selected from halogen, hydroxy, $C_1$–$C_6$alkoxy, $C_1$–$C_6$alkyl, $C_2$–$C_6$alkenyl, $C_2$–$C_6$alkynyl, cyano, amino, nitro, —COOH, carboxamide, mono- and di-($C_1$–$C_6$alkyl) amino, $C_1$–$C_6$haloalkyl, and $C_1$–$C_6$haloalkoxy; and (ii) 2-indanyl, substituted with 0, 1 or 2 substituents independently selected from fluoro, chloro, hydroxy, methyl, ethyl, methoxy, ethoxy, mono-, di- and tri-fluoromethyl, and mono-, di- and tri-fluoromethoxy.

$R^4$ is $C_1$–$C_6$alkyl, halo$C_1$–$C_6$alkyl, fluoro or chloro.

$R^3$ and $R^7$ are independently hydrogen or $C_1$–$C_6$alkyl.

$R^9$ and $R^{10}$ independently represent from 0 to 5 substituents independently chosen from hydrogen, halogen, hydroxy, $C_1$–$C_6$alkyl, $C_1$–$C_6$alkoxy, $C_1$–$C_6$haloalkyl, and $C_1$–$C_6$haloalkoxy.

The invention further pertains to compounds and pharmaceutically acceptable salts of Formula XIV Formula XIV

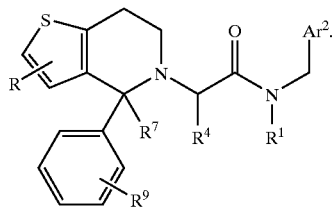

R, in Formula XIV, represents from 0 to 2 substituents independently chosen from fluoro, chloro, hydroxy, $C_1$–$C_6$alkoxy, $C_1$–$C_6$alkyl, $C_1$–$C_2$alkyl, and $C_1$–$C_2$alkoxy.

$R^1$ and $Ar^2$ are independently chosen from:

(i) phenyl($C_0$–$C_1$alkyl), substituted with from 0 to 3 substituents independently selected from halogen, hydroxy, $C_1$–$C_6$alkoxy, $C_1$–$C_6$alkyl, $C_2$–$C_6$alkenyl, $C_2$–$C_6$alkynyl, cyano, amino, nitro, —COOH, carboxamide, mono- and di-($C_1$–$C_6$alkyl) amino, halo$C_1$–$C_6$alkyl and halo$C_1$–$C_6$alkoxy; and (ii) 2-indanyl, substituted with 0, 1 or 2 substituents independently selected from fluoro, chloro, hydroxy, methyl, ethyl, methoxy, ethoxy, mono-, di- and tri-fluoromethyl, and mono-, di- and tri-fluoromethoxy.

$R^4$ is $C_1$–$C_6$alkyl, halo$C_1C_6$alkyl, fluoro or chloro; $R^7$ is hydrogen or $C_1$–$C_6$alkyl; and $R^9$ represents from 0 to 5 substituents independently chosen from hydrogen, halogen, hydroxy, $C_1$–$C_6$alkyl, $C_1$–$C_6$alkoxy, $C_1$–$C_6$haloalkyl, and $C_1$–$C_6$haloalkoxy.

In yet another aspect the invention pertains to compounds of Formula XV

Formula XV

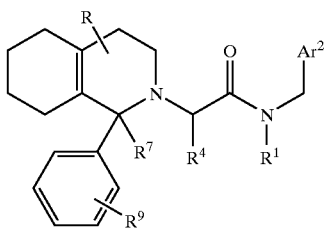

and the pharmaceutically acceptable salt thereof.

R, in Formula XV, is present on either ring to the two ring system and represents from 0 to 4 substituents independently chosen from fluoro, chloro, hydroxy, $C_1$–$C_6$alkoxy, $C_1$–$C_6$alkyl, $C_1$–$C_2$haloalkyl, and $C_1$–$C_2$haloalkoxy;

$R^1$ and $Ar^2$ are independently chosen from: (i) phenyl ($C_0$–$C_1$alkyl), substituted with from 0 to 3 substituents independently selected from halogen, hydroxy, $C_1$–$C_6$alkoxy, $C_1$–$C_6$alkyl, $C_2$–$C_6$alkenyl, $C_2$–$C_6$alkynyl, cyano, amino, nitro, —COOH, carboxamide, mono- and di-($C_1$–$C_6$alkyl)amino, $C_1$–$C_6$haloalkyl and $C_1$–$C_6$haloalkoxy; and (ii) 2-indanyl, substituted with 0, 1 or 2 substituents independently selected from fluoro, chloro, hydroxy, methyl, ethyl, methoxy, ethoxy, mono-, di- and tri-fluoromethyl, and mono-, di- and tri-fluoromethoxy.

$R^4$ is $C_1$–$C_6$alkyl, $C_1$–$C_2$haloalkyl, fluoro or chloro; and $R^7$ is hydrogen or $C_1$–$C_6$alkyl.

$R^9$ represents from 0 to 5 substituents independently chosen from hydrogen, halogen, hydroxy, $C_1$–$C_6$alkyl, $C_1$–$C_6$alkoxy, $C_1$–$C_6$haloalkyl, and $C_1$–$C_6$haloalkoxy; and ⁜ represents a single or double bond.

Representative substituted tetrahydroisoquinolines provided herein include, but are not limited to, those specifically described in Examples 1–10. It will be apparent that the specific compounds recited therein are representative only, and are not intended to limit the scope of the present invention. Further, as noted above, all compounds of the present invention may be present as a hydrate, free base or a pharmaceutically acceptable acid addition salt.

Certain substituted tetrahydroisoquinolines provided herein have one or more stereogenic centers. In certain embodiment thereof, such compounds may be enantiomers, and may have an enantiomeric excess of at least 55%. Within further embodiments thereof, such compounds have an enantiomeric excess of at least 60%, 70%, 80%, 85%, 90%, 95%, 98%, or 99%. Certain compounds having one or more stereogenic centers have a enantiomeric excess of at least 99%.

Certain substituted tetrahydroisoquinolines provided herein have two or more stereogenic centers. In certain embodiments thereof, such compounds have a diastereomeric excess of at least 55%. In other embodiments thereof such compounds have a diastereomeric excess of 60%, 70%, 80%, 85%, 90%, 95%, or 98%. Certain compounds having two or more stereogenic centers have a diastereomeric excess of at least 99%.

Substituted tetrahydroisoquinolines provided herein detectably alter (modulate) C5a receptor activity and/or ligand binding, as determined using a standard in vitro C5 receptor-mediated chemotaxis assay (described in Example 13), radioligand binding (described in Example 18), or C5a receptor-mediated calcium mobilization assay (described in Example 20). Preferred compounds exhibit an $IC_{50}$ of about 500 nM or less in such a standard C5a receptor-mediated chemotaxis, radioligand binding, and/or calcium mobilization assay, more preferably an $IC_{50}$ of about 250 nM or less in such an assay, still more preferably an $IC_{50}$ of about 200, 150, 100, 50, 25, 10, or 5 nM or less in such an assay.

Initial characterization of compounds can be conveniently carried out using a C5a receptor binding assay or functional assay, such as set forth in the Examples, and may be expedited by applying such assays in a high throughput screening setting. Additional assays suitable for determining the effects of small molecule compounds on C5a receptor binding and receptor modulatory activity, as well as assays suitable for measuring their effects on C5a-induced neutropenia in vivo, can be found in the published literature, for example in U.S. Pat. No. 5,807,824, which is incorporated herein by reference for its disclosure in this regard in Examples 6–9, columns 19–23, as well as for its discussion of complement and inflammation at columns 1–2. Those of skill in the art will recognize that such assays can be readily adapted to the use of cells or animals of different species as deemed appropriate.

In certain embodiments, preferred compounds have favorable pharmacological properties, including oral bioavailability (such that a sub-lethal or preferably a pharmaceutically acceptable oral dose, preferably less than 2 grams, more preferably of less than or equal to one gram, can provide a detectable in vivo effect such as a reduction of C5a-induced neutropenia), ability to inhibit leukocyte chemotaxis at nanomolar concentrations and preferably at sub-nanomolar concentrations, low toxicity (a preferred compound is non-toxic when a C5a receptor-modulatory amount is administered to a subject), minimal side effects (a preferred compound produces side effects comparable to placebo when a C5a receptor-modulatory amount of the compound is administered to a subject), low serum protein binding, and a suitable in vitro and in vivo half-life (a preferred compound exhibits an in vitro half-life that is equal to an in vivo half-life allowing for Q.I.D. dosing, preferably T.I.D. dosing, more preferably B.I.D. dosing, and most preferably once-a-day dosing). Distribution in the body to sites of complement activity is also desirable (e.g., compounds used to treat CNS disorders will preferably penetrate the blood brain barrier, while low brain levels of compounds used to treat periphereal disorders are typically preferred).

Routine assays that are well known in the art may be used to assess these properties, and identify superior compounds for a particular use. For example, assays used to predict bioavailability include transport across human intestinal cell monolayers, such as Caco-2 cell monolayers. Penetration of the blood brain barrier of a compound in humans may be predicted from the brain levels of the compound in laboratory animals given the compound (e.g., intravenously). Serum protein binding may be predicted from albumin binding assays, such as those described by Oravcová, et al. (1996) *Journal of Chromatography* B 677:1–27. Compound half-life is inversely proportional to the frequency of dosage of a compound required to achieve an effective amount. In vitro half-lives of compounds may be predicted from assays of microsomal half-life as described by Kuhnz and Gieschen (1998) *Drug Metabolism and Disposition* 26:1120–27.

Toxicity and side effects may be assessed using any standard method. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). Toxicity may be also evaluated using the assay detecting an effect on cellular ATP production. Other assays that may be used include bacterial reverse mutation assays, such as an Ames test, as well as standard teratogenicity and tumorogenicity assays. Preferably, administration of compounds provided herein at certain doses (i.e., doses yielding effective in vivo concentrations) does not result in prolongation of heart QT intervals (i.e., as determined by electrocardiography in guinea pigs, minipigs or dogs). When administered daily for five or preferably ten days, such doses also do not cause liver enlargement resulting in an increase of liver to body weight ratio of more than 100%, preferably not more than 75%, and more preferably not more than 50% over matched controls in laboratory rodents (e.g., mice or rats). Such doses also preferably do not cause liver enlargement resulting in an increase of liver to body weight ratio of more than 50%, preferably not more than 25%, and more preferably not more than 10% over matched untreated controls in dogs or other non-rodent mammals.

Certain preferred compounds also do not promote substantial release of liver enzymes (e.g., ALT, LDH or AST) from hepatocytes in vivo. Preferably the above doses do not elevate serum levels of such enzymes by more than 100%, preferably not by more than 75%, and more preferably not by more than 50% over matched untreated controls in vivo in laboratory rodents. Similarly, concentrations (in culture media or other such solutions that are contacted and incubated with cells in vitro) equivalent to two-fold, preferably five-fold, and most preferably ten-fold the minimum in vivo therapeutic concentration do not cause detectable release of any of such liver enzymes from hepatocytes in vitro into culture medium above baseline levels seen in media from untreated cells.

In certain embodiments, preferred compounds exert their receptor-modulatory effects with high specificity. This means that they only bind to, activate, or inhibit the activity of certain receptors other than C5a receptors with affinity constants of greater than 100 nanomolar, preferably greater than 1 micromolar, more preferably greater than 4 micromolar. The invention also includes highly specifc C5a receptor modulatory compounds that exhibit 200-fold greater affinity for the C5a receptor that for other cellular receptors. Such receptors include neurotransmitter receptors such as alpha- or beta-adrenergic receptors, muscarinic receptors (particularly m1, m2 or m3 receptors), dopamine receptors, and metabotropic glutamate receptors; as well as histamine receptors and cytokine receptors (e.g., interleukin receptors, particularly IL-8 receptors). Such receptors may also include $GABA_A$ receptors, bioactive peptide receptors (other than C5a receptors and C3a receptors, including NPY or VIP receptors), neurokinin receptors, bradykinin receptors, and hormone receptors (e.g., CRF receptors, thyrotropin releasing hormone receptors or melanin-concentrating hormone receptors). Compounds that act with high specifity generally exhibit fewer undesirable side effects.

Within certain embodiments, modulators provided herein do not bind detectably to receptors that do not mediate inflammatory responses, such as GABA receptors, MCH receptors, NPY receptors, dopamine receptors, serotonin receptors and VR1 receptors, with high or even moderate affinity. In addition, or alternatively, certain preferred C5a receptor modulators exhibit an affinity for C5a receptor that is substantially higher than for receptors that do not mediate inflammatory responses (e.g., at least five times higher, at least ten times higher or at least 100 times higher). Assays for evaluating binding to receptors that do not mediate inflammatory responses include, for example, those described in U.S. Pat. No. 6,310,212, which is incorporated herein by reference for its disclosure of a GABA$_A$ receptor binding assays in Examples 14, columns 16–17, in U.S. patent application Ser. No. 10/152,189 which is incorporated herein by reference for its disclosure of an MCH receptor binding assay in Example 2, pages 104–105, in U.S. Pat. No. 6,362,186, which is incorporated herein by reference for its disclosure of CRF1 and NPY receptor binding assays in Examples 19, columns 45–46, in U.S. Pat. No. 6,355,644, which is incorporated herein by reference for its disclosure of a dopamine receptor binding assay at column 10, and in U.S. Pat. No. 6,482,611, which is incorporated herein by reference for its disclosure of VR1 receptor binding assays in Examples 4–5, column 14. It will be apparent that the C5a receptor modulators provided herein may, but need not, bind to one or more other receptors known to mediate inflammatory responses, such as C3a receptors and/or A$_3$ receptors.

Certain preferred compounds are C5a receptor antagonists that do not possess significant (e.g., greater than 5%) agonist activity in any of the C5a receptor-mediated functional assays discussed herein. Specifically, this undesired agonist activity can be evaluated, for example, in the GTP binding assay of Example 19, by measuring small molecule mediated GTP binding in the absence of the natural agonist, C5a. Similarly, in a calcium mobilization assay (e.g., that of Example 20) a small molecule compound can be directly assayed for the ability of the compound to stimulate calcium levels in the absence of the natural agonist, C5a. The preferred extent of C5a agonist activity exhibited by compounds provided herein is less than 10%, 5% or 2% of the response elicited by the natural agonist, C5a.

Additionally, preferred C5a receptor modulators do not inhibit or induce microsomal cytochrome P450 enzyme activities, such as CYP1A2 activity, CYP2A6 activity, CYP2C9 activity, CYP2C19 activity, CYP2D6 activity, CYP2E1 activity or CYP3A4 activity. Preferred C5a receptor modulators also do not exhibit cytotoxicity in vitro or in vivo, are not clastogenic (e.g., as determined using a mouse erythrocyte precursor cell micronucleus assay, an Ames micronucleus assay, a spiral micronucleus assay or the like) and do not induce sister chromatid exchange (e.g., in Chinese hamster ovary cells). Also preferred are C5a receptor modulators that inhibit the occurrence of C5a-induced oxidative burst (OB) in inflammatory cells (e.g., neutrophil) as can be conveniently determined using an in vitro neutrophil OB assay.

For detection purposes, compounds provided herein may be isotopically-labeled or radiolabeled. Accordingly, compounds recited in Formula I (or any other formula specifically recited herein) may have one or more atoms replaced by an atom of the same element having an atomic mass or mass number different from the atomic mass or mass number usually found in nature. Examples of isotopes that can be present in compounds provided herein include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl. In addition, substitution with heavy isotopes such as deuterium (i.e., $^2$H) can afford certain therapeutic advantages resulting from greater metabolic stability, for example increased in vivo half-life or reduced dosage requirements and, hence, may be preferred in some circumstances.

Methods of Use

C5a modulators provided herein may be used as agonists or (preferably) antagonists of C5a receptors in a variety of contexts, both in vitro and in vivo. Within certain aspects, C5a antagonists may be used to inhibit the binding of C5a receptor ligand (e.g., C5a) to C5a receptor in vitro or in vivo. In general, such methods comprise the step of contacting a C5a receptor with a sufficient amount of one or more substituted tetrahydroisoquinolines as provided herein, in the presence of C5a receptor ligand in aqueous solution and under conditions otherwise suitable for binding of the ligand to C5a receptor. The C5a receptor may be present in suspension (e.g., in an isolated membrane or cell preparation), or in a cultured or isolated cell. Within certain embodiments, the C5a receptor is expressed by a cell present in a patient, and the aqueous solution is a body fluid. In general, the amount of C5a receptor modulator contacted with the receptor should yield a concentration in the aqueous solution sufficient to inhibit C5a binding to C5a receptor in vitro as measured, for example, using a radioligand binding assay as described in Example 18, a calcium mobilization assay as described in Example 20, or a chemotaxis assay as described in Example 13. Preferably the concentration is sufficient to inhibit chemotaxis of white blood cells in an in vitro chemotaxis assay, so that the levels of chemotaxis observed in a control assay (e.g., one to which a compound provided herein has not been added) are significantly higher (significance here measured as $p \leq 0.05$ using a conventional parametric statistical analysis method such as a student's T-test) than the levels observed in an assay to which a compound as described herein has been added.

Also provided herein are methods for modulating, preferably inhibiting, the signal-transducing activity of a C5a receptor. Such modulation may be achieved by contacting a C5a receptor (either in vitro or in vivo) with an effective amount of one or more C5a receptor modulators provided herein under conditions suitable for binding of the modulator(s) to the receptor. The receptor may be present in solution or suspension, in a cultured or isolated cell preparation or within a patient. Modulation of signal transducing activity may be assessed by detecting an effect on calcium ion conductance (also referred to as calcium mobilization or flux) or by detecting an effect on C5a receptor-mediated cellular chemotaxis. In general, an effective amount of C5a modulator(s) is an amount sufficient to yield a concentration (in an aqueous solution that is in contact with the receptor) that is sufficient to modulate C5a receptor signal transducing activity in vitro within a calcium mobilization assay as described in Example 20 or C5a receptor-mediated cellular chemotaxis within an assay as described in Example 13. C5a receptor modulator(s) provided herein are preferably administered to a patient (e.g., a human) orally or topically, and are present within at least one body fluid of the animal while modulating C5a receptor signal-transducing activity.

The present invention further provides methods for treating patients suffering from conditions responsive to C5a receptor modulation. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to C5a receptor modulation" if modulation of C5a receptor activity results reduction of inappropriate activity of a C5a receptor, regardless of the amount of C5a receptor ligand present locally and/or in alleviation of the condition or a symptom thereof. Patients may include primates (especially humans), domesticated companion animals (such as dogs, cats, horses) and livestock (such as cattle, pigs, sheep), with dosages as described herein.

Conditions that are responsive to C5a receptor modulation include the following:

Autoimmune disorders—e.g., rheumatoid arthritis, systemic lupus erythematosus (and associated glomerulonephritis), psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, and hyperacute rejection of transplanted organs.

Inflammatory disorders and related conditions—e.g., neutropenia, sepsis, septic shock, Alzheimer's disease, stroke, inflammation associated with severe burns, lung injury, and ischemia-reperfusion injury, osteoarthritis, as well as acute (adult) respiratory distress syndrome (ARDS), systemic inflammatory response syndrome (SIRS), and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement) such as extracorporeal post-dialysis syndrome, or in association with contact with other artificial vessel or container surfaces (e.g., ventricular assist devices, artificial heart machines, transfusion tubing, blood storage bags, plasmapheresis, plateletpheresis, and the like).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease.

In a further aspect, C5a receptor modulators may be used to perfuse a donor organ prior to transplantation of the organ into a recipient patient. Such perfusion is preferably carried out using a solution (e.g., pharmaceutical composition) comprising a concentration of the modulator that is sufficient to inhibit C5a receptor-mediated effects in vitro and/or in vivo. Such perfusion preferably reduces the severity or frequency of one or more of the inflammatory sequelae following organ transplantation when compared to that occurring in control (including, without restriction, historical control) transplant recipients who have received transplants of donor organs that have not been so perfused.

Treatment methods provided herein include, in general, administration of an effective amount of one or more compounds provided herein to a patient. Suitable patients include those patients suffering from or susceptible to (i.e., prophylactic treatment) a disorder or disease identified herein. Typical patients for treatment in accordance with the invention include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if a pro-drug) high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

As noted above, compounds and compositions provided herein are useful as inhibitors of C5a receptor-mediated chemotaxis (e.g., they may be used as standards in assays of such chemotaxis). Accordingly, methods are provided herein for inhibiting C5a receptor-mediated cellular chemotaxis, preferably leukocyte (e.g., neutrophil) chemotaxis. Such methods comprise contacting white blood cells (particularly primate white blood cells, especially human white blood cells) with one or more compounds provided herein. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound as described herein has been added.

Within separate aspects, the present invention provides a variety of non-pharmaceutical in vitro and in vivo uses for the compounds provided herein. For example, such compounds may be labeled and used as probes for the detection and localization of C5a receptor (in samples such as cell preparations or tissue sections, preparations or fractions thereof). Compounds may also be used as positive controls in assays for C5a receptor activity, as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use as affinity ligands for immobilizing and thereby isolating, C5a receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

Pharmaceutical Preparations

The present invention also provides pharmaceutical compositions comprising one or more C5a receptor modulators provided herein, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

A carrier is a substance that may be associated with an active compound prior to administration to a patient, often for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

Pharmaceutical compositions may be formulated for any appropriate manner of administration, including, for example, topical, oral, nasal, rectal or parenteral administration. In certain embodiments, compositions in a form suitable for oral use are preferred. Such forms include, for example, pills, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. The term parenteral as used herein includes subcutaneous, intradermal, intravascular (e.g., intravenous), intramuscular, spinal, intracranial, intrathecal and intraperitoneal injection, as well as any similar injection or infusion technique.

Compositions intended for oral use may be prepared according to any method known to the art for the manufacture of pharmaceutical compositions and may contain one or more agents sweetening agents, flavoring agents, coloring agent, and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl or n-propyl p-hydroxybenzoate, one or more coloring agents, one or more flavoring agents, and one or more sweetening agents, such as sucrose or saccharin. Syrups and elixirs may be formulated with sweetening agents, such as glycerol, propylene glycol, sorbitol, or sucrose. Such formulations may also comprise one or more demulcents, preservatives, flavoring agents, and/or coloring agents.

Oily suspensions may be formulated by suspending the active ingredients in a vegetable oil (e.g., arachis oil, olive oil, sesame oil, or coconut oil) or in a mineral oil such as liquid paraffin. The oily suspensions may contain a thickening agent such as beeswax, hard paraffin, or cetyl alcohol. Sweetening agents, such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin), or a mixture thereof. Suitable emulsifying agents include naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate), and condensation products of partial esters derived from fatty acids and hexitol with ethylene oxide (e.g., polyoxyethylene sorbitan monoleate). An emulsion may also comprise one or more sweetening and/or flavoring agents.

The pharmaceutical composition may be prepared as a sterile injectible aqueous or oleaginous suspension in which the modulator, depending on the vehicle and concentration used, is either suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid may be used in the preparation of injectable compositions, and adjuvants such as local anesthetics, preservatives and/or buffering agents can be dissolved in the vehicle.

C5a receptor modulators may also be administered in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal, or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a modulator may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

C5a receptor modulators provided herein are generally administered in an amount that achieves a concentration in a body fluid (e.g., blood, plasma, serum, CSF, synovial fluid, lymph, cellular interstitial fluid, tears or urine) that is sufficient to detectably inhibit the binding of C5a to C5a receptor when assayed in vitro. A dose is considered to be effective if it results in a discernible patient benefit as described herein. Preferred systemic doses range from about 0.1 mg to about 140 mg per kilogram of body weight per day (about 0.5 mg to about 7 g per patient per day), with oral doses generally being about 5–20 fold higher than intravenous doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Pharmaceutical compositions may be packaged for treating conditions responsive to C5a receptor modulation (e.g., rheumatoid arthritis, psoriasis, cardiovascular disease, reperfusion injury, bronchial asthma, Alzheimer's disease, stroke, myocardial infarction, atherosclerosis, ischemic heart disease or ischemia-reperfusion injury). Packaged pharmaceutical compositions may include a container holding a effective amount of at least one C5a receptor modulator as described herein and instructions (e.g., labeling) indicating that the contained composition is to be used for treating a condition responsive to C5a receptor modulation in the patient Preparation of Compounds Substituted tetrahydroisoquinolines provided herein may generally be prepared using standard synthetic methods. In general, starting materials are commercially available from suppliers such as Sigma-Aldrich Corp. (St. Louis, Mo.), or may be synthesized from commercially available precursors using established protocols. By way of example, a synthetic route similar to that shown the following Scheme may be used to prepare 2-(1-aryl-1,2,3,4-tetrahydroisoquinolin-2-yl) acetamides and bicyclics of other ring sizes (n=0, 1, 2, 3, etc), together with synthetic methods known in the art of synthetic organic chemistry, or variations thereon as appreciated by those skilled in the art. Each R, $R^1$, $R^9$ and $R^{10}$ may be any group consistent with the description of the compounds provided herein.

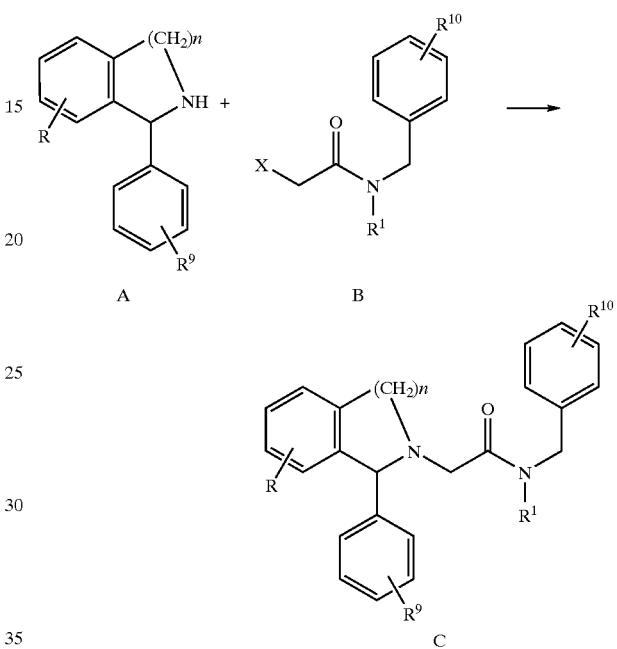

The 2-(1,2,3,4-tetrahydroisoquinolin-2-yl) acetamides of general formula C of the present invention may be prepared according to the procedure described graphically in Scheme 1, wherein a compound of general Formula A, prepared according to literature procedures (e.g., Scully and Schlager (1982) "Synthesis of dihydroisoquinolines and 1-substituted tetrahydroisoquinolines,"*Heterocycles* 19:653–6 or Shinohara et al. (1997) "A highly efficient synthesis of 1-methyl-, 1-benzyl-, and 1-phenyl-1,2,3,4-tetrahydroisoquinolines by a modified Pummerer reaction," *Heterocycles* 46:555–566) is combined (in an appropriate solvent in the presence of an organic or inorganic base) with an appropriately substituted acetamide derivative possessing a leaving group X at its 2 position. For example, X may be halogen, alkyl or aryl sulfonate, or polyfluoroalkylsulfonate. Acetamides of general Formula B may be prepared via condensation of the appropriate secondary amine with a 2-haloacetylhalide (such as 2-chloroacaetyl chloride) in the presence of base. Alternatively acetamides of general formula B can be prepared by condensation of the appropriate secondary amine with either a 2-(alkylsulfonylester)acetic acid or 2-(arylsulfonylester)acetic acid in the presence of an coupling agent such as CDI or the like.

Certain compounds provided herein contain one or more stereogenic centers. In these situations, single enantiomers (i.e., optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

The following Examples are offered by way of illustration and not by way of limitation. Unless otherwise specified all reagents and solvent are of standard commercial grade and are used without further purification, or are readily prepared from such materials by routine methods. Those skilled in the art of organic synthesis will recognize that starting materials and reaction conditions may be varied to achieve the desired end product.

EXAMPLES

Example 1

Synthesis of N-(1-fluorobenzyl)-N-indan-2-yl-2-(6, 7-dimethoxy-1-phenyl-1,2,3,4-tetrahydroisoquinolin-1-yl)acetamide

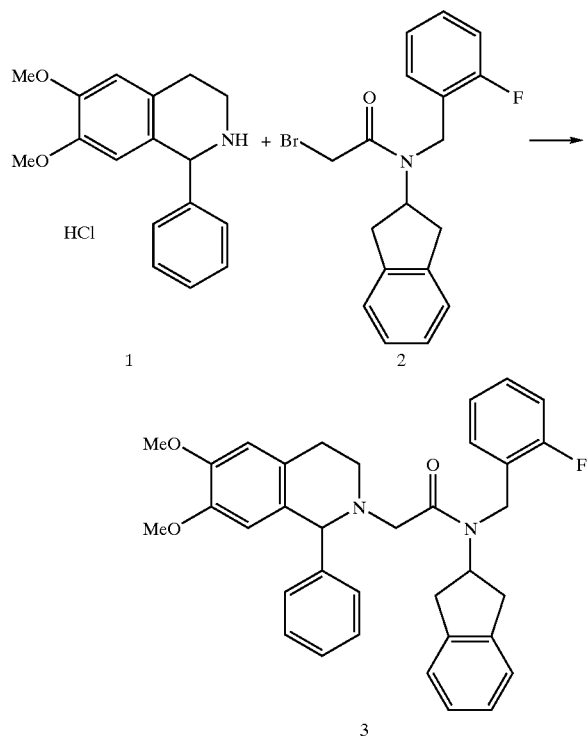

A mixture of 6, 7-dimethoxy-1-phenyl-1,2,3,4-tetrahydroisoquinoline hydrochloride (1, 153 mg, 0.5 mmol), N-(1-fluorobenzyl)-N-indan-2-yl-2-bromoacetamide (2, 180 mg, 0.5 mmol) and potassium carbonate (500 mg) in acetonitrile is heated at 80° C. overnight. After cooling, the mixture is filtered and concentrated. The resulting residue is purified by column chromatography eluting with 5% methanol in chloroform to provide the title product (3) as a thick oil. $^1$H NMR (CDCl$_3$) 6.8–7.3 (m, 14H), 6.60(s, 1H), 6.05 (s, 1H).

Example 2

Preparation of 2-(1-ethyl-1-o-tolyl-3,4-dihydro-1H-isoquinolin-2-yl)-N-(2-fluoro-benzyl)-N-indan-2-yl-acetamide A. 2-Benzyl-1-methyl-1-o-tolyl-1,2,3,4-tetrahydro-isoquinoline

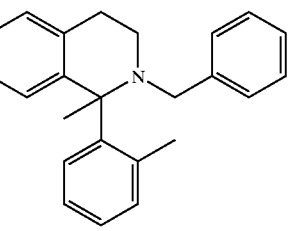

Benzyl bromide (0.43 ml. 3.58 mmol) is added to a solution of 1-o-Tolyl-3,4-dihydro-isoquinoline (755 mg, 3.41 mmol) in acetonitrile (15 ml). The mixture is refluxed for 2 hours, then cooled and concentrated to give the crude isoquinolinium bromide as a yellow foam, which is dissolved in THF (15 ml). Methylmagnesium bromide (1.7 ml of 3M solution in ether, 5.12 mmol) is added slowly and the mixture is stirred for 2 hours at room temperature. The reaction mixture is quenched with saturated NH$_4$Cl and extracted with ethyl acetate. The combined organic layer is washed with brine, dried (Na$_2$SO$_4$), concentrated, and the residue purified by flash chromatography (elution with 5% EtOAc/Hex) to give the desired N-benzyl THIQ as a colorless oil. $^1$H NMR(400 MHz, CDCl$_3$) δ 7.68(d, J=7.2 Hz, 1H), 7.26–6.96 (m, 11H), 6.61 (d, J=8.0 Hz, 1H), 3.67 (d, J=13.2 Hz, 1H), 3.17 (d, J=13.2 Hz, 1H), 3.12–3.03 (m, 1H), 2.92–2.88 (m, 2H), 2.71 (d, J=16 Hz, 1H)2.09 (s, 3H), 1.79 (s, 3H). LSMS 328.6 (MH$^+$).

B. 1-Methyl-1-o-tolyl-1,2,3,4-tetrahydro-isoquinoline

A mixture of 2-Benzyl-1-methyl-1-o-tolyl-1,2,3,4-tetrahydro-isoquinoline (164 mg, 0.50 mmol) and 10% Pd/C (16 mg) in acetic acid (6 ml) is stirred for 5 hours at room temperature under 1 atm of H$_2$. The mixture is filtered through celite and the filtrate concentrated. The residue is diluted with methylene chloride and basified with saturated NaHCO$_3$ to pH 8. The layers are separated and the aqueous layer extracted with methylene chloride. The combined organic layers are washed with brine, dried over sodium sulfate, and concentrated to give 1-Methyl-1-o-tolyl-1,2,3, 4-tetrahydro-isoquinoline. $^1$H NMR (400 MHz, CDCl$_3$) δ 7.62 (d, J=7.2 Hz, 1H), 7.28–6.97 (m, 7H), 6.69 (d, J=8.0 Hz, 1H), 3.43–3.36 (m, 1H), 3.21–3.03 (m, 2H), 2.79 (d, J=16.4 Hz, 1H), 1.99 (s, 3H), 1.91 (s, 3H).

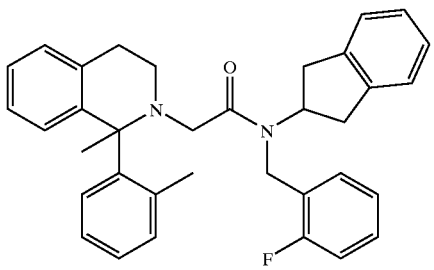

A mixture of 1-Methyl-1-o-tolyl-1,2,3,4-tetrahydro-isoquinoline (96 mg, 0.40 mmol), 2-chloro-N-(2-fluoro-benzyl)-N-indan-2-yl-acetamide (147 mg, 0.40 mmol), and potassium carbonate (111 mg, 0.80 mmol) in actonitrile (10 ml) is heated at reflux for 30 hours. The reaction mixture is cooled, treated with water, and extracted with ethyl acetate. The combined extracts are washed with brine, dried over sodium sulfate and concentrated in vacuo. The residue is purified by preparative thin layer chromatography to give 2-(1-Ethyl-1-o-tolyl-3,4-dihydro-1H-isoquinolin-2-yl)-N-(2-fluoro-benzyl)-N-indan-2-yl-acetamide (Compound 4) as a pale yellow oil. LSMS 519.3 (MH$^+$).

Example 3

Preparation of 2-[1-(2,6-difluoro-phenyl)-3,4-dihydro-1H-isoquinolin-2-yl]-N-(2-fluoro-benzyl)-N-indan-2-yl-acetamide

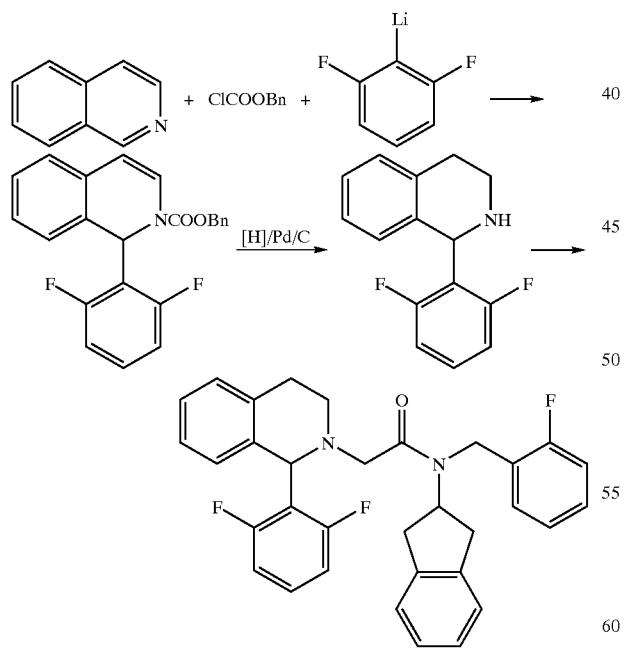

A. 1-(2,6-Difluoro-phenyl)-1H-isoquinoline-2-carboxylic acid benzyl ester

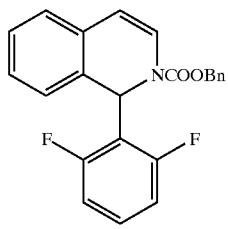

A solution of isoquinoline (645 mg; 5 mmol) in THF (20 mL) is treated with benzyl chloroformate (853 mg; 5 mmol) at 0° C., and the mixture stirred at 0° C. for 1 hour. 2,6-Difluorophenyllithium (prepared from 1-bromo-2,6-difluorobenzene (1.37 g; 7.1 mmol) and n-BuLi (2.5M in hexanes, 2.7 mL; 6.8 mmol at -78° C.) are added to this mixture and the resulting solution stirred at 0° C. for 1 hour and then at room temperature for 2 hours. The reaction is quenched with saturated NH$_4$Cl solution, extracted with ether, dried over anhydrous Na$_2$SO$_4$ and concentrated in vacuo. The residue is purified by flash chromatography over silica gel (elution with hexanes/ether 5;1) to give the product as a colorless oil (0.62 g) LC-MS [MH+] 378.2, RT=3.00 min.

B. 1-(2,6-Difluoro-phenyl)-1,2,3,4-tetrahydro-isoquinoline

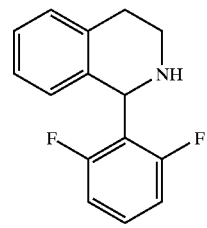

A mixture of 1-(2,6-difluoro-phenyl)-1H-soquinoline-2-carboxylic acid benzyl ester (0.62 g; 1.64 mmol), ethanol/ethyl acetate (10 ml/10 ml), and 10% Pd/C(110 mg) is hydrogenated at room temperature and 50 psi for 19 hours. The mixture is filtered through celite, washed with ethyl acetate, and the filtrate is concentrated in vacuo. The residue is purified by flash chromatography over silica gel (elution with hexane/ethyl acetate 1:1) to give the product as a colorless oil LC-MS [MH+] 246.2, RT=2.00 min.

C. 2-[1-(2,6-Difluoro-phenyl)-3,4-dihydro-1H-isoquinolin-2-yl]-N-(2-fluoro-benzyl)-N-indan-2-yl-acetamide

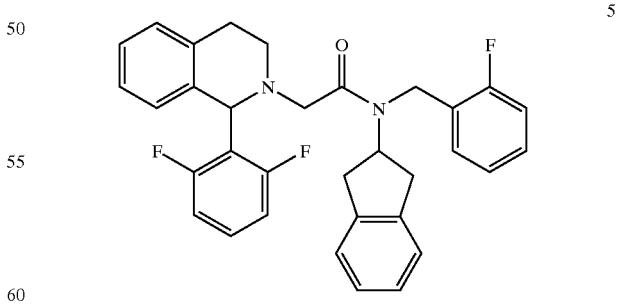

A mixture of 1-(2,6-difluoro-phenyl)-1,2,3,4-tetrahydro-isoquinoline (120 mg; 0.49 mmol), 2-chloro-N-(2-fluoro-benzyl)-N-indan-2-yl-acetamide (260 mg, 0.82 mmol), K$_2$CO$_3$ (500 mg; 3.62 mmol) and acetonitrile (20 mL) is stirred at 80° C. for 20 hours. The mixture is cooled to room temperature, the insolubles are removed by filtration and washed with ethyl acetate, and the filtrate concentrated in vacuo. The residue is purified by flash chromatography over silica gel (elution with hexane/ethyl acetate 5:1) to give the product (Compound 5) as a colorless oil. LC-MS [MH+] 527.21, RT=2.81 min.

Example 4

Preparation of (S)-N-(2-fluoro-benzyl)-N-indan-2-yl-2-(1-o-tolyl-3,4-dihydro-1H-isoquinolin-2-yl)-acetamide A. (S)-(+)-1-o-Tolyl-1,2,3,4-tetrahydroisoquinoline

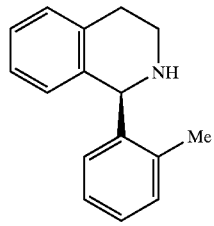

A solution of racemic 1-o-tolyl-1,2,3,4-tetrahydroisoquinoline (14.23 g; 63.7 mmol) in acetone (50 mL) is treated with a hot solution of di-p-toluoyl-L-tartaric acid (23.37 g; 60.5 mmol) in acetone (80 mL). On cooling to room temperature the mixture becomes cloudy. The mixture is stirred overnight at room temperature. The cream suspension is filtered to give the salt as an off-white solid (19 g). This salt is crystallized from isopropyl alcohol/methanol (2:1) to give a white crystalline solid (11.4 g). A small sample is freebased with 1N sodium hydroxide, extracted with ether and evaporated. The residue is dissolved in CDCl$_3$, treated with 3 drops of (S)-□-methylbenzyl isocyanate, and shaken in an n.m.r. tube. The ratio of the o-tolyl methyl peaks in the n.m.r. spectrum indicates a 95% enantiomerically pure product.

The bulk crystalline salt is slurried in ethyl acetate (200 mL), washed with 1N NaOH (2×75 mL) and brine (1×50 ml), dried over magnesium sulfate, and evaporated to give the product as a colorless oil, □$_D$ (c=1.0, CHCl$_3$)=+19. Based on comparison with literature compounds (*J. Org. Chem.* (1999) 6724) this compound is assigned the (S) configuration. The (R)-(−) enantiomer is prepared by an analogous procedure using di-p-toluoyl-D-tartaric acid.

B. (S)-N-(2-Fluoro-benzyl)-N-indan-2-yl-2-(1-o-tolyl-3,4-dihydro-1H-isoquinolin-2-yl)-acetamide

6

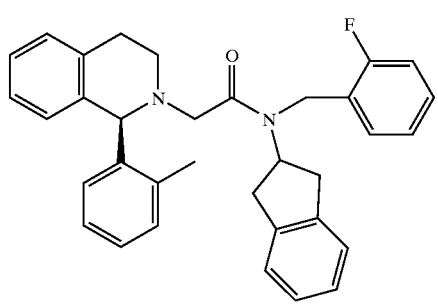

A mixture of (S)-(+)-1-o-tolyl-1,2,3,4-tetrahydroisoquinoline (111 mg; 0.5 mmol), 2-chloro-N-(2-fluoro-benzyl)-N-indan-2-yl-acetamide (158 mg; 0.5 mmol), potassium carbonate (138 mg; 1.0 mmol), and acetonitrile (10 mL) is heated at reflux for 16 hours.

The mixture is cooled to room temperature, treated with water (40 mL), and extracted with ethyl acetate (3×70 ml). The combined extracts are washed with brine (1×30 mL), dried over magnesium sulfate, and concentrated in vacuo. The residue is purified by preparative thin layer chromatography on silica gel (elution with ether:hexane 1:1) to give the product (Compound 6) as a pale yellow foam (164 mg), MS 505.3(MH+).

Example 5

4-(R)-N-(2-fluoro-benzyl)-N-indan-2-yl-2-(4-methyl-1-o-tolyl-3,4-dihydro-1H-isoquinolin-2-yl)-acetamide A. (R)-2-Methyl-N-(2-phenyl-propyl)-benzamide

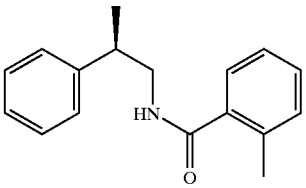

A mixture of (R)-2-phenylpropyl amine (1.24 g; 9.17 mmol), 1N NaOH (20 mL), and dichloromethane (20 mL) is treated with o-toluoyl chloride (1.42 g; 9.17 mmol) added dropwise; the mixture is then stirred at room temperature for 1 hour. The phases are separated and the aqueous layer extracted with dichloromethane (2×70 ml). The combined extracts are washed with water (1×30 mL) and brine (1×30 mL), dried over magnesium sulfate, and evaporated to give the product as a white solid.

B. (R)-4-Methyl-1-o-tolyl-3,4-dihydro-isoquinoline

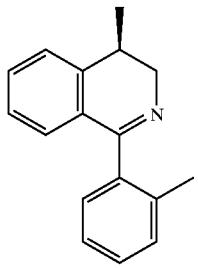

(R)-2-Methyl-N-(2-phenyl-propyl)-benzamide (2.1 g; 8.29 mmol) is added all at once to polyphosphoric acid (pre-heated to 140°) and the resulting mixture is stirred at 140° C. for 1 hour. The mixture is poured onto ice, made basic with concentrated NH$_4$OH, and diluted with dichloromethane (100 mL). The phases are separated, and the aqueous phase extracted with dichloromethane (3×70 mL). The combined organics are washed with water (1×50 mL) and brine (1×50 mL), dried over magnesium sulfate, and evaporated in vacuo. The residue is purified by flash chromatography over silica gel (eluting with ether) to give the product as a yellow oil.

C. 4-(R)-4-Methyl-1-o-tolyl-1,2,3,4-tetrahydro-isoquinoline

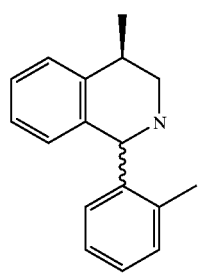

A solution of (R)-4-methyl-1-o-tolyl-3,4-dihydro-isoquinoline (1.01 g; 4.29 mmol) in methanol (40 mL) is treated portionwise with sodium borohydride (487 mg; 12.9 mmol); the mixture is then stirred at room temperature for 6 hours. The methanol is removed under vacuum, and the residue treated with water (40 mL) and extracted with ethyl acetate (3×70 mL). The extracts are washed with water (1×30 mL) and brine (1×30 mL), dried over magnesium sulfate, and evaporated. The residue is purified by flash chromatography over silica gel (elution with ether-hexane (1:1) then ether) to give the product (mixture of diastereoisomers) as a yellow oil.

D. 4-(R)-N-(2-Fluoro-benzyl)-N-indan-2-yl-2-(4-methyl-1-o-tolyl-3,4-dihydro-1H-isoquinolin-2-yl)-acetamide (Compound 7)

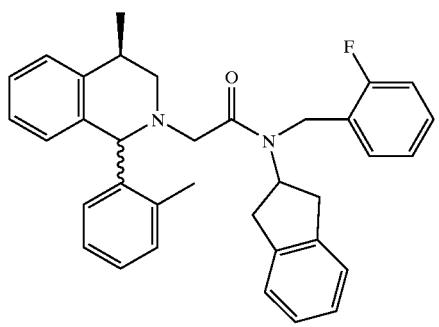

A mixture of 4-(R)-4-methyl-1-o-tolyl-1,2,3,4-tetrahydroisoquinoline (140 mg; 0.59 mmol), 2-chloro-N-(2-fluoro-benzyl)-N-indan-2-yl-acetamide (187 mg; 0.59 mmol), potassium carbonate (163 mg; 1.18 mmol), and acetonitrile (10 mL) is heated at reflux for 5 hr. The mixture is cooled to room temperature, treated with water (50 mL), and extracted with ethyl acetate (3×80 ml). The combined extracts are washed with water (1×50 mL) and brine (1×50 mL), dried over magnesium sulfate, and concentrated in vacuo. The residue is purified by preparative thin layer chromatography on silica gel (elution with ether:hexane 1:3) to give the product (Compound 7), a mixture of diastereoisomers, as a cream foam.

Example 6

1-(R),4-(R)-N-(2-fluoro-benzyl)-N-indan-2-yl-2-(4-methyl-1-o-tolyl-3,4-dihydro-1H-isoquinolin-2-yl)-acetamide A. 1-(R), 4-(R)-4-Methyl-1-o-tolyl-1,2,3,4-tetrahydro-isoquinoline

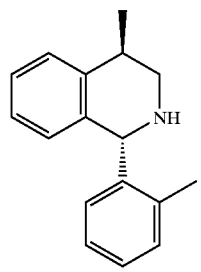

A solution of 4-(R)-4-methyl-1-o-tolyl-1,2,3,4-tetrahydro-isoquinoline (630 mg; 2.65 mmol) in acetone (5 mL) is treated with a warm solution of di-p-toluoyl-L-tartaric acid (973 mg; 2.52 mmol) in acetone (10 mL). After 15 minutes the solution becomes cloudy. The suspension is stirred overnight at room temperature. The mixture is filtered to give a white solid, which is shown by $^1$H nmr to be 77% one isomer. This mixture of isomers is crystallized twice from ethanol to give a white solid (369 mg), shown by $^1$H nmr to be 85% one isomer. This mixture is crystallized from acetone/ethanol (10:1) to give the product as a white solid, shown by $^1$H nmr to be >92% one isomer.

B. 1-(R), 4-(R)- N-(2-Fluoro-benzyl)-N-indan-2-yl-2-(4-methyl-1-o-tolyl-3,4-dihydro-1H-isoquinolin-2-yl)-acetamide (Compound 8)

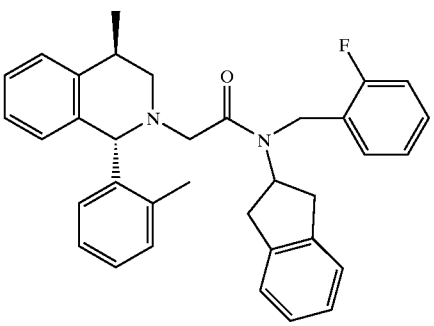

A mixture of 1-(R), 4-(R)-4-methyl-1-o-tolyl-1,2,3,4-tetrahydroisoquinoline di-p-toluoyl-L-tartaric acid salt (218 mg; 0.35 mmol), 2-chloro-N-(2-fluoro-benzyl)-N-indan-2-yl-acetamide (111 mg; 0.35 mmol), potassium carbonate (145 mg; 1.05 mmol), and acetonitrile (10 mL) is heated at reflux for 16 hours. The mixture is cooled to room temperature, treated with water (50 mL), and extracted with ethyl acetate (3×70 ml). The combined extracts are washed with water (1×30 mL) and brine (1×30 mL), dried over magnesium sulfate, and concentrated in vacuo. The residue is purified by preparative thin layer chromatography on silica gel (elution with ether:hexane 1:1) to give the product (Compound 8) as a white foam.

Example 7

Synthesis of N-(2-fluoro-benzyl)-N-indan-2-yl-2-(S)-[1-(S)-o-tolyl-3,4-dihydro-1H-isoquinolin-2-yl]-propionamide A. (R)-(+)-2-bromo-propionic acid tert-butyl ester and (S)-(−)-2-bromo-propionic acid tert-butyl ester

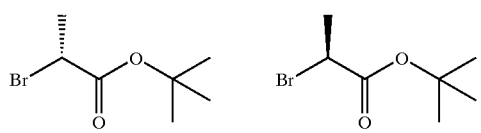

(R)-(+)-2-bromo-propionic acid tert-butyl ester and (S)-(−)-2-bromo-propionic acid tert-butyl ester are both prepared essentially as described by Kozikowski, et. al. (1990) *J. Med. Chem.* 33(16):1561–71.

B. 2-(S)-(1-o-tolyl-3,4-dihydro-1H-isoquinolin-2-yl)-propionic acid tert-butyl ester

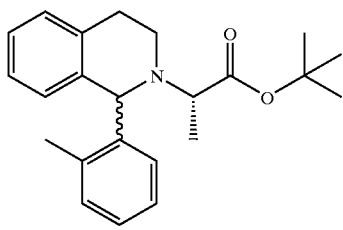

Racemic 1-o-tolyl-3,4-dihydro-1H-isoquinoline (0.67 g, 3.00 mmol) is added to a solution of (R)-(+)-2-bromo-propionic acid tert-butyl ester (0.50 g, 2.39 mmol) in acetonitrile (10 mL) and the mixture was stirred at 85° C. for 16 hours. After cooling to room temperature the reaction is diluted with ethyl acetate (100 mL) and saturated sodium bicarbonate (100 mL) and the organic layer isolated, washed with water (2×100 mL), brine (1×100 mL), and dried over magnesium sulfate. Filtration and concentration are followed by flash chromatography on $SiO_2$ using 40:1 hexane-:ethyl ether to afford 2-(S)-(1-o-tolyl-3,4-dihydro-1H-isoquinolin-2-yl)-propionic acid tert-butyl ester as a colorless syrup.

C. 2-(S)-[1-(S)-o-tolyl-3,4-dihydro-1H-isoquinolin-2-yl]-propionic acid

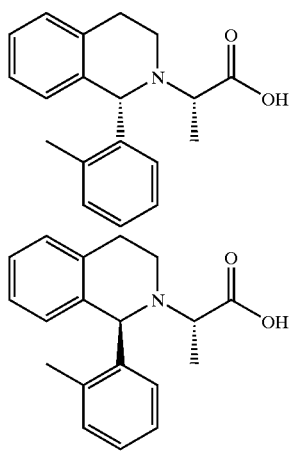

Trifluoroacetic acid (5.0 mL, 64.9 mmol) is added to a solution of 2-(S)-(1-o-tolyl-3,4-dihydro-1H-isoquinolin-2-yl)-propionic acid tert-butyl ester (0.27 g, 0.768 mmol) in dichloromethane (5.0 mL). The reaction mixture is stirred at room temperature for 4 hours. All solvent is removed in vacuo, ethyl ether (50 mL) and saturated sodium bicarbonate (100 mL) are added and the organic layer is removed. The aqueous layer is acidified to pH 2.0 using 1M HCl and the crude product extracted into dichloromethane (100 mL), washed with water (2×50 mL) and brine (1×100 mL), and dried over magnesium sulfate. Filtration and concentration are followed by flash chromatography on $SiO_2$ using 20:1 dichloromethane:methanol and afford 100 mg 2-(S)-[1-(R)-o-tolyl-3,4-dihydro-1H-isoquinolin-2-yl]-propionic acid ($R_f$ of 0.6) and 70 mg 2-(S)-[1-(S)-o-tolyl-3,4-dihydro-1H-isoquinolin-2-yl]-propionic acid ($R_f$ of 0.3) both as white foams. 2-(S)-[1-(R)-o-tolyl-3,4-dihydro-1H-isoquinolin-2-yl]-propionic acid, 2-(R)-[1-(S)-o-tolyl-3,4-dihydro-1H-isoquinolin-2-yl]-propionic acid and 2-(R)-[1-(R)-o-tolyl-3,4-dihydro-1H-isoquinolin-2-yl]-propionic acid are prepared in similar fashion.

D. N-(2-fluoro-benzyl)-N-indan-2-yl-2-(S)-[1-(S)-o-tolyl-3,4-dihydro-1H-isoquinolin-2-yl]-propionamide (Compound 9)

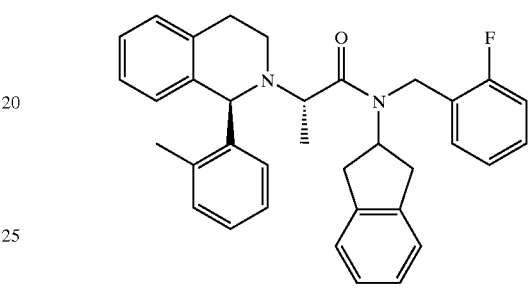

N-methylmorpholine (0.039 mL, 0.355 mmol) and isobutyl chloroformate (0.037 mL, 0.284 mmol) are added to a solution of 2-(S)-[1-(S)-o-tolyl-3,4-dihydro-1H-isoquinolin-2-yl]-propionic acid (70 mg, 0.237 mmol) in tetrahydrofuran (10 mL) at 0° C. The reaction mixture is stirred for 1 hour. N-(2-fluoro-benzyl)-N-indanamine (0.114 g, 0.474 mmol) is then added and the reaction mixture is stirred at room temperature for 16 hours. All solvent is removed in vacuo and saturated sodium bicarbonate (50 mL) and ethyl acetate (50 mL) are added. The organic layer is isolated, washed with water (1×100 mL), brine (1×100 mL), and dried over magnesium sulfate. Filtration and concentration are followed by flash chromatography on $SiO_2$ using 20:1 dichloromethane:methanol to afford 76 mg of N-(2-fluoro-benzyl)-N-indan-2-yl-2-(S)-[1-(S)-o-tolyl-3,4-dihydro-1H-isoquinolin-2-yl]-propionamide (Compound 9) as a colorless oil.

Example 8

4-(2-fluoro-phenyl)-3-indan-2-yl-1-(3-methyl-2-o-tolyl-piperidin-1-yl)-butan-2-one A. 3-Methyl-2-o-tolyl-pyridine

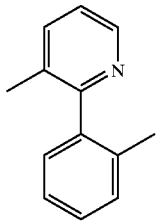

A mixture of 2-bromo-3-methylpyridine (1.09 g; 6.34 mmol), o-tolylboronic acid (1.29 g; 9.50 mmol), and Pd(PPh$_3$)$_4$ (147 mg; 2 mol %) in DME (30 ml) is stirred for 10 minutes at room temperature. Sodium carbonate (32 ml of 1M solution in water; 32 mmol) is added to this mixture and the mixture is heated for 16 hours at 80° C. The reaction mixture is treated with water and extracted with dichloromethane. The combined extracts are washed with brine, dried over sodium sulfate, and concentrated in vacuo. The residue is purified by flash chromatography over silica gel (elution with 20% EtOAc/Hexane) to 3-methyl-2-o-tolyl-pyridine as a yellow oil. $^1$H NMR(300 MHz, CDCl$_3$) δ 8.51(d, 1H), 7.58(d, 1H), 7.27–7.15(m, 5H), 2.14(s, 3H), 2.10(s, 3H).

B. 3-Methyl-2-o-tolyl-piperidine

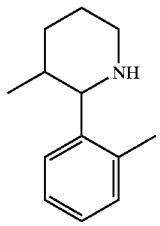

Platinum oxide (44 mg; 5 mol %) is added to a Parr bottle containing 3-methyl-2-o-tolyl-pyridine (176 mg; 3.9 mmol) and concentrated HCl (0.1 ml) in absolute ethanol (30 ml). The Parr bottle is sealed in a mechanical shaker, evacuated, and then purged with nitrogen followed by hydrogen. The system is pressurized to 70 psi of hydrogen at room temperature and mechanical shaking engaged. After 2 days, shaking is stopped, the reaction mixture is filtered through celite, concentrated in vacuo, diluted with ethyl acetate, and treated with 1N NaOH. The mixture is extracted with ether, the combined extracts were washed with brine, dried over sodium sulfate, and concentrated in vacuo to give a mixture of 3-methyl-2-o-tolyl-piperidine and 3-methyl-2-(2-methyl-cyclohexyl)piperidine, which is used directly for the next step.

C. 4-(2-Fluoro-phenyl)-3-indan-2-yl-1-(3-methyl-2-o-tolyl-piperidin-1-yl)-butan-2-one (Compound 10)

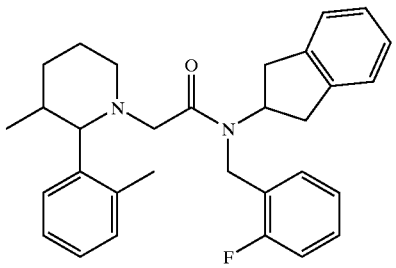

A mixture of 3-methyl-2-o-tolyl-piperidine and 3-methyl-2-(2-methyl-cyclohexyl)-piperidine (330 mg), 2-chloro-N-(2-fluoro-benzyl)-N-indan-2-yl-acetamide (600 mg), and potassium carbonate (520 mg) in acetonitrile (10 ml) is heated at reflux for 16 hours. The reaction mixture is cooled, treated with water, and extracted with ethyl acetate. The combined extracts are washed with brine, dried over sodium sulfate, and concentrated in vacuo. The residue is purified by flash chromatography over silica gel (elution with 5% MeOH/CH$_2$Cl$_2$) to give 4-(2-fluoro-phenyl)-3-indan-2-yl-1-(3-methyl-2-o-tolyl-piperidin-1-yl)-butan-2-one (Compound 10) as a pale yellow oil. LCMS 471.3(MH$^+$).

Example 9

2-(4,5-dimethyl-6-o-tolyl-3,6-dihydro-2H-pyridin-1-yl)-N-(2-fluoro-benzyl)-N-indan-2-yl-acetamide

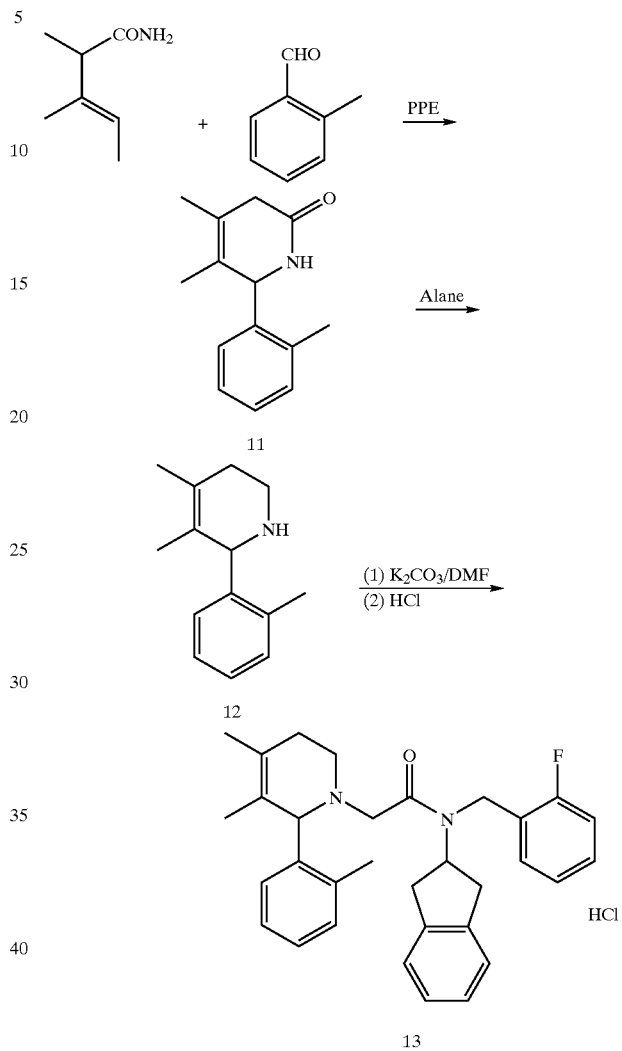

A. 4,5-Dimethyl-6-o-tolyl-3,6-dihydro-1H-pyridin-2-one (11)

4,5-Dimethyl-6-o-tolyl-3,6-dihydro-1H-pyridin-2-one is synthesized essentially as described by *J. Org. Chem.* (1994) 59(2):291.

B. 4,5-Dimethyl-6-o-tolyl-1,2,3,6-tetrahydro-pyridine (12)

A solution of 4,5-dimethyl-6-o-tolyl-3,6-dihydro-1H-pyridin-2-one (177 mg; 0.82 mmol) in THF(5 mL) is treated with alane (10 equivalents) and the mixture is stirred at room temperature for 16 hours. The reaction is quenched with Na$_2$SO$_4$.10H$_2$O (2 g) and the resulting mixture filtered and the insolubles washed with ethyl acetate. The filtrate is concentrated in vacuo to give the product (12).

C. 2-(4,5-Dimethyl-6-o-tolyl-3,6-dihydro-2H-pyridin-1-yl)-N-(2-fluoro-benzyl)-N-indan-2-yl-acetamide (13)

A mixture of 4,5-dimethyl-6-o-tolyl-1,2,3,6-tetrahydro-pyridine (170 mg; 0.85 mmol), 2-chloro-N-(2-fluoro-benzyl)-N-indan-2-yl-acetamide (403 mg; 1.27 mmol) and K$_2$CO$_3$ (587 mg; 4.25 mmol), and acetonitrile (20 ml) is stirred at 80° C. for 20 hours. The reaction mixture is filtered, the insolubles are washed with ethyl acetate, and the filtrate is concentrated in vacuo. The residue is purified by flash chromatography over silica gel (elution with hexanes/ethyl acetate 3:1) to give the product (Compound 13) as an oil. LC-MS [MH+] 483.25, RT=2.69 min.

Example 10

Additional Compounds

Additional compounds of the invention, shown in Table I, are prepared via the method provided in Scheme I and further illustrated in Examples 1–7. Additional compounds of the invention, shown in Table II, are prepared via the methods illustrated in Examples 8–9. Compounds that have an asterisk in the column labeled $Ca^{2+}$, were tested in the standard assay of C5a receptor mediated calcium mobilization given in Example 20 and found to exhibit a Ki of less than 1 uM.

The LC/MS data presented in Tables I and II were obtained using the following instrumentation and methods. MS spectroscopy data is Electrospray MS, obtained in positive ion mode, with a 15V Cone voltage, using a WATERS ZMD 2000 Mass Spec Detector, equipped with a WATERS 600 pump, WATERS 2487 Dual Wavelength Detector, GILSON 215 Autosampler, and a GILSON 841 Microinjector. MassLynx version 3.4 software was used for data collection and analysis.

Sample, 2–20 microliters, was injected onto a 33×4.6 mm YMC ProPack C18; 5 micron column, and eluted using a 2-phase linear gradient at a 4 mL/minute flow rate. Sample was detected at 220 and 254 nm. The elution conditions were as follows: Mobile Phase A-95/5/0.1 Water/Methanol/TFA, Mobile Phase B: 5/95/0.1 Water/Methanol/TFA.

| Gradient time (min) | % B |
|---|---|
| 0 | 10 |
| 2.0 | 100 |
| 3.5 | 100 |
| 3.51 | 10 |

The total run time for the gradient was 4.0 minutes.

TABLE I

| CMP | STRUCTURE | Ca2+ | IUPAC NAME | MS |
|---|---|---|---|---|
| 14 | 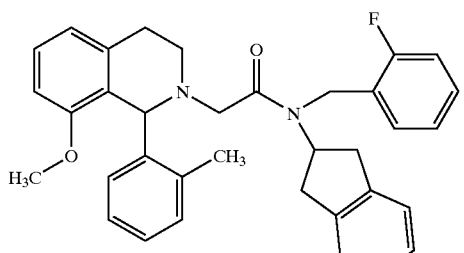 | * | N-(indan-2-yl)-N-(2-fluorobenzyl)-2-[8-methoxy-1-(2-methylphenyl)-3,4-dihydroisoquinolin-2(1H)-yl]acetamide | MH+ 535.4 |
| 15 | 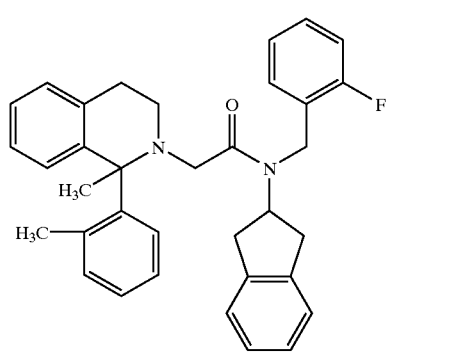 |   | N-(indan-2-yl)-N-(2-fluorobenzyl)-2-[1-methyl-1-(2-methylphenyl)-3,4-dihydroisoquinolin-2(1H)-yl]acetamide | MH+ 519.3 |
| 16 | 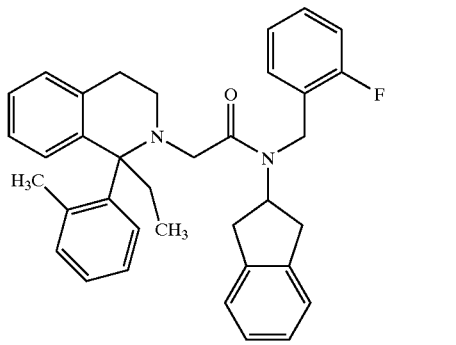 | * | N-(indan-2-yl)-2-[1-ethyl-1-(2-methylphenyl)-3,4-dihydroisoquinolin-2(1H)-yl]-N-(2-fluorobenzyl)acetamide | MH+ 533.3 |

TABLE I-continued

| CMP | STRUCTURE | Ca2+ | IUPAC NAME | MS |
|---|---|---|---|---|
| 17 | 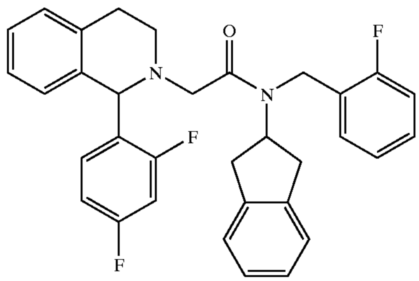 | | 2-[1-(2,4-difluorophenyl)-3,4-dihydroisoquinolin-2(1H)-yl]-N-(indan-2-yl)-N-(2-fluorobenzyl)acetamide | MH+ 527.1 |
| 18 | 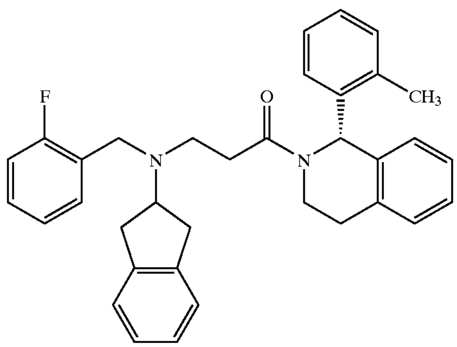 | | N-(2-fluorobenzyl)-N-{3-[1-(2-methylphenyl)-3,4-dihydroisoquinolin-2(1H)-yl]-3-oxopropyl}indan-2-amine | MH+ 519.3 |
| 19 | 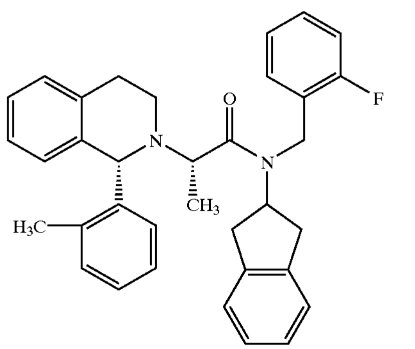 | * | N-(indan-2-yl)-N-(2-fluorobenzyl)-2-[1-(2-methylphenyl)-3,4-dihydroisoquinolin-2(1H)-yl]propanamide | MH+ 519.3 |
| 20 | 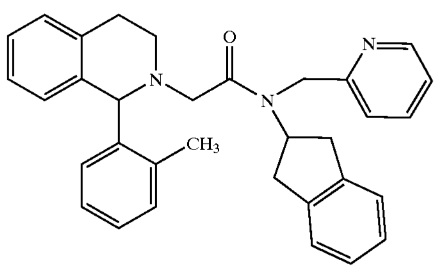 | | N-(indan-2-yl)-2-[1-(2-methylphenyl)-3,4-dihydroisoquinolin-2(1H)-yl]-N-(pyridin-2-ylmethyl)acetamide | MH+ 488.3 |
| 21 | 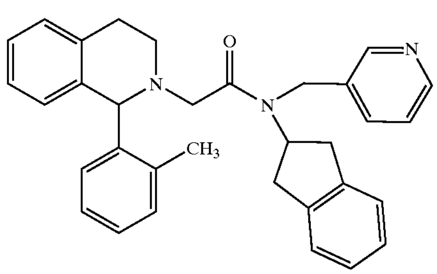 | | N-(indan-2-yl)-2-[1-(2-methylphenyl)-3,4-dihydroisoquinolin-2(1H)-yl]-N-(pyridin-3-ylmethyl)acetamide | MH+ 488.3 |

TABLE I-continued

| CMP | STRUCTURE | Ca2+ | IUPAC NAME | MS |
|---|---|---|---|---|
| 22 | 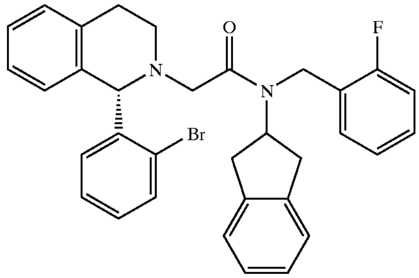 | * | 2-[1-(2-bromophenyl)-3,4-dihydroisoquinolin-2(1H)-yl]-N-(indan-2-yl)-N-(2-fluorobenzyl)acetamide | MH+ 570.9 |
| 23 | 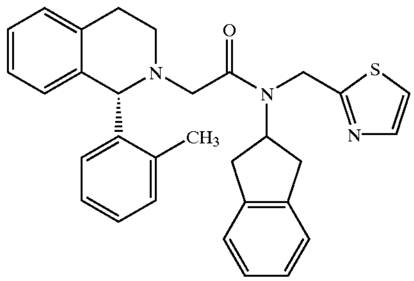 | | N-(indan-2-yl)-2-[1-(2-methylphenyl)-3,4-dihydroisoquinolin-2(1H)-yl]-N-(1,3-thiazol-2-ylmethyl)acetamide | MH+ 494.3 |
| 24 | 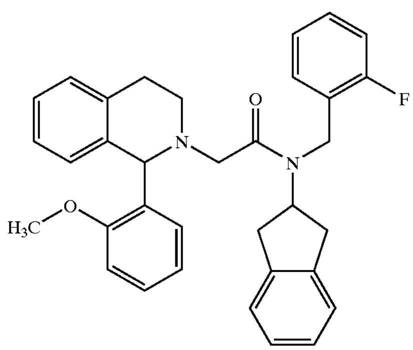 | * | N-(indan-2-yl)-N-(2-fluorobenzyl)-2-[1-(2-methoxyphenyl)-3,4-dihydroisoquinolin-2(1H)-yl]acetamide | MH+ 521.3 |
| 25 | 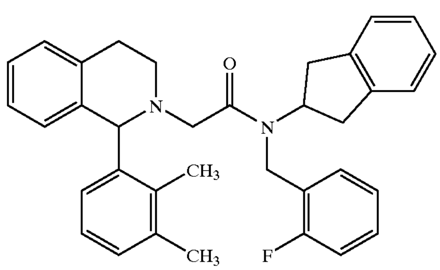 | * | N-(indan-2-yl)-2-[1-(2,3-dimethylphenyl)-3,4-dihydroisoquinolin-2(1H)-yl]-N-(2-fluorobenzyl)acetamide | MH+ 520.2 |
| 26 | 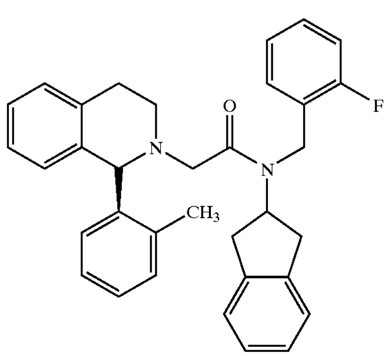 | * | N-(indan-2-yl)-N-(2-fluorobenzyl)-2-[(1R)-1-(2-methylphenyl)-3,4-dihydroisoquinolin-2(1H)-yl]acetamide | MH+ 505.3 |

TABLE I-continued

| CMP | STRUCTURE | Ca2+ | IUPAC NAME | MS |
|---|---|---|---|---|
| 27 | 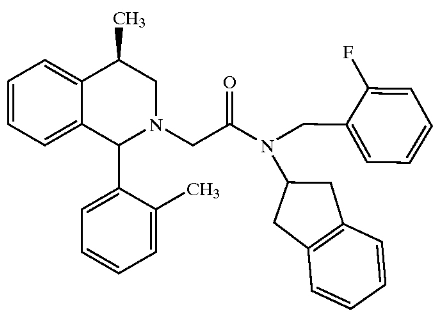 | * | N-(indan-2-yl)-N-(2-fluorobenzyl)-2-[(4R)-4-methyl-1-(2-methylphenyl)-3,4-dihydroisoquinolin-2(1H)-yl]acetamide | MH+ 519.3 |
| 28 | Chiral | * | N-(indan-2-yl)-N-(2-fluorobenzyl)-2-[(1S)-1-(2-methylphenyl)-3,4-dihydroisoquinolin-2(1H)-yl]acetamide | MH+ 505.3 |
| 29 | 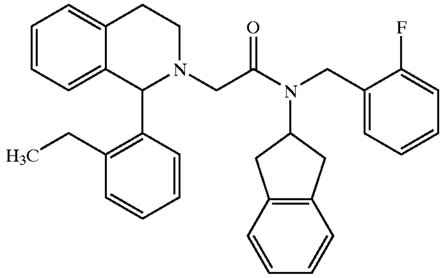 | * | N-(indan-2-yl)-2-[1-(2-ethylphenyl)-3,4-dihydroisoquinolin-2(1H)-yl]-N-(2-fluorobenzyl)acetamide | MH+ 519.3 |
| 30 | 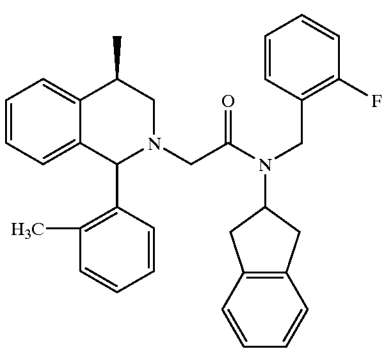 | * | N-(2-Fluoro-benzyl)-N-indan-2-yl-2-(4-methyl-1-o-tolyl-3,4-dihydro-1H-isoquinolin-2-yl)-acetamide | |
| 31 | 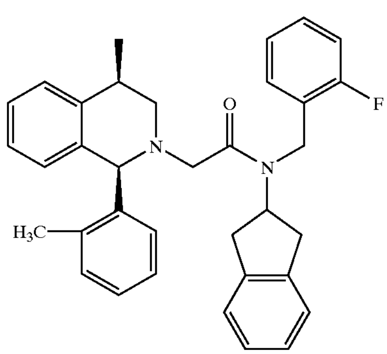 | | N-(indan-2-yl)-N-(2-fluorobenzyl)-2-[(1R,4S)-4-methyl-1-(2-methylphenyl)-3,4-dihydroisoquinolin-2(1H)-yl]acetamide | |

TABLE I-continued

| CMP | STRUCTURE | Ca2+ | IUPAC NAME | MS |
|---|---|---|---|---|
| 32 | 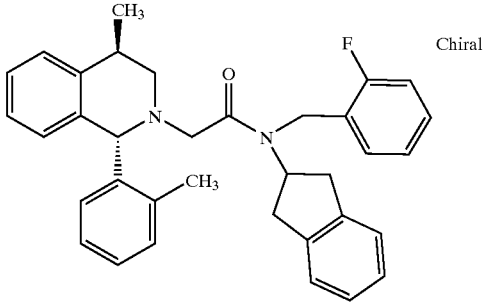 Chiral | | N-(indan-2-yl)-N-(2-fluorobenzyl)-2-[(1S,4S)-4-methyl-1-(2-methylphenyl)-3,4-dihydroisoquinolin-2(1H)-yl]acetamide | MH+ 519.3 |
| 33 | 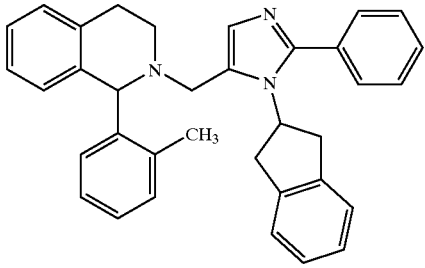 | * | 2-{[1-(indan-2-yl)-2-phenyl-1H-imidazol-5-yl]methyl}-1-(2-methylphenyl)-1,2,3,4-tetrahydroisoquinoline | MH+ 496.3 |
| 34 | 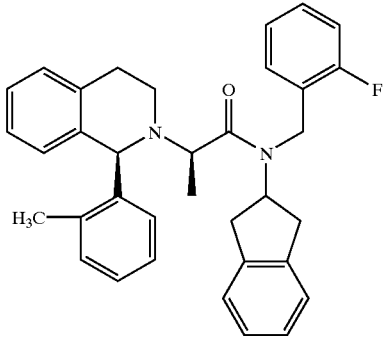 | * | (2S)-N-(indan-2-yl)-N-(2-fluorobenzyl)-2-[(1R)-1-(2-methylphenyl)-3,4-dihydroisoquinolin-2(1H)-yl]propanamide | MH+ 519.3 |
| 35 | 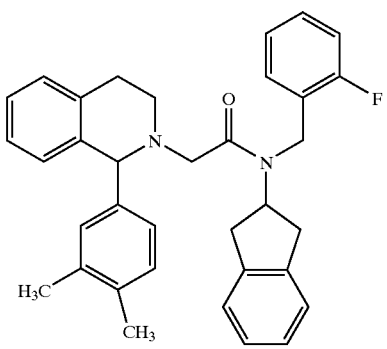 | * | N-(indan-2-yl)-2-[1-(3,4-dimethylphenyl)-3,4-dihydroisoquinolin-2(1H)-yl]-N-(2-fluorobenzyl)acetamide | MH+ 520.2 |

TABLE I-continued

| CMP | STRUCTURE | Ca2+ | IUPAC NAME | MS |
|---|---|---|---|---|
| 36 | 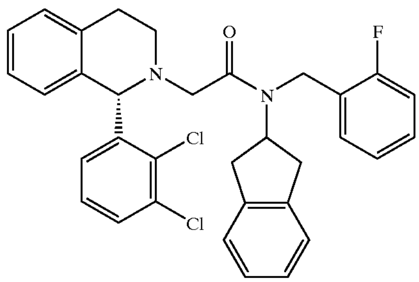 | * | 2-[1-(2,3-dichlorophenyl)-3,4-dihydroisoquinolin-2(1H)-yl]-N-(indan-2-yl)-N-(2-fluorobenzyl)acetamide | MH+ 560.9 |
| 37 | 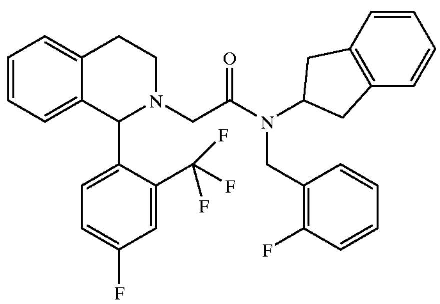 | * | N-(indan-2-yl)-N-(2-fluorobenzyl)-2-[1-[4-fluoro-2-(trifluoromethyl)phenyl]-3,4-dihydroisoquinolin-2(1H)-yl]acetamide | MH+ 577.2 |
| 38 | 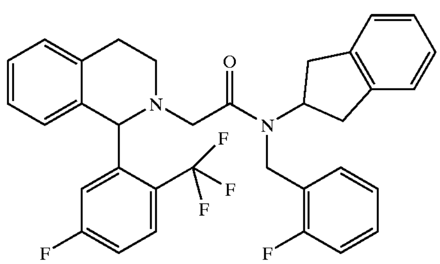 | * | N-(indan-2-yl)-N-(2-fluorobenzyl)-2-[1-[5-fluoro-2-(trifluoromethyl)phenyl]-3,4-dihydroisoquinolin-2(1H)-yl]acetamide | MH+ 577.2 |
| 39 | 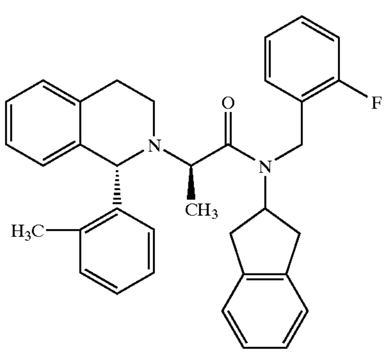 | * | (2S)-N-(indan-2-yl)-N-(2-fluorobenzyl)-2-[(1S)-1-(2-methylphenyl)-3,4-dihydroisoquinolin-2(1H)-yl]propanamide | t = 2.66 min, MH+ = 519.4 |
| 40 | 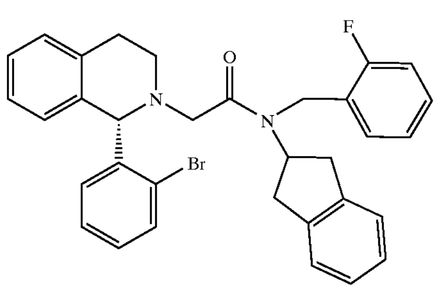 | * | 2-[(1S)-1-(2-bromophenyl)-3,4-dihydroisoquinolin-2(1H)-yl]-N-(indan-2-yl)-N-(2-fluorobenzyl)acetamide | MH+ 569.0, 571.0 |

TABLE I-continued

| CMP | STRUCTURE | Ca2+ | IUPAC NAME | MS |
|---|---|---|---|---|
| 41 | 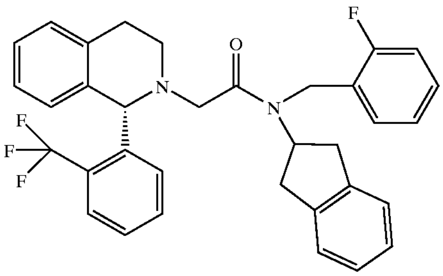 | * | N-(indan-2-yl)-N-(2-fluorobenzyl)-2-[(1S)-1-[2-(trifluoromethyl)phenyl]-3,4-dihydroisoquinolin-2(1H)-yl]acetamide | MH+ 559.3 |
| 42 | 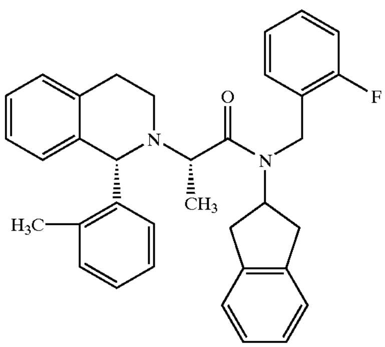 | * | (2S)-N-(indan-2-yl)-N-(2-fluorobenzyl)-2-[(1R)-1-(2-methylphenyl)-3,4-dihydroisoquinolin-2(1H)-yl]propanamide | t = 2.76 min, MH+ = 519.5 |
| 43 | 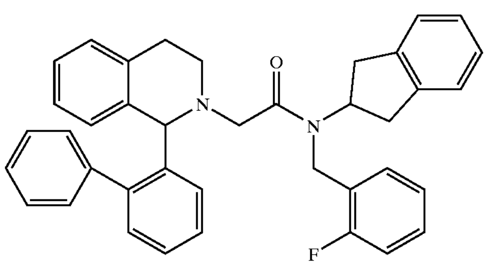 | * | 2-[1-(1,1'-biphenyl-2-yl)-3,4-dihydroisoquinolin-2(1H)-yl]-N-(indan-2-yl)-N-(2-fluorobenzyl)acetamide | t = 1.98 min, MH+ = 567.40 |
| 44 | 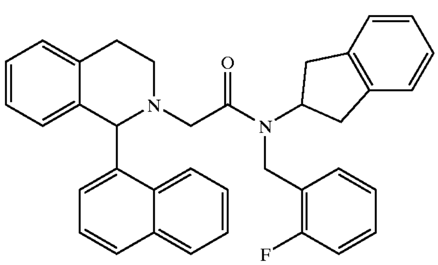 | * | N-(indan-2-yl)-N-(2-fluorobenzyl)-2-[1-(1-naphthyl)-3,4-dihydroisoquinolin-2(1H)-yl]acetamide | t = 1.97 min, MH+ = 541.40 |
| 45 | 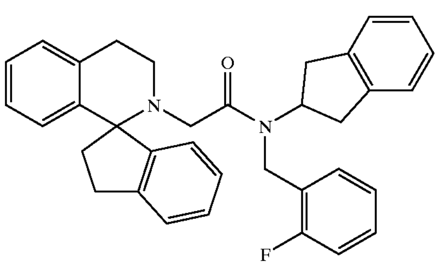 | * | | MH+ 517.4 |

TABLE I-continued

| CMP | STRUCTURE | Ca2+ | IUPAC NAME | MS |
|---|---|---|---|---|
| 46 | Chiral | * | N-(indan-2-yl)-N-(2-fluorobenzyl)-2-[(1R,4R)-4-methyl-1-(2-methylphenyl)-3,4-dihydroisoquinolin-2(1H)-yl]acetamide | t = 2.54 min, MH+ = 519.5 |
| 47 | 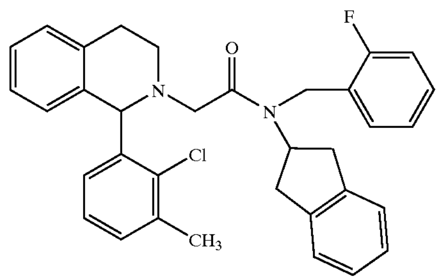 | * | 2-[1-(2-chloro-3-methylphenyl)-3,4-dihydroisoquinolin-2(1H)-yl]-N-(indan-2-yl)-N-(2-fluorobenzyl)acetamide | t = 2.76 min, MH+ = 539.3 |
| 48 | 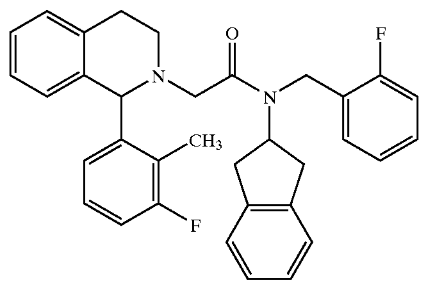 | * | N-(indan-2-yl)-N-(2-fluorobenzyl)-2-[1-(3-fluoro-2-methylphenyl)-3,4-dihydroisoquinolin-2(1H)-yl]acetamide | t = 1.99 min, MH+ = 523.36 |
| 49 | 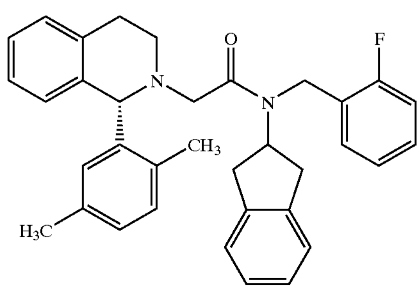 | * | N-(indan-2-yl)-2-[1-(2,5-dimethylphenyl)-3,4-dihydroisoquinolin-2(1H)-yl]-N-(2-fluorobenzyl)acetamide | t = 2.69 min, MH+ = 519.4 |
| 50 | 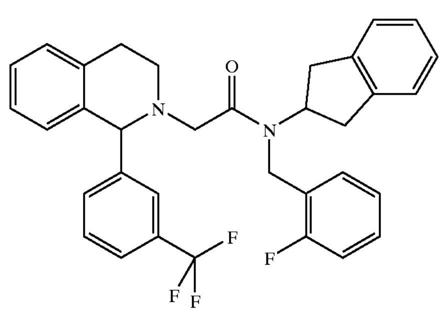 | * | N-(indan-2-yl)-N-(2-fluorobenzyl)-2-[1-[3-(trifluoromethyl)phenyl]-3,4-dihydroisoquinolin-2(1H)-yl]acetamide | t = 2.69 min, MH+ = 559.3 |

TABLE I-continued

| CMP | STRUCTURE | Ca2+ | IUPAC NAME | MS |
|---|---|---|---|---|
| 51 | 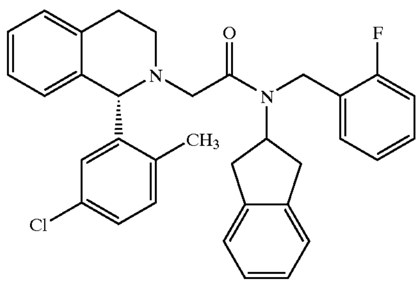 | * | 2-[1-(5-chloro-2-methylphenyl)-3,4-dihydroisoquinolin-2(1H)-yl]-N-(indan-2-yl)-N-(2-fluorobenzyl)acetamide | t = 2.82 min, MH+ = 539.3 |
| 52 | 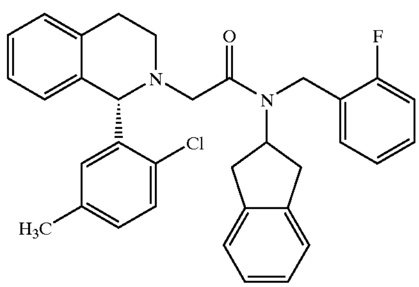 | * | 2-[1-(2-chloro-5-methylphenyl)-3,4-dihydroisoquinolin-2(1H)-yl]-N-(indan-2-yl)-N-(2-fluorobenzyl)acetamide | t = 2.77 min, MH+ = 539.3 |
| 53 | 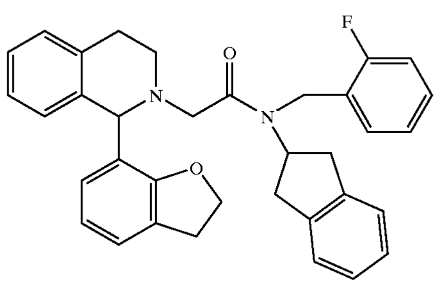 | * | 2-[1-(2,3-dihydro-1-benzofuran-7-yl)-3,4-dihydroisoquinolin-2(1H)-yl]-N-(indan-2-yl)-N-(2-fluorobenzyl)acetamide | t = 2.47 min, MH+ = 533.4 |
| 54 | Chiral | * | N(indan-2-yl)-N-(2-fluorobenzyl)-2-[(1R,4R)-1-(2-fluorophenyl)-4-methyl-3,4-dihydroisoquinolin-2(1H)-yl]acetamide | t = 2.76 min, MH+ = 523.4 |
| 55 | 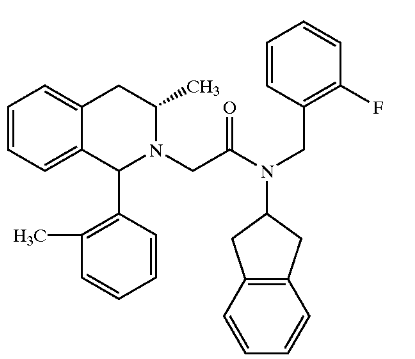 | | N-(indan-2-yl)-N-(2-fluorobenzyl)-2-[(3S)-3-methyl-1-(2-methylphenyl)-3,4-dihydroisoquinolin-2(1H)-yl]acetamide | t = 2.59 min, MH+ = 519.5 |

TABLE I-continued

| CMP | STRUCTURE | Ca2+ | IUPAC NAME | MS |
|---|---|---|---|---|
| 56 | 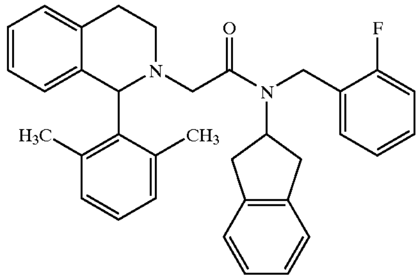 | * | N-(indan-2-yl)-2-[1-(2,6-dimethylphenyl)-3,4-dihydroisoquinolin-2(1H)-yl]-N-(2-fluorobenzyl)acetamide | t = 2.12 min, MH+ = 519.45 |
| 57 | 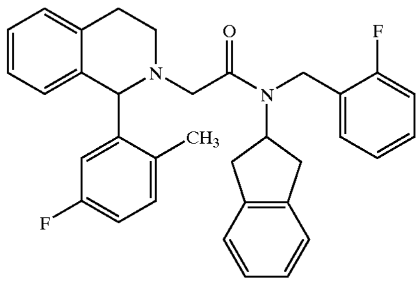 | * | N-(indan-2-yl)-N-(2-fluorobenzyl)-2-[1-(5-fluoro-2-methylphenyl)-3,4-dihydroisoquinolin-2(1H)-yl]acetamide | t = 2.00 min, MH+ = 523.52 |
| 58 | Chiral | * | N-(indan-2-yl)-N-(2-fluorobenzyl)-2-[(1R)-1-(2-fluorophenyl)-3,4-dihydroisoquinolin-2(1H)-yl]acetamide | t = 2.56 min, MH+ = 509.5 |
| 59 | Chiral | * | 2-[(1R,4R)-1-(2-chlorophenyl)-4-methyl-3,4-dihydroisoquinolin-2(1H)-yl]-N-(indan-2-yl)-N-(2-fluorobenzyl)acetamide | t = 2.97 min, MH+ = 539.5 |
| 60 | Chiral | * | (2S)-N-(indan-2-yl)-N-(2-fluorobenzyl)-2-[(1R)-1-(2-fluorophenyl)-3,4-dihydroisoquinolin-2(1H)-yl]propanamide | t = 2.82 min, MH+ = 523.3 |

TABLE I-continued

| CMP | STRUCTURE | Ca2+ | IUPAC NAME | MS |
|---|---|---|---|---|
| 61 | 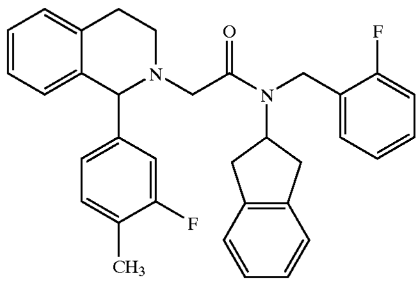 | * | N-(indan-2-yl)-N-(2-fluorobenzyl)-2-[1-(3-fluoro-4-methylphenyl)-3,4-dihydroisoquinolin-2(1H)-yl]acetamide | t = 1.91 min, MH+ = 523.32 |
| 62 | 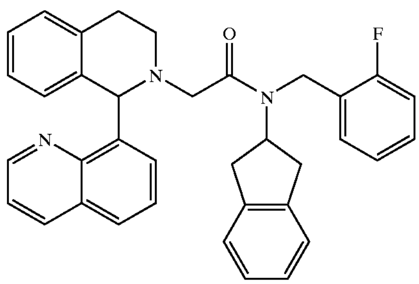 | * | N-(indan-2-yl)-N-(2-fluorobenzyl)-2-(1-quinolin-8-yl-3,4-dihydroisoquinolin-2(1H)-yl)acetamide | t = 1.80 min, MH+ = 542.35 |
| 63 | Chiral | * | (2S)-N-(indan-2-yl)-N-(2-fluorobenzyl)-2-[(1R)-1-(1-naphthyl)-3,4-dihydroisoquinolin-2(1H)-yl]propanamide | t = 2.05 min, MH+ = 555.35 |
| 64 | Chiral | * | (2S)-2-[(1R)-1-(2-chlorophenyl)-3,4-dihydroisoquinolin-2(1H)-yl]-N-(indan-2-yl)-N-(2-fluorobenzyl)propanamide | t = 3.09 min, MH+ = 539.4 |
| 65 | 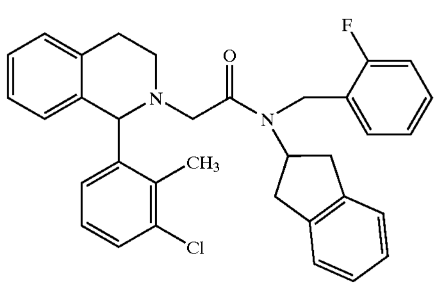 | * | 2-[1-(3-chloro-2-methylphenyl)-3,4-dihydroisoquinolin-2(1H)-yl]-N-(indan-2-yl)-N-(2-fluorobenzyl)acetamide | t = 2.85 min, MH+ = 539.4 |

TABLE I-continued

| CMP | STRUCTURE | Ca2+ | IUPAC NAME | MS |
|---|---|---|---|---|
| 66 | 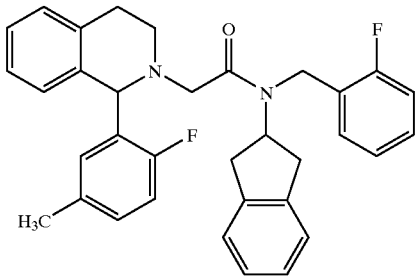 | * | N-(indan-2-yl)-N-(2-fluorobenzyl)-2-[1-(2-fluoro-5-methylphenyl)-3,4-dihydroisoquinolin-2(1H)-yl]acetamide | t = 1.95 min, MH+ = 523.40 |
| 67 | 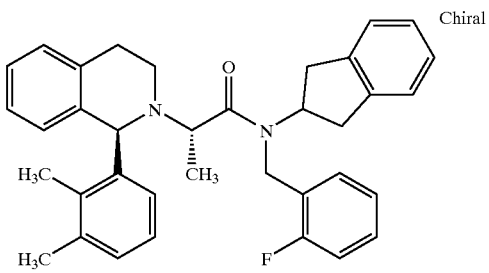 Chiral | * | (2S)-N-(indan-2-yl)-2-[(1R)-1-(2,3-dimethylphenyl)-3,4-dihydroisoquinolin-2(1H)-yl]-N-(2-fluorobenzyl)propanamide | t = 2.79 min, MH+ = 533.5 |
| 68 | 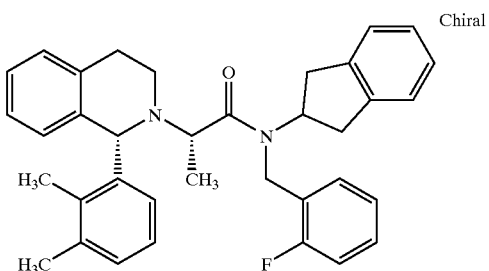 Chiral | * | (2S)-N-(indan-2-yl)-2-[(1S)-1-(2,3-dimethylphenyl)-3,4-dihydroisoquinolin-2(1H)-yl]-N-(2-fluorobenzyl)propanamide | t = 2.70 min, MH+ = 533.4 |
| 69 | 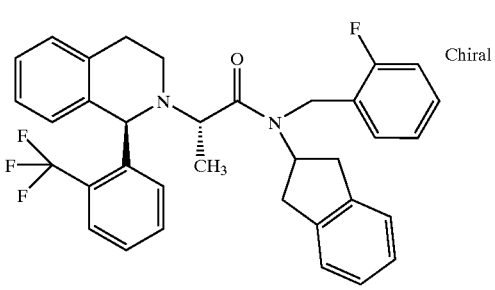 Chiral | * | (2S)-N-(indan-2-yl)-N-(2-fluorobenzyl)-2-[(1R)-1-[2-(trifluoromethyl)phenyl]-3,4-dihydroisoquinolin-2(1H)-yl]propanamide | t = 3.30 min, MH+ = 573.4 |
| 70 | 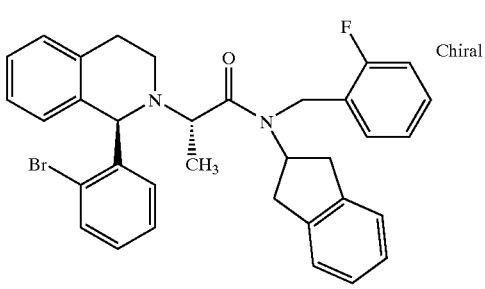 Chiral | * | (2S)-2-[(1R)-1-(2-bromophenyl)-3,4-dihydroisoquinolin-2(1H)-yl]-N-(indan-2-yl)-N-(2-fluorobenzyl)propanamide | t = 3.18 min, MH+ = 583.3, 585.3 |

TABLE I-continued

| CMP | STRUCTURE | Ca2+ | IUPAC NAME | MS |
|---|---|---|---|---|
| 71 | 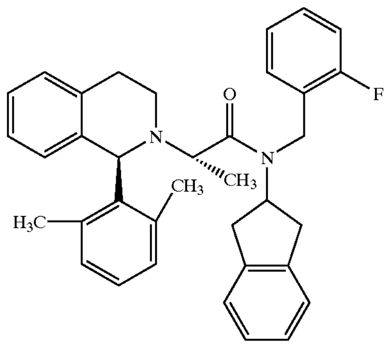 | * | (2S)-N-(indan-2-yl)-2-[(1R)-1-(2,6-dimethylphenyl)-3,4-dihydroisoquinolin-2(1H)-yl]-N-(2-fluorobenzyl)propanamide | t = 2.44 min, MH+ = 533.41 |
| 72 | 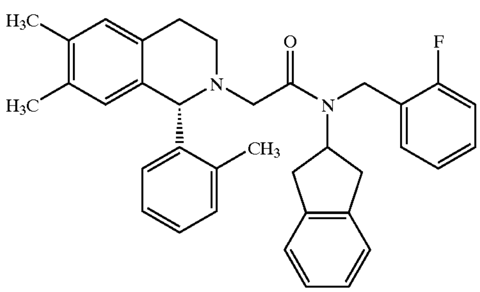 | | N-(indan-2-yl)-2-[6,7-dimethyl-1-(2-methylphenyl)-3,4-dihydroisoquinolin-2(1H)-yl]-N-(2-fluorobenzyl)acetamide | t = 2.70 min, MH+ = 533.4 |
| 73 | 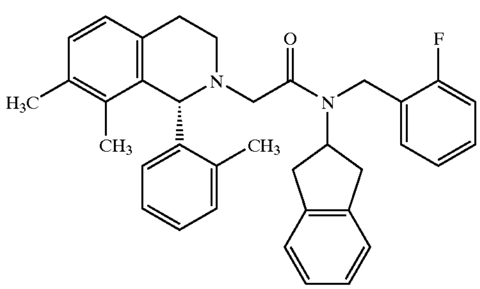 | * | N-(indan-2-yl)-2-[7,8-dimethyl-1-(2-methylphenyl)-3,4-dihydroisoquinolin-2(1H)-yl]-N-(2-fluorobenzyl)acetamide | t = 2.69 min, MH+ = 533.3 |
| 74 | 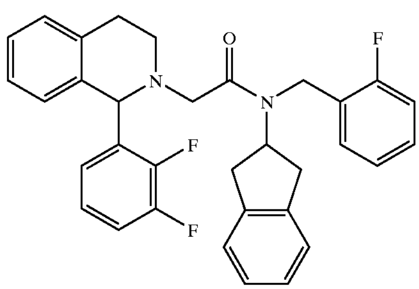 | * | 2-[1-(2,3-difluorophenyl)-3,4-dihydroisoquinolin-2(1H)-yl]-N-(indan-2-yl)-N-(2-fluorobenzyl)acetamide | MH+ = 527.4 |
| 75 | 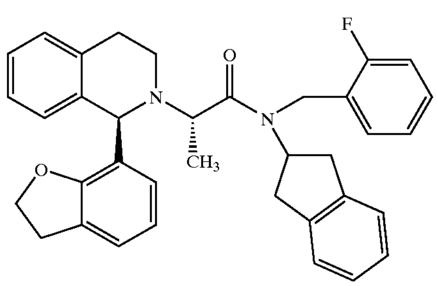 | * | (2S)-2-[(1R)-1-(2,3-dihydro-1-benzofuran-7-yl)-3,4-dihydroisoquinolin-2(1H)-yl]-N-(indan-2-yl)-N-(2-fluorobenzyl)propanamide | t = 2.65 min, MH+ = 547.4 |

TABLE I-continued

| CMP | STRUCTURE | Ca2+ | IUPAC NAME | MS |
|---|---|---|---|---|
| 76 | 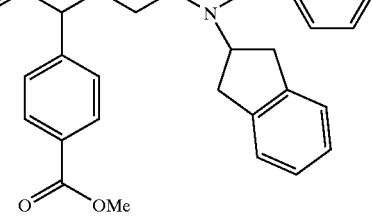 | * | methyl 4-(2-{2-[indan-2-yl(2-fluorobenzyl)amino]-2-oxoethyl}-1,2,3,4-tetrahydroisoquinolin-1-yl)benzoate | |
| 77 | 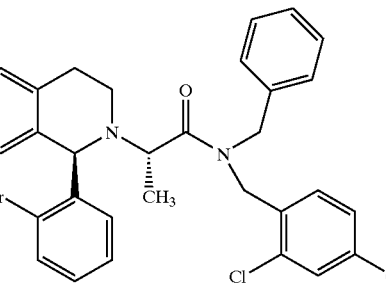 Chiral | * | (2S)-N-benzyl-2-[(1R)-1-(2-bromophenyl)-3,4-dihydroisoquinolin-2(1H)-yl]-N-(2-chloro-4-hydroxybenzyl)propanamide | t = 2.89 min, MH+ = 589.2, 591.2 |
| 78 | 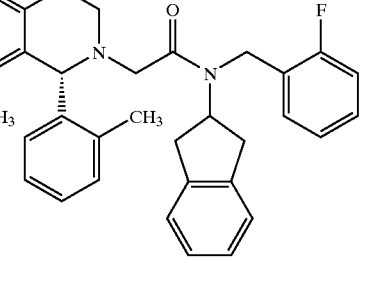 | * | N-(indan-2-yl)-N-(2-fluorobenzyl)-2-[8-methyl-1-(2-methylphenyl)-3,4-dihydroisoquinolin-2(1H)-yl]acetamide | t = 2.72 min, MH+ = 519.3 |
| 79 | 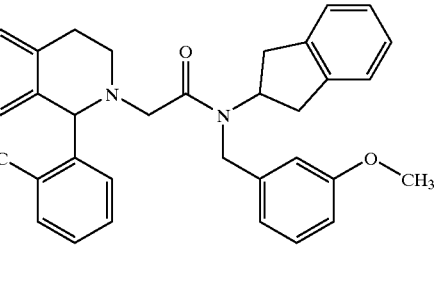 | * | N-(indan-2-yl)-N-(3-methoxybenzyl)-2-[1-(2-methylphenyl)-3,4-dihydroisoquinolin-2(1H)-yl]acetamide | MH+ 517.4 |
| 80 | 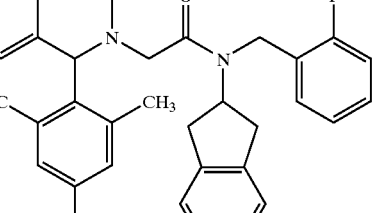 | * | N-(indan-2-yl)-N-(2-fluorobenzyl)-2-(1-mesityl-3,4-dihydroisoquinolin-2(1H)-yl)acetamide | t = 2.95 min, MH+ = 533.34 |

TABLE I-continued

| CMP | STRUCTURE | Ca2+ | IUPAC NAME | MS |
|---|---|---|---|---|
| 81 | 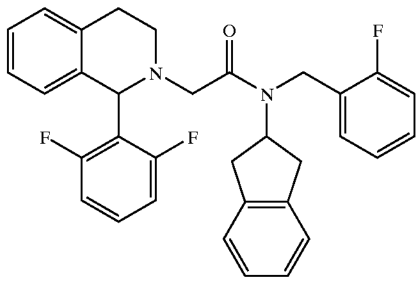 | * | 2-[1-(2,6-difluorophenyl)-3,4-dihydroisoquinolin-2(1H)-yl]-N-(indan-2-yl)-N-(2-fluorobenzyl)acetamide | t = 2.80 min, MH+ = 527.21 |
| 82 | 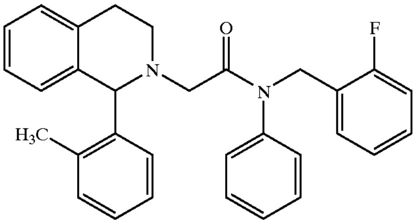 | * | N-(2-fluorobenzyl)-2-[1-(2-methylphenyl)-3,4-dihydroisoquinolin-2(1H)-yl]-N-phenylacetamide | MH+ 465.2 |
| 83 | 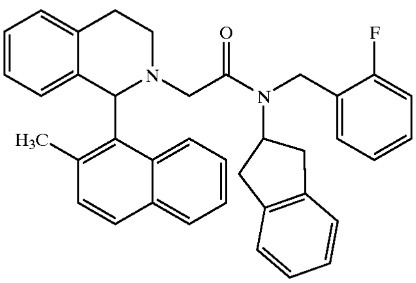 | * | N-(indan-2-yl)-N-(2-fluorobenzyl)-2-[1-(2-methyl-1-naphthyl)-3,4-dihydroisoquinolin-2(1H)-yl]acetamide | t = 2.99 min, MH+ = 555.26 |
| 84 | 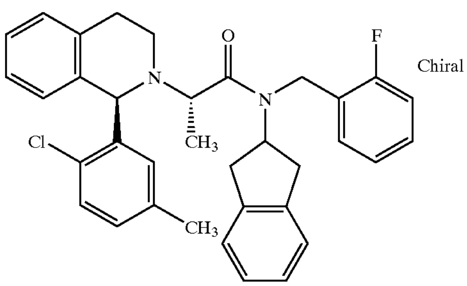 | * | (2S)-2-[(1R)-1-(2-chloro-5-methylphenyl)-3,4-dihydroisoquinolin-2(1H)-yl]-N-(indan-2-yl)-N-(2-fluorobenzyl)propanamide | MH+ = 553.2 |
| 85 | 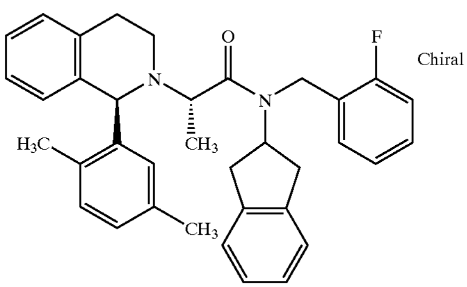 | * | (2S)-N-(indan-2-yl)-2-[(1S)-1-(2,5-dimethylphenyl)-3,4-dihydroisoquinolin-2(1H)-yl]-N-(2-fluorobenzyl)propanamide | t = 2.85 min, MH+ = 533.3 |

TABLE I-continued

| CMP | STRUCTURE | Ca2+ | IUPAC NAME | MS |
|-----|-----------|------|------------|-----|
| 86 | 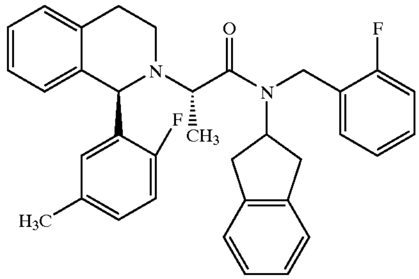 | * | (2S)-N-(indan-2-yl)-N-(2-fluorobenzyl)-2-[(1R)-1-(2-fluoro-5-methylphenyl)-3,4-dihydroisoquinolin-2(1H)-yl]propanamide | t = 2.88 min, MH+ = 537.25 |
| 87 | 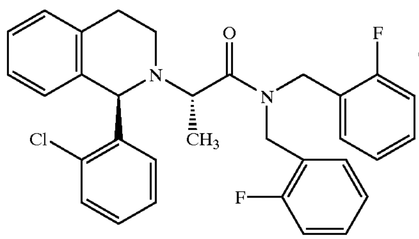 | * | (2S)-2-[(1R)-1-(2-chlorophenyl)-3,4-dihydroisoquinolin-2(1H)-yl]-N,N-bis(2-fluorobenzyl)propanamide | t = 2.99 min, MH+ = 531.2 |
| 88 | 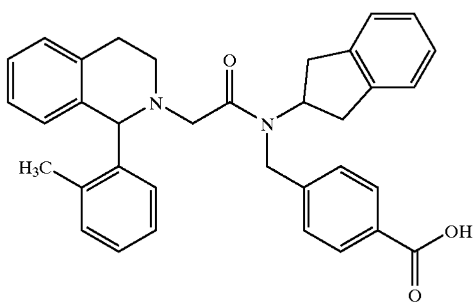 | * | 4-[(indan-2-yl{[1-(2-methylphenyl)-3,4-dihydroisoquinolin-2(1H)-yl]acetyl}amino)methyl]benzoic acid | t = 2.50 min, MH+ = 531.3 |
| 89 | 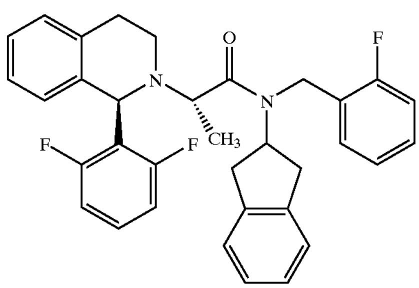 | * | (2S)-2-[(1R)-1(2,6-difluorophenyl)-3,4-dihydroisoquinolin-2(1H)-yl]-N-(indan-2-yl)-N-(2-fluorobenzyl)propanamide | t = 3.17 min, MH+ = 541.30 |
| 90 | 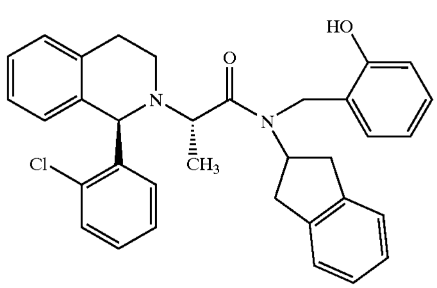 | * | (2S)-2-[(1R)-1-(2-chlorophenyl)-3,4-dihydroisoquinolin-2(1H)-yl]-N-(indan-2-yl)-N-(2-hydroxybenzyl)propanamide | t = 2.93 min, MH+ = 537.3, 539.3 |

TABLE I-continued

| CMP | STRUCTURE | Ca2+ | IUPAC NAME | MS |
|---|---|---|---|---|
| 91 | 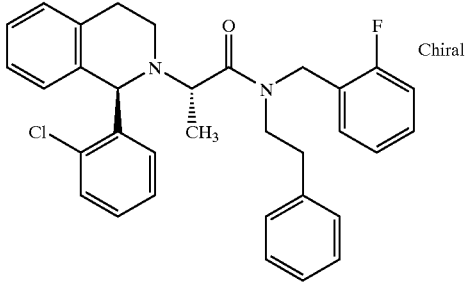 | * | (2S)-2-[(1R)-1-(2-chlorophenyl)-3,4-dihydroisoquinolin-2(1H)-yl]-N-(2-fluorobenzyl)-N-(2-phenylethyl)propanamide | t = 3.02 min, MH+ = 527.2 |
| 92 | 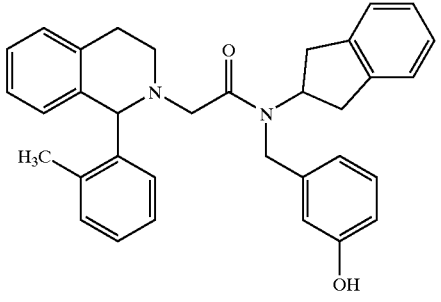 | 23.75 | N-(indan-2-yl)-N-(3-hydroxybenzyl)-2-[1-(2-methylphenyl)-3,4-dihydroisoquinolin-2(1H)-yl]acetamide | t = 2.49 min, MH+ = 503.3 |
| 93 | 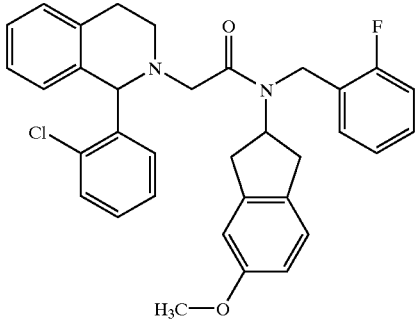 | * | 2-[1-(2-chlorophenyl)-3,4-dihydroisoquinolin-2(1H)-yl]-N-(2-fluorobenzyl)-N-(5-methoxy-indan-2-yl)acetamide | |
| 94 | 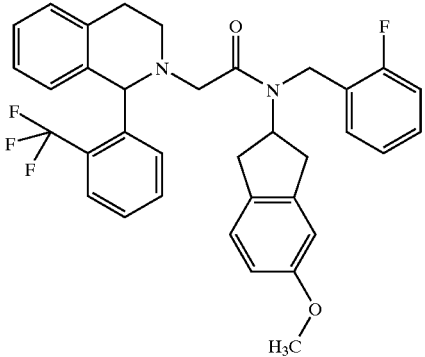 | * | N-(2-fluorobenzyl)-N-(5-methoxy-indan-2-yl)-2-[1-[2-(trifluoromethyl)phenyl]-3,4-dihydroisoquinolin-2(1H)-yl]acetamide | |

TABLE I-continued

| CMP | STRUCTURE | Ca2+ | IUPAC NAME | MS |
|---|---|---|---|---|
| 95 | 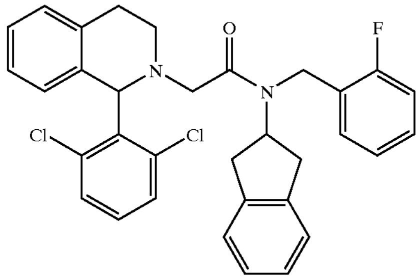 | * | 2-[1-(2,6-dichlorophenyl)-3,4-dihydroisoquinolin-2(1H)-yl]-N-(indan-2-yl)-N-(2-fluorobenzyl)acetamide | t = 3.41 min, MH+ = 559.20 |
| 96 | 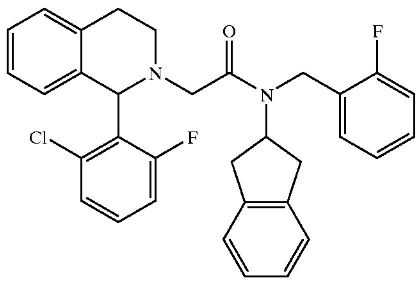 | * | 2-[1-(2-chloro-6-fluorophenyl)-3,4-dihydroisoquinolin-2(1H)-yl]-N-(indan-2-yl)-N-(2-fluorobenzyl)acetamide | t = 3.31 min, MH+ = 543.14 |
| 97 | Chiral | * | (2S)-2-[(1R)-1-(2-chlorophenyl)-3,4-dihydroisoquinolin-2(1H)-yl]-N-(indan-2-yl)-N-(1H-imidazol-4-ylmethyl)propanamide | t = 2.73 min, MH+ = 511.3, 513.3 |
| 98 | Chiral | * | 3{[{(2S)-2-[(1R)-1-(2-chlorophenyl)-3,4-dihydroisoquinolin-2(1H)-yl]propanoyl}(indan-2-yl)amino]methyl}benzoic acid | t = 2.92 min, MH+ = 565.3, 567.3 |
| 99 | 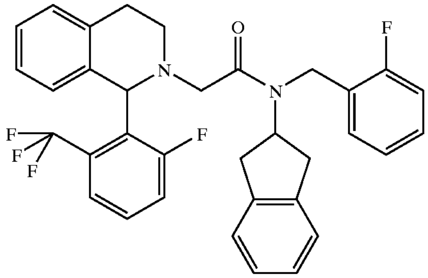 | * | N-(indan-2-yl)-N-(2-fluorobenzyl)-2-[1-[2-fluoro-6-(trifluoromethyl)phenyl]-3,4-dihydroisoquinolin-2(1H)-yl]acetamide | t = 3.04 min, MH+ = 577.18 |

TABLE I-continued

| CMP | STRUCTURE | Ca2+ | IUPAC NAME | MS |
|-----|-----------|------|------------|-----|
| 100 | 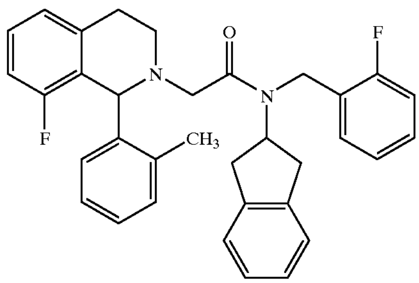 | * | N-(indan-2-yl)-N-(2-fluorobenzyl)-2-[8-fluoro-1-(2-methylphenyl)-3,4-dihydroisoquinolin-2(1H)-yl]acetamide | t = 2.65 min, MH+ = 523.30 |
| 101 | 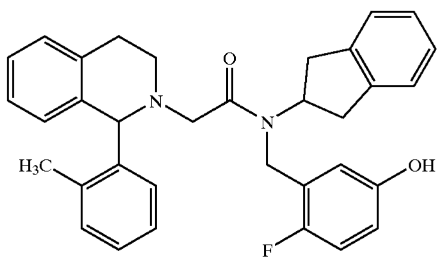 | * | N-(indan-2-yl)-N-(2-fluoro-5-hydroxybenzyl)-2-[1-(2-methylphenyl)-3,4-dihydroisoquinolin-2(1H)-yl]acetamide | t = 2.49 min, MH+ = 521.3 |
| 102 | 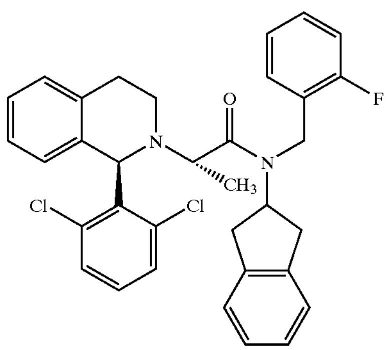 | * | (2S)-2-[(1R)-1-(2,6-dichlorophenyl)-3,4-dihydroisoquinolin-2(1H)-yl]-N-(indan-2-yl)-N-(2-fluorobenzyl)propanamide | t = 3.14 min, MH+ = 573.25 |
| 103 | 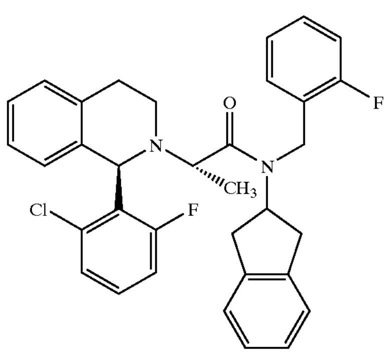 | * | (2S)-2-[(1R)-1-(2-chloro-6-fluorophenyl)-3,4-dihydroisoquinolin-2(1H)-yl]-N-(indan-2-yl)-N-(2-fluorobenzyl)propanamide | t = 3.10 min, MH+ = 557.28 |
| 104 | Chiral | * | (2S)-2-[(1R)-1-(2-chlorophenyl)-3,4-dihydroisoquinolin-2(1H)-yl]-N-[2-(2-fluorophenyl)ethyl]-N-(4-hydroxybenzyl)propanamide | t = 3.10 min, MH+ = 543.1 |

TABLE I-continued

| CMP | STRUCTURE | Ca2+ | IUPAC NAME | MS |
|---|---|---|---|---|
| 105 | 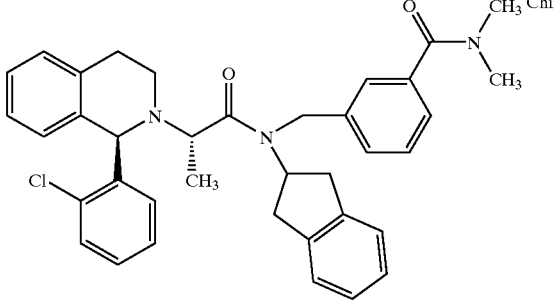 | * | 3-{[{(2S)-2-[(1R)-1-(2-chlorophenyl)-3,4-dihydroisoquinolin-2(1H)-yl]propanoyl}(indan-2-yl)amino]methyl}-N,N-dimethylbenzamide | t = 2.70 min, MH+ = 578.3, 580.3 |
| 106 | 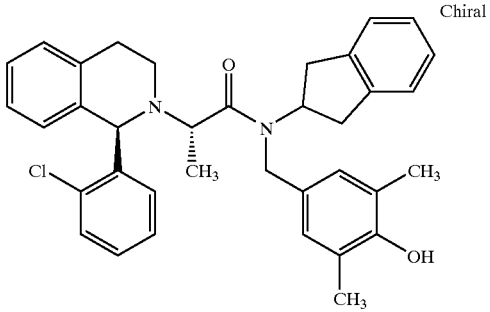 | * | (2S)-2-[(1R)-1-(2-chlorophenyl)-3,4-dihydroisoquinolin-2(1H)-yl]-N-(indan-2-yl)-N-(4-hydroxy-3,5-dimethylbenzyl)propanamide | t = 2.79 min, M+ = 565.3 |
| 107 | 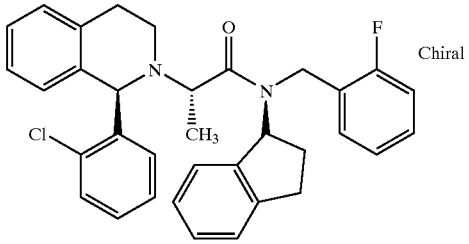 | * | (2S)-2-[(1R)-1-(2-chlorophenyl)-3,4-dihydroisoquinolin-2(1H)-yl]-N-(indan-2-yl)-N-(2-flurorobenzyl)propanamide | t = 2.93 min, MH+ = 539.3 |
| 108 | 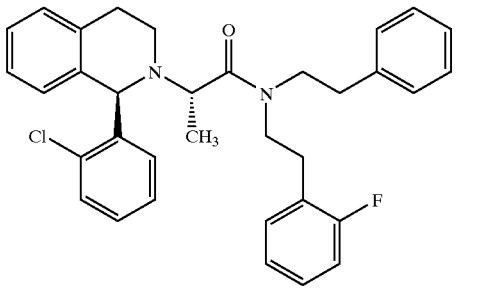 | * | (2S)-2-[(1R)-1-(2-chlorophenyl)-3,4-dihydroisoquinolin-2(1H)-yl]-N-[2-(2-fluorophenyl)ethyl]-N-(2-phenylethyl)propanamide | t = 2.77 min, MH+ = 541.3 |
| 109 | 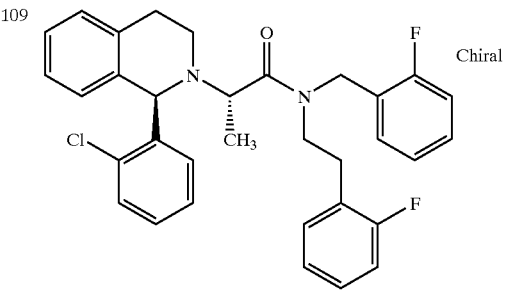 | * | (2S)-2-[(1R)-1-(2-chlorophenyl)-3,4-dihydroisoquinolin-2(1H)-yl]-N-(2-fluorobenzyl)-N-[2-(2-fluorophenyl)ethyl]propanamide | t = 2.79 min, MH+ = 545.2 |

US 6,777,422 B2

TABLE I-continued

| CMP STRUCTURE | Ca2+ | IUPAC NAME | MS |
|---|---|---|---|
| 110 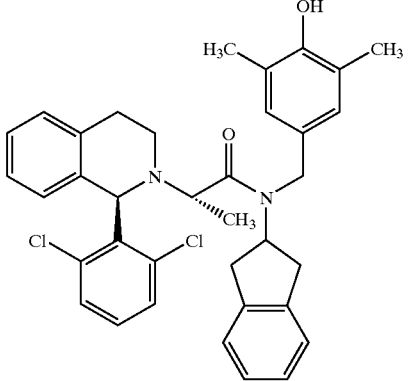 | * | (2S)-2-[(1R)-1-(2,6-dichlorophenyl)-3,4-dihydroisoquinolin-2(1H)-yl]-N-(indan-2-yl)-N-(4-hydroxy-3,5-dimethylbenzyl)propanamide | t = 3.04 min, MH+ = 599.25 |
| 111 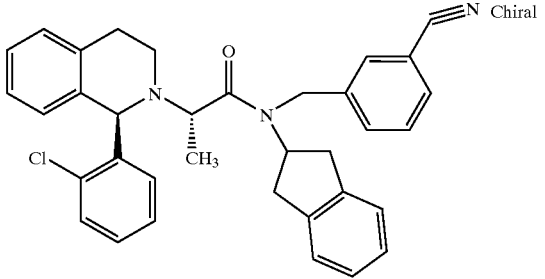 | * | (2S)-2-[(1R)-1-(2-chlorophenyl)-3,4-dihydroisoquinolin-2(1H)-yl]-N-(3-cyanobenzyl)-N-(indan-2-yl)propanamide | t = 2.90 min, MH+ = 546.3, 548.3 |
| 112 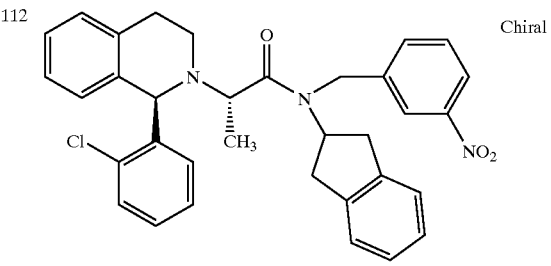 | * | (2S)-2-[(1R)-1-(2-chlorophenyl)-3,4-dihydroisoquinolin-2(1H)-yl]-N-(indan-2-yl)-N-(3-nitrobenzyl)propanamide | t = 2.98 min, MH+ = 566.3, 568.3 |
| 113 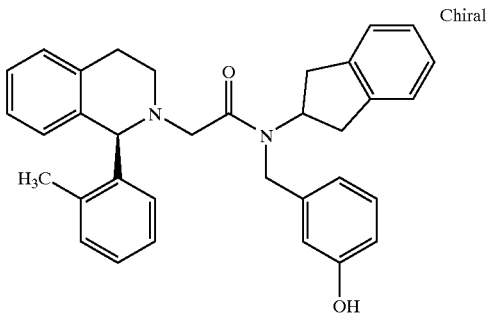 | * | N-(indan-2-yl)-N-(3-hydroxybenzyl)-2-[(1S)-1-(2-methylphenyl)-3,4-dihydroisoquinolin-2(1H)-yl]acetamide | t = 2.40 min, MH+ = 503.3 |

TABLE I-continued

| CMP | STRUCTURE | Ca2+ | IUPAC NAME | MS |
|---|---|---|---|---|
| 114 | Chiral | * | (2S)-2-[(1R)-1-(2-chlorophenyl)-3,4-dihydroisoquinolin-2(1H)-yl]-N-(indan-2-yl)-N-(3-hydroxybenzyl)propanamide | t = 2.72 min, M+ = 537.3 |
| 115 | Chiral | * | (2S)-2-[(1R)-1-(2-chlorophenyl)-3,4-dihydroisoquinolin-2(1H)-yl]-N-(indan-2-yl)-N-(2-fluoro-3-hydroxybenzyl)propanamide | t = 2.85 min, M+ = 555.3 |
| 116 | 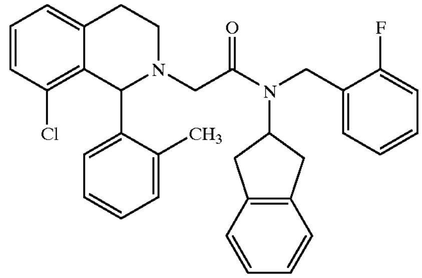 | * | 2-[8-chloro-1-(2-methylphenyl)-3,4-dihydroisoquinolin-2(1H)-yl]-N-(indan-2-yl)-N-(2-fluorobenzyl)acetamide | t = 2.65 min, MH+ = 539.11 |
| 117 | 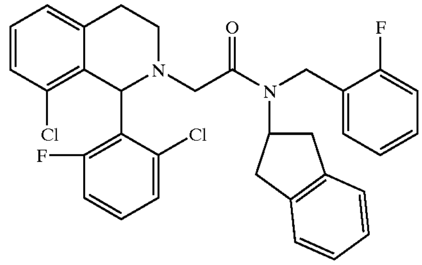 | * | 2-[8-chloro-1-(2-chloro-6-fluorophenyl)-3,4-dihydroisoquinolin-2(1H)-yl]-N-(indan-2-yl)-N-(2-fluorobenzyl)acetamide | t = 3.12 min, MH+ = 577.28 |
| 118 | Chiral | * | (2S)-N-(2-fluorobenzyl)-N-[2-(4-hydroxyphenyl)ethyl]-2-[(1R)-1-(1-naphthyl)-3,4-dihydroisoquinolin-2(1H)-yl]propanamide | t = 2.68 min, MH+ = 559.3 |

TABLE I-continued

| CMP | STRUCTURE | Ca2+ | IUPAC NAME | MS |
|-----|-----------|------|------------|-----|
| 119 | 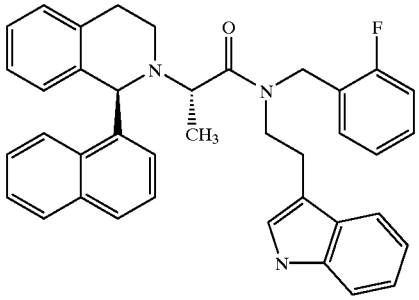 | * | (2S)-N-(2-fluorobenzyl)-N-[2-(1H-indol-3-yl)ethyl]-2-[(1R)-1-(1-naphthyl)-3,4-dihydroisoquinolin-2(1H)-yl]propanamide | t = 2.66 min, MH+ = 582.3 |
| 120 | 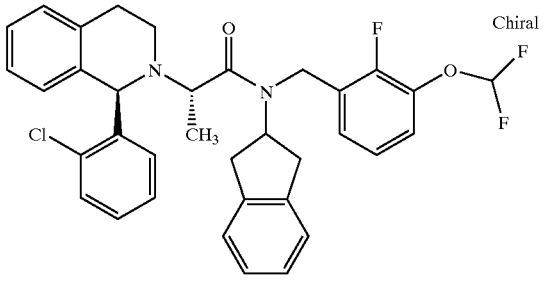 | * | (2S)-2-[(1R)-1-(2-chlorophenyl)-3,4-dihydroisoquinolin-2(1H)-yl]-N-[3-(difluoromethoxy)-2-fluorobenzyl]-N-(indan-2-yl)propanamide | t = 3.19 min, MH+ = 605.2 |
| 121 | 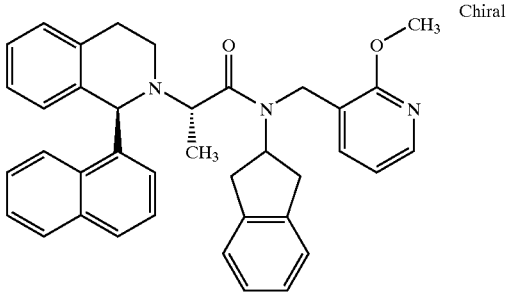 | * | (2S)-N-(indan-2-yl)-N-[(2-methoxypyridin-3-yl)methyl]-2-[(1R)-1-(1-naphthyl)-3,4-dihydroisoquinolin-2(1H)-yl]propanamide | t = 3.28 min, MH+ = 568.5 |
| 122 | 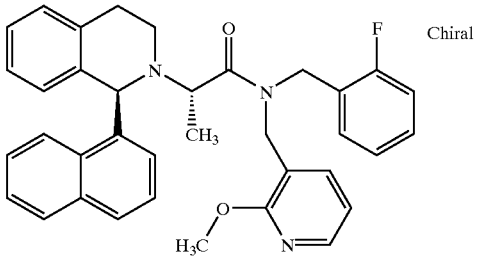 | * | (2S)-N-(2-fluorobenzyl)-N-[(2-methoxypyridin-3-yl)methyl]-2-[(1R)-1-(1-naphthyl)-3,4-dihydroisoquinolin-2(1H)-yl]propanamide | t = 3.11 min, MH+ = 560.5 |
| 123 | 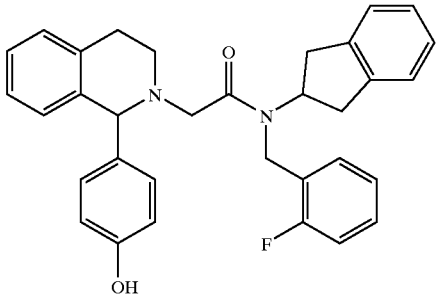 | * | N-(indan-2-yl)-N-(2-fluorobenzyl)-2-[1-(4-hydroxyphenyl)-3,4-dihydroisoquinolin-2(1H)-yl]acetamide | MH+ 507.3 |

TABLE I-continued

| CMP | STRUCTURE | Ca2+ | IUPAC NAME | MS |
|---|---|---|---|---|
| 124 | Chiral | * | (2S)-N-(indan-2-yl)-N-[(6-methoxypyridin-2-yl)methyl]-2-[(1R)-1-(1-naphthyl)-3,4-dihydroisoquinolin-2(1H)-yl]propanamide | t = 3.16 min, MH+ = 568.3 |
| 125 | Chiral | * | (2S)-N-(2-fluorobenzyl)-N-[(6-methoxypyridin-2-yl)methyl]-2-[(1R)-1-(1-naphthyl)-3,4-dihydroisoquinolin-2(1H)-yl]propanamide | t = 3.16 min, MH+ = 560.2 |
| 126 | Chiral | * | (2S)-N-(indan-2-yl)-N-[(3-fluoropyridin-2-yl)methyl]-2-[(1R)-1-(1-naphthyl)-3,4-dihydroisoquinolin-2(1H)-yl]propanamide | t = 3.03 min, MH+ = 556.3 |
| 127 | Chiral | * | (2S)-N-(indan-2-yl)-N-[(5-methoxypyridin-3-yl)methyl]-2-[(1R)-1-(1-naphthyl)-3,4-dihydroisoquinolin-2(1H)-yl]propanamide | t = 3.12 min, MH+ = 568.2 |

TABLE II

| CMP # | STRUCTURE | Ca2+ | MS | Name |
|---|---|---|---|---|
| 128 | 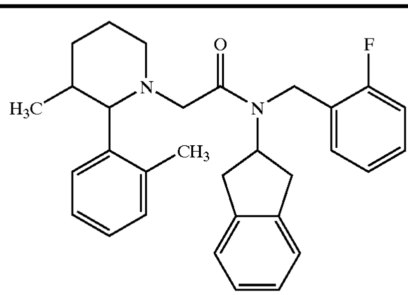 | 546.89 | MH+ 471.3 | N-(2-Fluoro-benzyl)-N-indan-2-yl-2-(3-methyl-2-o-tolyl-piperidin-1-yl)-acetamide |

TABLE II-continued

| CMP # | STRUCTURE | Ca2+ | MS | Name |
|---|---|---|---|---|
| 129 | 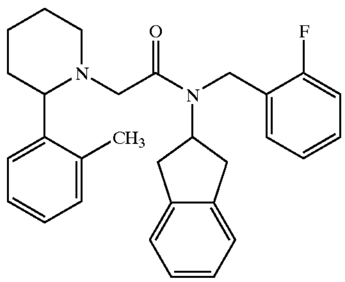 | 131.35 | MH+ 457.3 | N-(2-Fluoro-benzyl)-N-indan-2-yl-2-(2-o-tolyl-piperidin-1-yl)-acetamide |
| 130 | 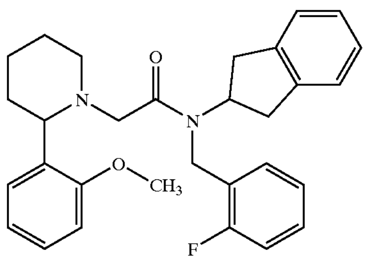 | 404.89 | MH+ 473.2 | N-(2-Fluoro-benzyl)-N-indan-2-yl-2-[2-(2-methoxy-phenyl)-piperidin-1-yl]-acetamide |
| 131 | 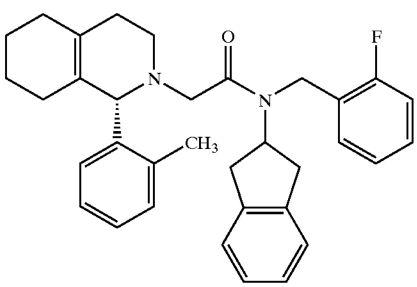 | 13.14 | MH+ 509.5 | N-(2-Fluoro-benzyl)-N-indan-2-yl-2-(1-o-tolyl-3,4,5,6,7,8-hexahydro-1H-isoquinolin-2-yl)-acetamide |
| 132 | 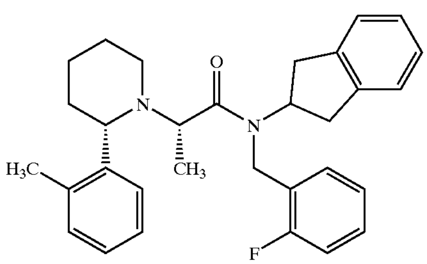 | 114.62 | MH+ 471.5 | N-(2-Fluoro-benzyl)-N-indan-2-yl-2-(2-o-tolyl-piperidin-1-yl)-propionamide |
| 133 | 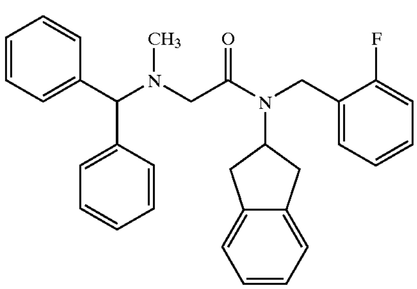 | 464.58 | t = 2.56 min, MH+ 479.3 | 2-(Benzhydryl-methyl-amino)-N-(2-fluoro-benzyl)-N-indan-2-yl-acetamide |

TABLE II-continued

| CMP # | STRUCTURE | Ca2+ | MS | Name |
|---|---|---|---|---|
| 134 | 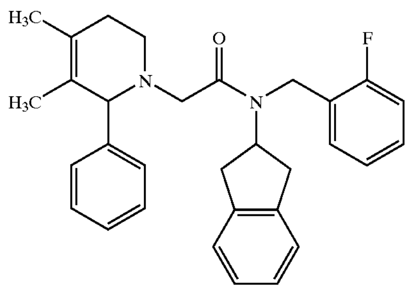 | 575.03 | t = 2.38 min, MH+ 469.27 | 2-(4,5-Dimethyl-6-phenyl-3,6-dihydro-2H-pyridin-1-yl)-N-(2-fluoro-benzyl)-N-indan-2-yl-acetamide |
| 135 | 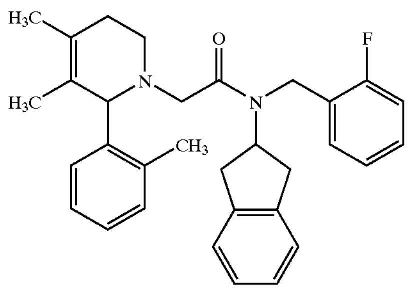 | 193.44 | t = 2.68 min, MH+ 483.25 | 2-(4,5-Dimethyl-6-o-tolyl-3,6-dihydro-2H-pyridin-1-yl)-N-(2-fluoro-benzyl)-N-indan-2-yl-acetamide |
| 136 | 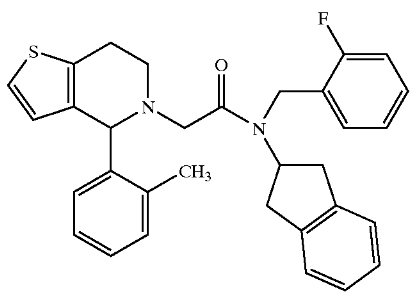 | 39.94 | MH+ = 511.6 | N-(2-Fluoro-benzyl)-N-indan-2-yl-2-(4-o-tolyl-6,7-dihydro-4H-thieno[3,2-c]pyridin-5-yl)-acetamide |

Example 11

Pharmaceutical Preparations of Oral and Intravenous Administration

A. Tablets containing a C5a antagonist and an anti-arthritic agent which is not a C5a receptor antagonist can be prepared as illustrated below:

| Ingredient | Amount |
|---|---|
| C5a receptor antagonist | 5 mg–500 mg |
| C5a receptor-inactive therapeutic agent | 1 mg–500 mg |
| diluent, binder, distigrant, lubricant excipients | q.s. 200–400 mg. |

B. Tablets containing a C5a receptor antagonist as the only active ingredient can be prepared as illustrated below:

| Ingredient | mg | mg |
|---|---|---|
| C5a receptor antagonist | 10 | 50 |
| Microcrystalline Cellulose | 70.4 | 352 |
| Grannular Mannitol | 15.1 | 75.5 |
| Croscarmellose Sodium | 3.0 | 15.0 |
| Colloidal Silicon Dioxide | 0.5 | 2.5 |
| Magnesium Stearate (Impalpable Powder) | 1.0 | 5.0 |
| Total (mg) | 100 | 500 |

C. Tablets containing a C5a receptor antagonist and a C5a receptor inactive agent may be prepared as follows:

| Ingredient | mg | mg |
|---|---|---|
| C5a receptor antagonist | 10 | 25 |
| C5a receptor inactive therapeutic agent | 10 | 25 |
| Microcrystalline Cellulose | 40 | 100 |
| Modified food corn starch | 1.05 | 4.25 |
| Magnesium stearate | 1.25 | 0.5 |

D. Intravenous formulations containing a C5a receptor antagonist and a C5a receptor inactive agent may be prepared as follows:

| Ingredient | Amount |
| --- | --- |
| C5a receptor antagonist | 0.5–10 mg |
| C5a receptor inactive therapeutic agent | 0.5–10 mg |
| Sodium Citrate | 5–50 mg |
| Citric Acid | 1–15 mg |
| Sodium Chloride | 1–8 mg |
| Water for Injection | to 1.0 liter |

E. Oral suspensions containing a C5a receptor antagonist and a C5a receptor inactive agent may be prepared as follows:

| Ingredient | Amount per 5 ml dose |
| --- | --- |
| C5a receptor antagonist | 5–100 mg |
| C5a receptor inactive therapeutic agent | 5–100 mg |
| Polyvinylpyrrolidone | 150 mg |
| Poly oxyethylene sorbitan monolaurate | 25 mg |
| Benzoic Acid | 10 mg to 5 mL with sorbitol solution (70%) |

Example 12

Preparation of Radiolabeled Probe Compounds and Receptor Autoradiography

Compounds provided herein are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds prepared as described above.

Example 13

Assay for C5a Receptor Mediated Chemotaxis

This assay is a standard assay of C5a receptor mediated chemotaxis.

Human promonocytic U937 cells or purified human or non-human neutrophils are treated with dibutyryl cAMP for 48 hours prior to performing the assay. Human neutrophils or those from another mammalian species are used directly after isolation. The cells are pelleted and resuspended in culture media containing 0.1% fetal bovine serum (FBS) and 10 ug/ml calcein AM (a fluorescent dye). This suspension is then incubated at 37° C. for 30 minutes such that the cells take up the fluorescent dye. The suspension is then centrifuged briefly to pellet the cells, which are then resuspended in culture media containing 0.1% FBS at a concentration of approximately $3 \times 10^6$ cells/mL. Aliquots of this cell suspension are transferred to clean test tubes, which contain vehicle (1% DMSO) or varying concentrations of a compound of interest, and incubated at room temperature for at least 30 minutes. The chemotaxis assay is performed in CHEMO TX 101-8, 96 well plates (Neuro Probe, Inc. Gaithersburg, Md.). The bottom wells of the plate are filled with medium containing 0–10 nM of C5a, preferably derived from the same species of mammal as are the neutrophils or other cells (e.g., human C5a for the human U937 cells). The top wells of the plate are filled with cell suspensions (compound or vehicle-treated). The plate is then placed in a tissue culture incubator for 60 minutes. The top surface of the plate is washed with PBS to remove excess cell suspension. The number of cells that have migrated into the bottom well is then determined using a fluorescence reader. Chemotaxis index (the ratio of migrated cells to total number of cells loaded) is then calculated for each compound concentration to determine an $IC_{50}$ value.

As a control to ensure that cells retain chemotactic ability in the presence of the compound of interest, the bottom wells of the plate may be filled with varying concentrations chemo-attractants that do not mediate chemotaxis via the C5a receptor (e.g., zymosan-activated serum (ZAS), N-formylmethionyl-leucyl-phenylalanine (FMLP) or leukotriene B4 (LTB4)), rather than C5a, under which conditions the compounds provided herein preferably do not inhibit chemotaxis.

Preferred compounds exhibit $IC_{50}$ values of less than 1 µM in the above assay for C5a receptor mediated chemotaxis.

Example 14

Expression of a C5a Receptor

A human C5a receptor cDNA is obtained by PCR using 1) a forward primer adding a Kozak ribosome binding site and 2) a reverse primer that added no additional sequence, and 3) an aliquot of a Stratagene Human Fetal Brain cDNA library as template. The sequence of the resulting PCR product is as described by Gerard and Gerard, (1991) Nature 349:614–17. The PCR product is subcloned into the cloning vector pCR-Script AMP (STRATAGENE, La Jolla, Calif.) at the SrfI site. It is then excised using the restriction enzymes EcoRI and NotI and subcloned in the appropriate orientation for expression into the baculoviral expression vector pBac-PAK 9 (CLONTECH, Palo Alto, Calif.) that has been digested with EcoRI and NotI.

Example 15

Baculoviral Preparations for C5a Expression

The human C5a (hC5a) receptor baculoviral expression vector is co-transfected along with BACULOGOLD DNA (BD PharMingen, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Lenexa, Kans.) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 ml of insect medium for amplification. Each 1 ml volume of recombinant baculovirus (at passage 0) is used to infect a separate T25 flask containing $2 \times 10^6$ S$f$9 cells in 5 mls of insect medium. After five days of incubation at 27° C., supernatant medium is harvested from each of the T25 infections for use as passage 1 inoculum.

Two of seven recombinant baculoviral clones are then chosen for a second round of amplification, using 1 ml of passage 1 stock to infect $1 \times 10^8$ cells in 100 ml of insect medium divided into 2 T175 flasks. Forty-eight hours post infection, passage 2 medium from each 100 ml prep is harvested and plaque assayed for titer. The cell pellets from the second round of amplification are assayed by affinity binding as described below to verify recombinant receptor expression. A third round of amplification is then initiated using a multiplicity of infection of 0.1 to infect a liter of S$f$9 cells. Forty hours post-infection the supernatant medium is harvested to yield passage 3 baculoviral stock.

The remaining cell pellet is assayed for affinity binding using the "Binding Assays" essentially as described by DeMartino et al. (1994) *J. Biol. Chem.* 269:14446–50 at page 14447, adapted as follows. Radioligand is 0.005–0.500 nM [$^{125}$I]C5a (human recombinant; New England Nuclear Corp., Boston, Mass.); the hC5a receptor-expressing baculoviral cells are used instead of 293 cells; the assay buffer contains 50 mM Hepes pH. 7.6, 1 mM $CaCl_2$, 5 mM $MgCl_2$, 0.1% BSA, pH 7.4, 0.1 mM bacitracin, and 100 KIU/ml aprotinin; filtration is carried out using GF/C WHATMAN filters (presoaked in 1.0% polyethyeneimine for 2 hours prior to use); and the filters are washed twice with 5 mLs cold binding buffer without BSA, bacitracin, or aprotinin.

Titer of the passage 3 baculoviral stock is determined by plaque assay and a multiplicity of infection, incubation time course, binding assay experiment is carried out to determine conditions for optimal receptor expression. A multiplicity of infection of 0.1 and a 72-hour incubation were the best infection parameters found for hC5a receptor expression in up to 1-liter S$f$9 cell infection cultures.

Example 16

Baculoviral Infections

Log-phase S$f$9 cells (INVITROGEN Corp., Carlsbad Calif.) are infected with one or more stocks of recombinant baculovirus followed by culturing in insect medium at 27° C. Infections are carried out either only with virus directing the expression of the hC5a receptor or with this virus in combination with three G-protein subunit-expression virus stocks: 1) rat $G\square_{i2}$ G-protein-encoding virus stock (BIOSIGNAL #V5J008), 2) bovine b1 G-protein-encoding virus stock (BIOSIGNAL #V5H012), and 3) human g2 G-protein-encoding virus stock (BIOSIGNAL #V6B003), all of which may be obtained from BIOSIGNAL Inc. (Montreal, Canada).

The infections are conveniently carried out at a multiplicity of infection of 0.1:1.0:0.5:0.5. At 72 hours post-infection, a sample of cell suspension is analyzed for viability by trypan blue dye exclusion, and the remaining S$f$9 cells are harvested via centrifugation (3000 rpm/10 minutes/4° C.).

Example 17

Purified Recombinant Insect Cell Membranes

S$f$9 cell pellets are resuspended in homogenization buffer (10 mM HEPES, 250 mM sucrose, 0.5 ug/ml leupeptin, 2 ug/ml Aprotinin, 200 uM PMSF, and 2.5 mM EDTA, pH 7.4) and homogenized using a POLYTRON homogenizer (setting 5 for 30 seconds). The homogenate is centrifuged (536×g/10 minutes/4° C.) to pellet the nuclei. The supernatant containing isolated membranes is decanted to a clean centrifuge tube, centrifuged (48,000×g/30 minutes, 4° C.) and the resulting pellet resuspended in 30 ml homogenization buffer. This centrifugation and resuspension step is repeated twice. The final pellet is resuspended in ice cold Dulbecco's PBS containing 5 mM EDTA and stored in frozen aliquots at −80° C. until needed. The protein concentration of the resulting membrane preparation (hereinafter "P2 membranes") is conveniently measured using a Bradford protein assay (Bio-Rad Laboratories, Hercules, Calif.). By this measure, a 1-liter culture of cells typically yields 100–150 mg of total membrane protein.

Example 18

Radioligand Binding Assays

Purified P2 membranes, prepared by the method given above, are resuspended by Dounce homogenization (tight pestle) in binding buffer (50 mM Hepes pH. 7.6, 120 mM NaCl, 1 mM $CaCl_2$, 5 mM $MgCl_2$, 0.1% BSA, pH 7.4, 0.1 mM bacitracin, 100 KIU/ml aprotinin).

For saturation binding analysis, membranes (5–50 μg) are added to polypropylene tubes containing 0.005–0.500 nM [$^{125}$I]C5a (human (recombinant), New England Nuclear Corp., Boston, Mass.). Nonspecific binding is determined in the presence of 300 nM hC5a (Sigma Chemical Co., St. Louis, Mo.) and accounts for less than 10% of total binding. For evaluation of guanine nucleotide effects on receptor affinity, GTPγS is added to duplicate tubes at the final concentration of 50 μM.

For competition analysis, membranes (5–50 μg) are added to polypropylene tubes containing 0.030 nM [$^{125}$I]C5a (human). Non-radiolabeled displacers are added to separate assays at concentrations ranging from $10^{-10}$ M to $10^{-5}$ M to yield a final volume of 0.250 mL. Nonspecific binding is determined in the presence of 300 nM hC5a (Sigma Chemical Co., St. Louis, Mo.) and accounts for less than 10% of total binding. Following a 2-hour incubation at room temperature, the reaction is terminated by rapid vacuum filtration. Samples are filtered over presoaked (in 1.0% polyethyleneimine for 2 hours prior to use) GF/C WHATMAN filters and rinsed 2 times with 5 mLs cold binding buffer without BSA, bacitracin, or aprotinin. Remaining bound radioactivity is quantified by gamma counting. $K_1$ and Hill coefficient ("nH") are determined by fitting the Hill equation to the measured values with the aid of SIGMA-PLOT software (SPSS Inc., Chicago, Ill.).

Example 19

Agonist-Induced GTP Binding

Agonist-stimulated GTP-gamma $^{35}$S binding ("GTP binding") activity can be used to identify agonist and antagonist compounds and to differentiate neutral antagonist compounds from those that possess inverse agonist activity. This activity can also be used to detect partial agonism mediated by antagonist compounds. A compound being analyzed in this assay is referred to herein as a "test compound." Agonist-stimulated GTP binding activity is measured as follows: Four independent baculoviral stocks (one directing the expression of the hC5a receptor and three directing the expression of each of the three subunits of a heterotrimeric G-protein) are used to infect a culture of Sf9 cells as described in Example 16.

Agonist-stimulated GTP binding on purified membranes (prepared as described in Example 17) is assessed using hC5a (Sigma Chemical Co., St. Louis, Mo.) as agonist in order to ascertain that the receptor/G-protein-alpha-beta-gamma combination(s) yield a functional response as measured by GTP binding.

P2 membranes are resuspended by Dounce homogenization (tight pestle) in GTP binding assay buffer (50 mM Tris pH 7.0, 120 mM NaCl, 2 mM MgCl2, 2 mM EGTA, 0.1% BSA, 0.1 mM bacitracin, 100 KIU/mL aprotinin, 5 $\mu$M GDP) and added to reaction tubes at a concentration of 30 $\mu$g protein/reaction tube. After adding increasing doses of the agonist hC5a at concentrations ranging from $10^{-12}$ M to $10^{-6}$ M, reactions are initiated by the addition of 100 pM GTP-gamma $^{35}$S. In competition experiments, non-radiolabeled test compounds are added to separate assays at concentrations ranging from $10^{-10}$ M to $10^{-5}$ M along with 10 nM hC5a to yield a final volume of 0.25 mL.

Neutral antagonists are those test compounds that reduce the C5a-stimulated GTP binding activity towards, but not below, baseline (the level of GTP bound by membranes in this assay in the absence of added C5a or other agonist and in the further absence of any test compound).

In contrast, in the absence of added C5a certain preferred compounds will reduce the GTP binding activity of the receptor-containing membranes below baseline, and are thus characterized as inverse agonists. If a test compound that displays antagonist activity does not reduce the GTP binding activity below baseline in the absence of the C5a agonist, it is characterized as a neutral antagonist.

An antagonist test compound that elevates GTP binding activity above baseline in the absence of added hC5a in this GTP binding assay is characterized as having partial agonist activity. Preferred antagonist compounds do not elevate GTP binding activity under such conditions more than 10%, 5% or 2% above baseline.

Following a 60-minute incubation at room temperature, the reactions are terminated by vacuum filtration over GF/C filters (pre-soaked in wash buffer, 0.1% BSA) followed by washing with ice-cold wash buffer (50 mM Tris pH 7.0, 120 mM NaCl). The amount of receptor-bound (and thereby membrane-bound) GTP-gamma $^{35}$S is determined by measuring the bound radioactivity, preferably by liquid scintillation spectrometry of the washed filters. Non-specific binding is determined using 10 mM GTP-gamma $^{35}$S and typically represents less than 5 percent of total binding. Data is expressed as percent above basal (baseline). The results of these GTP binding experiments may be conveniently analyzed using SIGMAPLOT software.

Example 20

Calcium Mobilization Assays

A. Response to C5a

U937 cells are grown in differentiation media (1 mM dibutyryl cAMP in RPMI 1640 medium containing 10% fetal bovine serum) for 48 hrs at 37° C. then reseeded onto 96-well plates suitable for use in a FLIPR™ Plate Reader (Molecular Devices Corp., Sunnyvale Calif.). Cells are grown an additional 24 hours (to 70–90% confluence) before the assay. The cells are then washed once with Krebs Ringer solution. FLUO-3 calcium sensitive dye (Molecular Probes, Inc. Eugene, Oreg.) is added to 10 $\mu$g/mL and incubated with the cells at room temperature for 1 to 2 hours. The 96 well plates are then washed to remove excess dye. Fluorescence responses, measured by excitation at 480 nM and emission at 530 nM, are monitored upon the addition of human C5a to the cells to a final concentration of 0.01–30.0 nM, using the FLIPR™ device (Molecular Devices). Differentiated U937 cells typically exhibit signals of 5,000–50,000 Arbitrary Fluorescent Light Units in response to agonist stimulation.

B. Assays for Determination of ATP Responses

Differentiated U937 cells (prepared and tested as described above under "A. Response to C5a") are stimulated by the addition of ATP (rather than C5a) to a final concentration of 0.01 to 30 $\mu$M. This stimulation typically triggers a signal of 1,000 to 12,000 arbitrary fluorescence light units. Certain preferred compounds produce less than a 10%, less than a 5%, or less than a 2% alteration of this calcium mobilization signal when this control assay is carried out in the presence of the compound, as compared to the signal when the assay is performed in the absence of the compound.

C. Assays for the Identification of Receptor Modulatory Agents: Antagonists and Agonists The calcium mobilization assay described above may be readily adapted for identifying test compounds that have agonist or antagonist activity at the human C5a receptor.

For example, in order to identify antagonist compounds, differentiated U937 cells are washed and incubated with Fluo-3 dye as described above. One hour prior to measuring the fluorescence signal, a subset of the cells is incubated with 1 $\mu$M of at least one compound to be tested. The fluorescence response upon the subsequent addition of 0.3 nM (final concentration) human recombinant C5a is monitored using the FLIPR™ plate reader. Antagonist compounds elicit at least a 2-fold decrease in the fluorescence response relative to that measured in the presence of human C5a alone. Preferred antagonist compounds elicit at least a 5-fold, preferably at least a 10-fold, and more preferably at least a 20-fold decrease in the fluorescence response relative to that measured in the presence of human C5a alone. Agonist compounds elicit an increase in fluorescence without the addition of C5a, which increase will be at least partially blocked by a known C5a receptor antagonist.

Example 21

Assays to Evaluate Agonist Activity of Small Molecule C5a Receptor Antagonists

Preferred compounds provided herein are C5a receptor antagonists that do not possess significant (e.g., greater than 5%) agonist activity in any of the C5a mediated functional assays discussed herein. Specifically, this undesired agonist activity can be evaluated, for example, in the GTP binding assay of Example 19, by measuring small molecule mediated GTP binding in the absence of the natural agonist, C5a. Similarly, in a calcium mobilization assay (e.g., that of Example 20), a small molecule compound can be directly assayed for the ability of the compound to stimulate calcium levels in the absence of the natural agonist, C5a. The preferred extent of C5a agonist activity exhibited by compounds provided herein is less than 10%, more preferably less than 5% and most preferably less than 2% of the response elicited by the natural agonist, C5a.

The foregoing description is illustrative thereof, and it will be understood that variations and modifications can be effected without departing from the scope or spirit of the invention as set forth in the following claims.

What is claimed is:

1. A compound of Formula I:

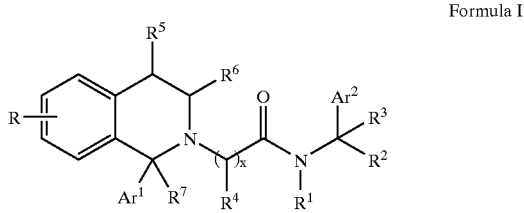

Formula I or a pharmaceutically acceptable salt thereof, wherein:

x is 1, 2 or 3;

R represents from 0 to 4 substituents independently chosen from halogen, hydroxy, optionally substituted alkoxy, optionally substituted alkyl, optionally substituted alkenyl, optionally substituted alkynyl, cyano, amino, nitro, —COOH, carboxamide, optionally substituted mono- and di-alkyl amino, optionally substituted haloalkyl, and optionally substituted haloalkoxy;

$R^1$ is selected from alkyl, alkenyl, alkynyl, cycloalkyl, (cycloalkyl)alkyl, aryl, heteroaryl, (aryl)alkyl, (heteroaryl)alkyl, and indanyl, each of which is optionally substituted;

$R^2$, $R^3$ and each occurrence of $R^4$ are independently selected from hydrogen, halogen, optionally substituted alkyl, and optionally substituted alkoxy;

$R^5$ and $R^6$ are independently selected from (i) hydrogen, halogen, hydroxy, amino, and cyano; and (ii) alkyl, alkenyl, alkynyl, alkoxy, haloalkyl, haloalkoxy, and mono- and di-(alkyl)amino, each of which is optionally substituted;

$R^7$ is: (a) (i) hydrogen; or (ii) alkyl, alkenyl, alkynyl, alkoxy or arylalkyl, each of which is optionally substituted; and $Ar^1$ is:

(i) phenyl, naphthyl, biphenyl, or heterocycle, each of which is optionally substituted; or (ii) optionally substituted phenyl fused to a 5- to 7-membered saturated or partially unsaturated ring having from 5 to 7 ring atoms, with 0, 1, or 2 ring atoms independently chosen from N, O and S, and with remaining ring atoms being carbon;

or (b) taken together with $Ar^1$ and the carbon atom to which $R^7$ and $Ar^1$ are attached to form an optionally substituted group of the formula:

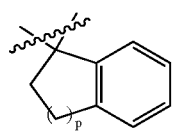

wherein p is an integer from 1 to about 3; and $Ar^2$ is (i) optionally substituted aryl or (ii) optionally substituted heteroaryl having 5 to 7 ring atoms and from 1 to 3 ring heteroatoms independently selected from N, O and S.

2. A compound or salt according to claim 1, wherein:

x is 1;

R represents from 0 to 4 substituents independently chosen from halogen, hydroxy, cyano, amino, nitro, —COOH, carboxamide, $C_1$–$C_6$alkoxy, $C_1$–$C_6$alkyl, $C_2$–$C_6$alkenyl, $C_2$–$C_6$alkynyl, mono- and di-($C_1$–$C_6$alkyl)amino, $C_1$–$C_6$haloalkyl, and $C_1$–$C_6$haloalkoxy;

$R^1$ is selected from (aryl)$C_0$–$C_6$alkyl, (heteroaryl)$C_0$–$C_6$alkyl, and indanyl, each of which is substituted with from 0 to 3 substituents independently selected from halogen, hydroxy, cyano, amino, nitro, —COOH, carboxamide, $C_1$–$C_6$alkoxy, $C_1$–$C_6$alkyl, $C_2$–$C_6$alkenyl, $C_2$–$C_6$alkynyl, mono- and di-($C_1$–$C_6$alkyl)amino, $C_1$–$C_6$haloalkyl, and $C_1$–$C_6$haloalkoxy;

$R^2$, $R^3$, and each occurrence of $R^4$ are independently selected from hydrogen, halogen, $C_1$–$C_6$alkyl, and $C_1$–$C_6$alkoxy;

$R^5$ and $R^6$ are independently selected from hydrogen, halogen, cyano, $C_1$–$C_6$alkyl, $C_2$–$C_6$alkenyl, $C_2$–$C_6$alkynyl, $C_1$–$C_6$alkoxy, $C_1C_6$haloalkyl, $C_1$–$C_6$haloalkoxy, hydroxy, amino, and mono- and di-($C_1$–$C_6$alkyl)amino;

and either:

(a) $R^7$ is (i) hydrogen; or (ii) $C_1$–$C_6$alkyl, $C_2$–$C_6$alkenyl, $C_1$–$C_6$alkynyl, $C_1$–$C_6$alkoxy or (aryl) $C_1$–$C_6$alkyl, each of which is optionally substituted; and $Ar^1$ is (i) phenyl; (ii) naphthyl; (iii) biphenyl; (iv) a heterocyclic group having 1 or 2 rings, 3 to 8 atoms in each ring and in at least one ring from 1 to 3 heteroatoms independently selected from N, O and S; or (v) phenyl fused to a 5- to 7-membered saturated or partially unsaturated ring having from 5 to 7 ring atoms, with 0, 1 or 2 ring atoms chosen from N, O and S, and with remaining ring atoms being carbon;

wherein each of (i), (ii), (iii), (iv) and (v) is substituted with from 0 to 4 substituents independently selected from halogen, hydroxy, cyano, amino, nitro, $C_1$–$C_6$alkoxy, $C_1$–$C_6$alkyl, $C_2$–$C_6$alkenyl, $C_2$–$C_6$alkynyl, $C_1$–$C_6$alkoxycarbonyl, —COOH, carboxamide, mono- and di-($C_1$–$C_6$alkyl)amino, $C_1$–$C_6$haloalkyl, and $C_1$–$C_6$haloalkoxy; or (b) $R^7$ is taken together with $Ar^1$ and the carbon atom to which $R^7$ and $Ar^1$ are attached to form a group of the formula:

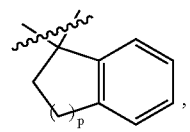

substituted with from 0 to 4 substituents independently chosen from halogen, hydroxy, cyano, amino, nitro, —COOH, carboxamide, $C_1$–$C_6$ alkoxy, $C_1$–$C_6$alkyl, $C_2$–$C_6$alkenyl, $C_2$–$C_6$alkynyl, mono- and di-($C_1$–$C_6$alkyl)amino, $C_1$–$C_6$haloalkyl, and $C_1$–$C_6$haloalkoxy, wherein p is an integer from 1 to about 3; and $Ar^2$ is aryl or heteroaryl, each of which is substituted with from 0 to 5 substituents independently selected from halogen, hydroxy, cyano, amino, nitro, —COOH, $C_1$–$C_6$alkoxy, $C_1$–$C_6$alkyl, $C_2$–$C_6$alkenyl, $C_2$–$C_6$alkynyl, $C_1$–$C_6$alkoxycarbonyl, carboxamide, mono- and di-($C_1$–$C_6$alkyl)carboxamide, mono- and di-($C_1$–$C_6$alkyl)amino, $C_1$–$C_6$haloalkyl, and $C_1$–$C_6$haloalkoxy.

3. A compound or salt according to claim 1, wherein $R^1$ is indanyl, substituted with 0, 1, or 2 substituents independently selected from halogen, hydroxy, $C_1$–$C_2$alkoxy, $C_1$–$C_2$alkyl, halo$C_1$–$C_2$alkyl, and halo$C_1$–$C_2$alkoxy.

4. A compound or salt according to claim 1, wherein $R^1$ is phenyl($C_0$–$C_4$alkyl), pyridyl($C_0$–$C_4$alkyl), $C_0$–$C_4$alkyl, or indolyl($C_0$–$C_4$alkyl), each of which is substituted with from 0 to 3 substituents independently selected from halogen, hydroxy, $C_1$–$C_2$alkoxy, $C_1$–$C_2$alkyl, $C_1$–$C_2$haloalkyl, and $C_1$–$C_2$haloalkoxy.

5. A compound or salt according to claim 1, of Formula II

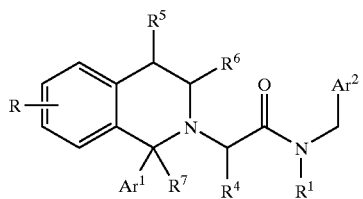

Formula II wherein:

R represents from 0 to 4 substituents independently chosen from fluoro, chloro, hydroxy, optionally substituted $C_1$–$C_6$alkoxy and optionally substituted $C_1$–$C_6$alkyl;

$R^4$ is hydrogen, optionally substituted $C_1$–$C_6$alkyl, $C_1$–$C_6$haloalkyl, fluoro, or chloro;

$R^5$ and $R^6$ are independently selected from hydrogen, fluoro, chloro, optionally substituted $C_1$–$C_6$alkyl, optionally substituted $C_1$–$C_6$alkoxy, $C_1$–$C_6$haloalkyl, and $C_1$–$C_6$haloalkoxy; and $R^7$ is hydrogen or $C_1$–$C_6$ alkyl.

6. A compound or salt according to claim 5, wherein

R represents from 0 to 4 substituents independently chosen from fluoro, chloro, hydroxy, $C_1$–$C_6$alkoxy, and $C_1$–$C_6$alkyl;

$R^1$ is selected from $C_3$–$C_7$cycloalkyl, ($C_3$–$C_7$cycloalkyl) $C_1$–$C_4$alkyl, (heteroaryl)$C_0$–$C_4$alkyl, (aryl)$C_0$–$C_4$alkyl, and indanyl, each of which is substituted with from 0 to 3 substituents independently selected from halogen, hydroxy, cyano, amino, nitro, $C_1$–$C_6$alkoxy, $C_1$–$C_6$alkyl, $C_2$–$C_6$alkenyl, $C_2$–$C_6$alkynyl, —COOH, carboxamide, mono- and di-($C_1$–$C_6$alkyl)amino, $C_1$–$C_6$haloalkyl, and $C_1$–$C_6$haloalkoxy;

$R^4$ is hydrogen, $C_1$–$C_6$alkyl, $C_1$–$C_6$haloalkyl, fluoro, or chloro;

$R^5$ and $R^6$ are independently selected from hydrogen, fluoro, chloro, $C_1$–$C_6$alkyl, $C_1$–$C_6$alkoxy, halo$C_1$–$C_6$alkyl, and $C_1$–$C_6$haloalkoxy; and $R^7$ is hydrogen or $C_1$–$C_6$ alkyl.

7. A compound or salt according to claim 6, wherein $Ar^1$ is:

(i) phenyl substituted with from 0 to 4 substituents independently selected from halogen, hydroxy, cyano, amino, nitro, —COOH, carboxamide, $C_1$–$C_3$alkoxy, $C_1$–$C_3$alkyl, $C_1$–$C_2$haloalkyl, $C_1$–$C_2$alkoxycarbonyl, mono- and di-($C_1$–$C_2$alkyl)amino, and $C_1$–$C_2$haloalkoxy;

(ii) naphthyl;

(iii) heterocyclic groups having 1 or 2 rings, 3 to 8 atoms in each ring and in at least one ring from 1 to 3 heteroatoms independently selected from N, O and S;

(iv) biphenyl, wherein each phenyl group is substituted with 0 to 2 groups independently selected from halogen, $C_1$–$C_2$alkyl, and $C_1$–$C_2$alkoxy; or (v) phenyl fused to a 5- to 7-membered saturated or partially unsaturated ring having from 5 to 7 ring atoms, with 0, 1, or 2 ring atoms independently chosen from N, O and S, and with remaining ring atoms being carbon;

wherein each of (ii), (iii), (iv) and (v) is substituted with from 0 to 4 substituents independently selected from halogen, hydroxy, $C_1$–$C_2$alkyl, $C_1$–$C_2$alkoxy, $C_1$–$C_2$haloalkyl, and halo$C_1$–$C_2$alkoxy.

8. A compound or salt according to claim 7, wherein $Ar^2$ is phenyl or heteroaryl having about 5 to 7 ring atoms and between 1 and 3 ring heteroatoms independently selected from N, O and S, each of which is substituted with from 0 to 5 substituents independently selected from halogen, hydroxy, cyano, amino, nitro, —COOH, $C_1$–$C_3$alkoxy, $C_1$–$C_3$alkyl, carboxamide, dimethylcarboxamide, mono- and di-($C_1$–$C_2$alkyl)amino, $C_1$–$C_2$haloalkyl, and $C_1$–$C_2$haloalkoxy.

9. A compound or salt according to claim 1, of Formula III

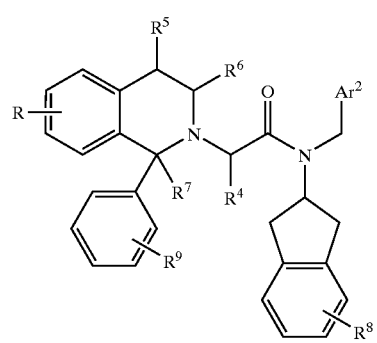

Formula III wherein:

R represents from 0 to 4 substituents independently chosen from fluoro, chloro, hydroxy, $C_1$–$C_6$alkoxy, and $C_1$–$C_6$alkyl;

$R^4$ is hydrogen, $C_1$–$C_6$alkyl, $C_1$–$C_6$haloalkyl, fluoro, or chloro;

$R^8$ represents from 0 to 4 substituents independently chosen from $C_1$–$C_6$alkyl, $C_1$–$C_6$alkoxy, $C_1$–$C_6$haloalkyl, $C_1$–$C_6$haloalkoxy, fluoro, and chloro;

$R^5$ and $R^6$ are independently selected from hydrogen, fluoro, chloro, $C_1$–$C_6$alkyl, optionally substituted $C_1$–$C_6$alkoxy, and halo$C_1$–$C_6$alkyl;

$R^7$ is hydrogen or $C_1$–$C_6$alkyl;

$R^9$ from 0 to 5 substituents independently chosen from halogen, hydroxy, $C_1$–$C_6$alkyl, $C_1$–$C_6$alkoxy, $C_1$–$C_6$haloalkyl, and $C_1$–$C_6$haloalkoxy; and $Ar^2$ is (i) phenyl or (ii) heteroaryl having 5 to 7 ring atoms and from 1 to 3 ring heteroatoms independently selected from N, O and S, wherein each of (i) and (ii) is optionally substituted with from 1 to 5 substituents independently selected from halogen, hydroxy, cyano, amino, nitro, —COOH, carboxamide, dimethylcarboxamide, $C_1$–$C_3$alkoxy, $C_1$–$C_3$alkyl, mono- and di-($C_1$–$C_2$alkyl)amino, $C_1$–$C_2$haloalkyl, and $C_1$–$C_2$haloalkoxy.

10. A compound or salt according to claim 1, of Formula IV

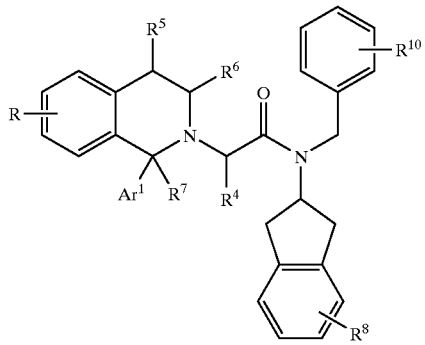

Formula IV wherein:

R represents from 0 to 4 substituents independently chosen from fluoro, chloro, hydroxy, $C_1$–$C_6$alkoxy, and $C_1$–$C_6$alkyl;

$R^4$ is hydrogen, $C_1$–$C_6$alkyl, $C_1$–$C_6$haloalkyl, fluoro, or chloro;

$R^8$ represents from 0 to 4 substituents independently chosen from $C_1$–$C_6$alkyl, $C_1$–$C_6$haloalkyl, fluoro, and chloro;

$R^5$ and $R^6$ are independently selected from hydrogen, fluoro, chloro, $C_1$–$C_6$alkyl, optionally substituted $C_1$–$C_6$alkoxy, and $C_1$–$C_6$haloalkyl;

$R^7$ is hydrogen or $C_1$–$C_6$alkyl;

$R^{10}$ represents from 0 to 5 substituents independently chosen from fluoro, chloro, bromo, iodo, hydroxy, nitro, cyano, —COOH, carboxamide, dimethylcarboxamide, $C_1$–$C_6$alkyl, $C_1$–$C_6$alkoxy, $C_1$–$C_6$haloalkyl, and $C_1$–$C_6$haloalkoxy; and $Ar_1$ is:

(i) phenyl substituted with from 0 to 5 substituents independently selected from halogen, hydroxy, cyano, amino, nitro, —COOH, carboxamide, $C_1$–$C_3$alkoxy, $C_1$–$C_3$alkyl, $C_1$–$C_2$haloalkyl, $C_1$–$C_2$alkoxycarbonyl, mono- and di-($C_1$–$C_2$alkyl)amino, and $C_1$–$C_2$haloalkoxy;

(ii) naphthyl;

(iii) heterocyclic groups having 1 or 2 rings, 3 to 8 atoms in each ring and in at least one ring from 1 to 3 heteroatoms independently selected from N, O and S;

(iv) biphenyl; or (v) phenyl fused to a 5- to 7-membered saturated or partially unsaturated ring having from 5 to 7 ring atoms, with 0, 1, or 2 ring atoms independently chosen from N, O and S, and with remaining ring atoms being carbon;

wherein each of (ii), (iii), (iv) and (v) is substituted with from 0 to 4 substituents independently selected from halogen, hydroxy, $C_1$–$C_2$alkyl, $C_1$–$C_2$alkoxy, $C_1$–$C_2$haloalkyl, and $C_1$–$C_2$haloalkoxy.

11. A compound according to claim 1 of the Formula VI

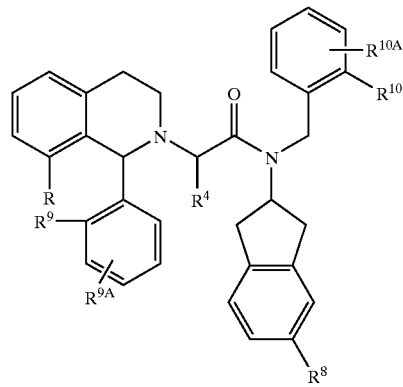

Formula VI or a pharmaceutically acceptable salt thereof, wherein:

R is hydrogen, fluoro, chloro, hydroxy, methyl, or methoxy;

$R^4$ is hydrogen, methyl, or ethyl;

$R^8$ is hydrogen, fluoro, chloro, methyl, or methoxy;

$R^9$ is fluoro, chloro, methyl, ethyl, methoxy, ethoxy, mono-, di- or tri-fluoromethyl, or mono-, di-, or tri-fluoromethoxy;

$R^{9A}$ represents 0, 1, or 2 substituents independently selected from hydrogen, fluoro, chloro, methyl, methoxy, mono-, di- and tri-fluoromethyl, and mono-, di-, and tri-fluoromethoxy;

$R^{10}$ is hydrogen, fluoro, chloro, hydroxy, methyl, methoxy, mono-, di-, or tri-fluoromethyl, or mono-, di-, or tri-fluoromethoxy; and $R^{10A}$ represents from 0 to 3 substituents independently selected from hydrogen, fluoro, chloro, hydroxy, methyl, methoxy, mono-, di- and tri-fluoromethyl, and mono-, di-, and tri-fluoromethoxy.

12. A compound according to claim 1 of Formula VIII

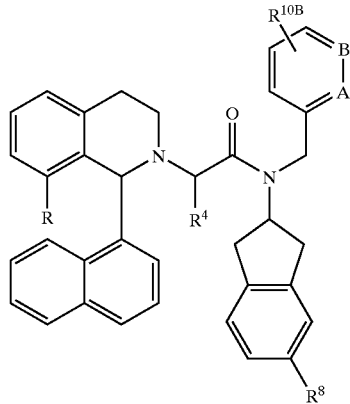

Formula VIII or a pharmaceutically acceptable salt thereof, wherein:

A is N or $CR^{10}$;

B is N or $CR^{10A}$, wherein at least one of A and B is not N;

R is hydrogen, fluoro, chloro, hydroxy, methyl, or methoxy;

$R^4$ is hydrogen, methyl, or ethyl;

$R^8$ is hydrogen, fluoro, chloro, methyl or methoxy;

$R^{10}$, if present, is hydrogen, fluoro, chloro, hydroxy, nitro, cyano, methyl, methoxy, mono-, di- or tri-fluoromethyl, or mono-, di-, or tri-fluoromethoxy;

$R^{10A}$, if present, is hydrogen, fluoro, chloro, hydroxy, nitro, cyano, methyl, methoxy, mono-, di- or tri-fluoromethyl, or mono-, di-, or tri-fluoromethoxy; and $R^{10B}$ represents from 0 to 3 substituents independently selected from fluoro, chloro, hydroxy, nitro, cyano, methyl, methoxy, mono-, di- and tri-fluoromethyl, and mono-, di-, and tri-fluoromethoxy.

13. A compound according to claim 1, of Formula X

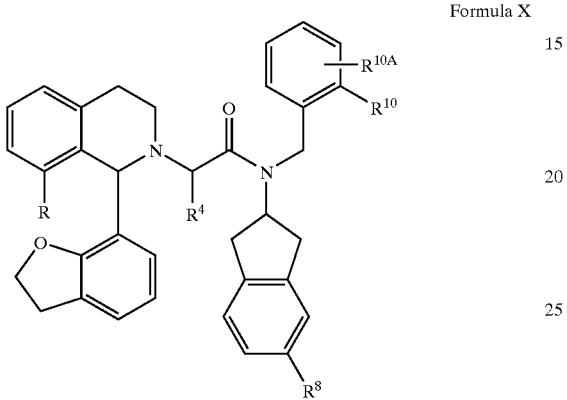

Formula X or a pharmaceutically acceptable salt thereof, wherein:

R is hydrogen, fluoro, chloro, hydroxy, methyl or methoxy;

$R^4$ is hydrogen, methyl, or ethyl;

$R^8$ is hydrogen, fluoro, chloro, methyl or methoxy;

$R^{10}$ is hydrogen, fluoro, chloro, hydroxy, methyl, methoxy, mono-, di- or tri-fluoro methyl, or mono-, di- or tri-fluoromethoxy; and $R^{10A}$ represents from 0 to 3 substituents independently selected from hydrogen, fluoro, chloro, hydroxy, methyl, methoxy, mono-, di- and tri-fluoromethyl, and mono-, di-, and tri-fluoromethoxy.

14. A compound or salt according to claim 1, of Formula XI

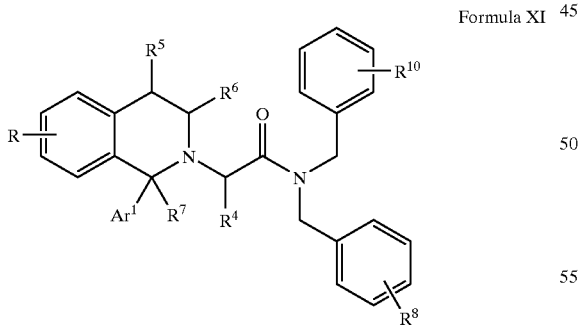

Formula XI wherein:

R represents from 0 to 4 substituents independently chosen from fluoro, chloro, hydroxy, $C_1$–$C_6$alkoxy, and $C_1$–$C_6$alkyl;

$R^4$ is hydrogen, $C_1$–$C_6$alkyl, $C_1$–$C_6$haloalkyl, fluoro, or chloro;

$R^8$ represents from 0 to 4 substituents independently chosen from $C_1$–$C_6$alkyl, $C_1$–$C_6$haloalkyl, fluoro, and chloro;

$R^5$ and $R^6$ are independently selected hydrogen, fluoro, chloro, $C_1$–$C_6$alkyl, optionally substituted $C_1$–$C_6$alkoxy, and $C_1$–$C_6$haloalkyl;

$R^7$ is hydrogen or $C_1$–$C_6$alkyl;

$R^{10}$ represents from 0 to 5 substituents independently chosen from fluoro, chloro, bromo, iodo, hydroxy, nitro, cyano, —COOH, carboxamide, dimethylcarboxamide, $C_1$–$C_6$alkyl, $C_1$–$C_6$alkoxy, $C_1$–$C_6$haloalkyl, and $C_1$–$C_6$haloalkoxy; and $Ar_1$ is:

(i) phenyl optionally substituted with from 1 to 5 substituents independently selected from halogen, hydroxy, cyano, amino, nitro, —COOH, carboxamide, $C_1$–$C_3$alkoxy, $C_1$–$C_3$alkyl, $C_1$–$C_2$haloalkyl, $C_1$–$C_2$alkoxycarbonyl, mono- and di-($C_1$–$C_2$alkyl)amino, and $C_1$–$C_2$haloalkoxy;

(ii) naphthyl;

(iii) heterocyclic groups having 1 or 2 rings, 3 to 3 atoms in each ring and in at least one ring from 1 to 3 heteroatoms independently selected from N, O and S;

(iv) biphenyl; or (v) phenyl fused to a 5- to 7-membered saturated or partially unsaturated ring having from 5 to 7 ring atoms, with 0, 1, or 2 ring atoms independently chosen from N, O and S, and with remaining ring atoms being carbon;

wherein each of (ii), (iii), (iv) and (v) is optionally substituted with from 1 to 4 substituents independently selected from halogen, hydroxy, $C_1$–$C_2$alkyl, $C_1$–$C_2$alkoxy, $C_1$–$C_2$haloalkyl, and $C_1$–$C_2$haloalkoxy.

15. A compound according to claim 1, which is:

N-(indan-2-yl)-N-(2-fluorobenzyl)-2-[8-methoxy-1-(2-methylphenyl)-3,4-dihydroisoquinolin-2(1H)-yl]acetamide;

N-(indan-2-yl)-N-(2-fluorobenzyl)-2-[1-methyl-1-(2-methylphenyl)-3,4-dihydroisoquinolin-2(1H)-yl]acetamide;

N-(indan-2-yl)-2-[1-ethyl-1-(2-methylphenyl)-3,4-dihydroisoquinolin-2(1H)-yl]-N-(2-fluorobenzyl)acetamide;

2-[1-(2,4-difluorophenyl)-3,4-dihydroisoquinolin-2(1H)-yl]-N-(indan-2-yl)-N-(2-fluorobenzyl)acetamide;

N-(2-fluorobenzyl)-N-{3-[1-(2-methylphenyl)-3,4-dihydroisoquinolin-2(1H)-yl]-3-oxopropyl}indan-2-amine;

N-(indan-2-yl)-N-(2-fluorobenzyl)-2-[1-(2-methylphenyl)-3,4-dihydroisoquinolin-2(1H)-yl]propanamide;

N-(indan-2-yl)-2-[1-(2-methylphenyl)-3,4-dihydroisoquinolin-2(1H)-yl]-N-(pyridin-2-ylmethyl)acetamide;

N-(indan-2-yl)-2-[1-(2-methylphenyl)-3,4-dihydroisoquinolin-2(1H)-yl]-N-(pyridin-3-ylmethyl)acetamide;

2-[1-(2-bromophenyl)-3,4-dihydroisoquinolin-2(1H)-yl]-N-(indan-2-yl)-N-(2-fluorobenzyl)acetamide;

N-(indan-2-yl)-2-[1-(2-methylphenyl)-3,4-dihydroisoquinolin-2(1H)-yl]-N-(1,3-thiazol-2-ylmethyl)acetamide;

N-(indan-2-yl)-N-(2-fluorobenzyl)-2-[1-(2-methoxyphenyl)-3,4-dihydroisoquinolin-2(1H)-yl]acetamide;

N-(indan-2-yl)-2-[1-(2,3-dimethylphenyl)-3,4-dihydroisoquinolin-2(1H)-yl]-N-(2-fluorobenzyl)acetamide;

N-(indan-2-yl)-N-(2-fluorobenzyl)-2-[(1R)-1-(2-methylphenyl)-3,4-dihydroisoquinolin-2(1H)-yl]acetamide;

N-(indan-2-yl)-N-(2-fluorobenzyl)-2-[(4R)-4-methyl-1-(2-methylphenyl)-3,4-dihydroisoquinolin-2(1H)-yl]acetamide;

N-(indan-2-yl)-N-(2-fluorobenzyl)-2-[(1S)-1-(2-methylphenyl)-3,4-dihydroisoquinolin-2(1H)-yl]acetamide;

N-(indan-2-yl-2-[1-(2-ethylphenyl)-3,4-dihydroisoquinolin-2(1H)-yl]-N-(2-fluorobenzyl)acetamide;

N-(2Fluoro-benzyl)-N-indan-2-yl-2-(4-methyl-1-o-tolyl-3,4-dihydro-1H-isoquinolin-2-yl-acetamide;

N-(indan-2-yl)-N-(2-fluorobenzyl)-2-[(1R,4S)-4-methyl-1-(2-methylphenyl)-3,4-dihydroisoquinolin-2(1H)-yl]acetamide;

N-(indan-2-yl)-N-(2-fluorobenzyl)-2-[(1S,4S)-4-methyl-1-(2-methylphenyl)-3,4-dihydroisoquinolin-2(1H)-yl]acetamide;

2-{[1-(indan-2-yl)-2-phenyl-1H-imidazol-5-yl]methyl}-1-(2-methylphenyl)-1,2,3,4-tetrahydroisoquinoline;

(2S)-N-(indan-2-yl)-N-(2-fluorobenzyl)-2-[(1R)-1-(2-methylphenyl)-3,4-dihydroisoquinolin-2(1H)-yl]propanamide;

N-(indan-2-yl)-2-[1-(3,4-dimethylphenyl)-3,4-dihydroisoquinolin-2(1H)-yl]-N-(2-fluorobenzyl)acetamide;

2-[1-(2,3-dichlorophenyl)-3,4-dihydroisoquinolin-2(1H)-yl]-N-(indan-2-yl)-N-(2-fluorobenzyl)acetamide;

N-(indan-2-yl)-N-(2-fluorobenzyl)-2-[1-[4-fluoro-2-(trifluoromethyl)phenyl]-3,4-dihydroisoquinolin-2(1H)-yl]acetamide;

N-(indan-2-yl)-N-(2-fluorobenzyl)-2-[1-[5-fluoro-2-(trifluoromethyl)phenyl]-3,4-dihydroisoquinolin-2(1H)-yl]acetamide;

(2S)-N-(indan-2-yl)-N-(2-fluorobenzyl)-2-[(1S)-1-(2-methylphenyl)-3,4-dihydroisoquinolin-2(1H)-yl]propanamide;

2-[(1S)-1-(2-bromophenyl)-3,4-dihydroisoquinolin-2(1H)-yl]-N-(indan-2-yl)-N-(2-fluorobenzyl)acetamide;

N-(indan-2-yl)-N-(2-fluorobenzyl)-2-[(1S)-1-[2-(trifluoromethyl)phenyl]-3,4-dihydroisoquinolin-2(1H)-yl]acetamide;

(2S)-N-(indan-2-yl)-N-(2-fluorobenzyl)-2-[(1R)-1-(2-methylphenyl)-3,4-dihydroisoquinolin-2(1H)-yl]propanamide;

2-[1-(1,1'-biphenyl-2-yl)-3,4-dihydroisoquinolin-2(1H)-yl]-N-(indan-2-yl)-N-(2-fluorobenzyl)acetamide;

N-(indan-2-yl)-N-(2-fluorobenzyl)-2-[1-(1-naphthyl)-3,4-dihydroisoquinolin-2(1H)-yl]acetamide;

N-(indan-2-yl)-N-(2-fluorobenzyl)-2-[(1R,4R)-4-methyl-1-(2-methylphenyl)-3,4-dihydroisoquinolin-2(1H)-yl]acetamide;

2-[1-(2-chloro-3-methylphenyl)-3,4-dihydroisoquinolin-2(1H)-yl]-N-(indan-2-yl)-N-(2-fluorobenzyl)acetamide;

N-(indan-2-yl)-N-(2-fluorobenzyl)-2-[1-(3-fluoro-2-methylphenyl)-3,4-dihydroisoquinolin-2(1H)-yl]acetamide;

N-(indan-2-yl)-2-[1-(2,5-dimethylphenyl)-3,4-dihydroisoquinolin-2(1H)-yl]-N-(2-fluorobenzyl)acetamide;

N-(indan-2-yl)-N-(2-fluorobenzyl)-2-[1-[3-(trifluoromethyl)phenyl]-3,4-dihydroisoquinolin-2(1H)-yl]acetamide;

2-[1-(5-chloro-2-methylphenyl)-3,4-dihydroisoquinolin-2(1H)-yl]-N-(indan-2-yl)-N-(2-fluorobenzyl)acetamide;

2-[1-(2-chloro-5-methylphenyl)-3,4-dihydroisoquinolin-2(1H)-yl]-N-(indan-2-yl)-N-(2-fluorobenzyl)acetamide;

2-[1-(2,3-dihydro-1-benzofuran-7-yl)-3,4-dihydroisoquinolin-2(1H)-yl]-N-(indan-2-yl)-N-(2-fluorobenzyl)acetamide;

N-(indan-2-yl)-N-(2-fluorobenzyl)-2-[(1R,4R)-1-(2-fluorophenyl)-4-methyl-3,4-dihydroisoquinolin-2(1H)-yl]acetamide;

N-(indan-2-yl)-N-(2-fluorobenzyl)-2-[(3S)-3-methyl-1-(2-methylphenyl)-3,4-dihydroisoquinolin-2(1H)-yl]acetamide;

N-(indan-2-yl)-2-[1-(2,6-dimethylphenyl)-3,4-dihydroisoquinolin-2(1H)-yl]-N-(2-fluorobenzyl)acetamide;

N-(indan-2-yl)-N-(2-fluorobenzyl)-2-[1-(5-fluoro-2-methylphenyl)-3,4-dihydroisoquinolin-2(1H)-yl]acetamide;

N-(indan-2-yl)-N-(2-fluorobenzyl)-2-[(1R)-1-(2-fluorophenyl)-3,4-dihydroisoquinolin-2(1H)-yl]acetamide;

2-[(1R,4R)-1-(2-chlorophenyl)-4-methyl-3,4-dihydroisoquinolin-2(1H)-yl]-N-(indan-2-yl)-N-(2-fluorobenzyl)acetamide;

(2S)-N-(indan-2-yl)-N-(2-fluorobenzyl)-2-[(1R)-1-(2-fluorophenyl)-3,4-dihydroisoquinolin-2(1H)-yl]propanamide;

N-(indan-2-yl)-N-(2-fluorobenzyl)-2-[1-(3-fluoro-4-methylphenyl)-3,4-dihydroisoquinolin-2(1H)-yl]acetamide;

N-(indan-2-yl)-N-(2-fluorobenzyl)-2-(1-quinolin-8-yl-3,4-dihydroisoquinolin-2(1H)-yl)acetamide;

(2S)-N-(indan-2-yl)-N-(2-fluorobenzyl)-2-[(1R)-1-(1-naphthyl)-3,4-dihydroisoquinolin-2(1H)-yl]propanamide;

(2S)-2-[(1R)-1-(2-chlorophenyl)-3,4-dihydroisoquinolin-2(1H)-yl]-N-(indan-2-yl)-N-(2-fluorobenzyl)propanamide;

2-[1-(3-chloro-2-methylphenyl)-3,4-dihydroisoquinolin-2(1H)-yl]-N-(indan-2-yl)-N-(2-fluorobenzyl)acetamide;

N-(indan-2-yl)-N-(2-fluorobenzyl)-2-[1-(2-fluoro-5-methylphenyl)-3,4-dihydroisoquinolin-2(1H)-yl]acetamide;

(2S)-N-(indan-2-yl)-2-[(1R)-1-(2,3-dimethylphenyl)-3,4-dihydroisoquinolin-2(1H)-yl]-N-(2-fluorobenzyl)propanamide;

(2S)-N-(indan-2-yl)-2-[(1S)-1-(2,3-dimethylphenyl)-3,4-dihydroisoquinolin-2(1H)-yl]-N-(2-fluorobenzyl)propanamide;

(2S)-N-(indan-2-yl)-N-(2-fluorobenzyl)-2-[(1R)-1-[2-(trifluoromethyl)phenyl]-3,4-dihydroisoquinolin-2(1H)-yl]propanamide;

(2S)-2-[(1R)-1-(2-bromophenyl)-3,4-dihydroisoquinolin-2(1H)-yl]-N-(indan-2-yl)-N-(2-fluorobenzyl)propanamide;

(2S)-N-(indan-2-yl)-2-[(1R)-1-(2,6-dimethylphenyl)-3,4-dihydroisoquinolin-2(1H)-yl]-N-(2-fluorobenzyl)propanamide;

N-(indan-2-yl)-2-[6,7-dimethyl-1-(2-methylphenyl)-3,4-dihydroisoquinolin-2(1H)-yl]-N-(2-fluorobenzyl)acetamide;

N-(indan-2-yl)-2-[7,8-dimethyl-1-(2-methylphenyl)-3,4-dihydroisoquinolin-2(1H)-yl]-N-(2-fluorobenzyl)acetamide;

2-[1-(2,3-difluorophenyl)-3,4-dihydroisoquinolin-2(1H)-yl]-N-(indan-2-yl)-N-(2-fluorobenzyl)acetamide;

(2S)-2-[(1R)-1-(2,3-dihydro-1-benzofuran-7-yl)-3,4-dihydroisoquinolin-2(1H)-yl]-N-(indan-2-yl)-N-(2-fluorobenzyl)propanamide;

methyl 4-(2-{2-[indan-2-yl(2-fluorobenzyl)amino]-2-oxoethyl}-1,2,3,4-tetrahydroisoquinolin-1-yl)benzoate;

(2S)-N-benzyl-2-[(1R)-1-(2-bromophenyl)-3,4-dihydroisoquinolin-2(1H)-yl]-N-(2-chloro-4-hydroxybenzyl)propanamide;

N-(indan-2-yl)-N-(2-fluorobenzyl)-2-[8-methyl-1-(2-methylphenyl)-3,4-dihydroisoquinolin-2(1H)-yl]acetamide;

N-(indan-2-yl)-N-(3-methoxybenzyl)-2-[1-(2-methylphenyl)-3,4-dihydroisoquinolin-2(1H)-yl]acetamide;

N-(indan-2-yl)-N-(2-fluorobenzyl)-2-(1-mesityl-3,4-dihydroisoquinolin-2(1H)-yl)acetamide;

2-[1-(2,6-difluorophenyl)-3,4-dihydroisoquinolin-2(1H)-yl]-N-(indan-2-yl)-N-(2-fluorobenzyl)acetamide;

N-(2-fluorobenzyl)-2-[1-(2-methylphenyl)-3,4-dihydroisoquinolin-2(1H)-yl]-N-phenylacetamide;

N-(indan-2-yl)-N-(2-fluorobenzyl)-2-[1-(2-methyl-1-naphthyl)-3,4-dihydroisoquinolin-2(1H)-yl]acetamide;

(2S)-2-[(1R)-1-(2-chloro-5-methylphenyl)-3,4-dihydroisoquinolin-2(1H)-yl]-N-(indan-2-yl)-N-(2-fluorobenzyl)propanamide;

(2S)-N-(indan-2-yl)-2-[(1S)-1-(2,5-dimethylphenyl)-3,4-dihydroisoquinolin-2(1H)-yl]-N-(2-fluorobenzyl)propanamide;

(2S)-N-(indan-2-yl)-N-(2-fluorobenzyl)-2-[(1R)-1-(2-fluoro-5-methylphenyl)-3,4-dihydroisoquinolin-2(1H)-yl]propanamide;

(2S)-2-[(1R)-1-(2-chlorophenyl)-3,4-dihydroisoquinolin-2(1H)-yl]-N,N-bis(2-fluorobenzyl)propanamide;

4-[(indan-2-yl{[1-(2-methylphenyl)-3,4-dihydroisoquinolin-2(1H)-yl]acetyl}amino)methyl]benzoic acid;

(2S)-2-[(1R)-1-(2,6-difluorophenyl)-3,4-dihydroisoquinolin-2(1H)-yl]-N-(indan-2-yl)-N-(2-fluorobenzyl)propanamide;

(2S)-2-[(1R)-1-(2-chlorophenyl)-3,4-dihydroisoquinolin-2(1H)-yl]-N-(indan-2-yl)-N-(2-hydroxybenzyl)propanamide;

(2S)-2-[(1R)-1-(2-chlorophenyl)-3,4-dihydroisoquinolin-2(1H)-yl]-N-(2-fluorobenzyl)-N-(2-phenylethyl)propanamide;

N-(indan-2-yl)-N-(3-hydroxybenzyl)-2-[1-(2-methylphenyl)-3,4-dihydroisoquinolin-2(1H)-yl]acetamide;

2-[1-(2-chlorophenyl)-3,4-dihydroisoquinolin-2(1H)-yl]-N-(2-fluorobenzyl)-N-(5-methoxy-indan-2-yl)acetamide;

N-(2-fluorobenzyl)-N-(5-methoxy-indan-2-yl)-2-[1-[2-(trifluoromethyl)phenyl]-3,4-dihydroisoquinolin-2(1H)-yl]acetamide;

2-[1-(2,6-dichlorophenyl)-3,4-dihydroisoquinolin-2(1H)-yl]-N-(indan-2-yl)-N-(2-fluorobenzyl)acetamide;

2-[1-(2-chloro-6-fluorophenyl)-3,4-dihydroisoquinolin-2(1H)-yl]-N-(indan-2-yl)-N-(2-fluorobenzyl)acetamide;

(2S)-2-[(1R)-1-(2-chlorophenyl)-3,4-dihydroisoquinolin-2(1H)-yl]-N-(indan-2-yl)-N-(1H-imidazol-4-ylmethyl)propanamide;

3-{[{(2S)-2-[(1R)-1-(2-chlorophenyl)-3,4-dihydroisoquinolin-2(1H)-yl]propanoyl}(indan-2-yl)amino]methyl}benzoic acid;

N-(indan-2-yl)-N-(2-fluorobenzyl)-2-[1-[2-fluoro-6-(trifluoromethyl)phenyl]-3,4-dihydroisoquinolin-2(1H)-yl]acetamide;

N-(indan-2-yl)-N-(2-fluorobenzyl)-2-[8-fluoro-1-(2-methylphenyl)-3,4-dihydroisoquinolin-2(1H)-yl]acetamide;

N-(indan-2-yl)-N-(2-fluoro-5-hydroxybenzyl)-2-[1-(2-methylphenyl)-3,4-dihydroisoquinolin-2(1H)-yl]acetamide;

(2S)-2-[(1R)-1-(2,6-dichlorophenyl)-3,4-dihydroisoquinolin-2(1H)-yl]-N-(indan-2-yl)-N-(2-fluorobenzyl)propanamide;

(2S)-2-[(1R)-1-(2-chloro-6-fluorophenyl)-3,4-dihydroisoquinolin-2(1H)-yl]-N-(indan-2-yl)-N-(2-fluorobenzyl)propanamide;

(2S)-2-[(1R)-1-(2-chlorophenyl)-3,4-dihydroisoquinolin-2(1H)-yl]-N-[2-(2-fluorophenyl)ethyl]-N-(4-hydroxybenzyl)propanamide;

3-{[{(2S)-2-[(1R)-1-(2-chlorophenyl)-3,4-dihydroisoquinolin-2(1H)-yl]propanoyl}(indan-2-yl)amino]methyl}-N,N-dimethylbenzamide;

(2S)-2-[(1R)-1-(2-chlorophenyl)-3,4-dihydroisoquinolin-2(1H)-yl]-N-(indan-2-yl)-N-(4-hydroxy-3,5-dimethylbenzyl)propanamide;

(2S)-2-[(1R)-1-(2-chlorophenyl)-3,4-dihydroisoquinolin-2(1H)-yl]-N-(indan-2-yl)-N-(2-flurorobenzyl)propanamide;

(2S)-2-[(1R)-1-(2-chlorophenyl)-3,4-dihydroisoquinolin-2(1H)-yl]-N-[2-(2-fluorophenyl)ethyl]-N-(2-phenylethyl)propanamide;

(2S)-2-[(1R)-1-(2-chlorophenyl)-3,4-dihydroisoquinolin-2(1H)-yl]-N-(2-fluorobenzyl)-N-[2-(2-fluorophenyl)ethyl]propanamide;

(2S)-2-[(1R)-1-(2,6-dichlorophenyl)-3,4-dihydroisoquinolin-2(1H)-yl]-N-(indan-2-yl)-N-(4-hydroxy-3,5-dimethylbenzyl)propanamide;

(2S)-2-[(1R)-1-(2-chlorophenyl)-3,4-dihydroisoquinolin-2(1H)-yl]-N-(3-cyanobenzyl)-N-(indan-2-yl)propanamide;

(2S)-2-[(1R)-1-(2-chlorophenyl)-3,4-dihydroisoquinolin-2(1H)-yl]-N-(indan-2-yl)-N-(3-nitrobenzyl)propanamide;

N-(indan-2-yl)-N-(3-hydroxybenzyl)-2-[(1S)-1-(2-methylphenyl)-3,4-dihydroisoquinolin-2(1H)-yl]acetamide;

(2S)-2-[(1R)-1-(2-chlorophenyl)-3,4-dihydroisoquinolin-2(1H)-yl]-N-(indan-2-yl)-N-(3-hydroxybenzyl)propanamide;

(2S)-2-[(1R)-1-(2-chlorophenyl)-3,4-dihydroisoquinolin-2(1H)-yl]-N-(indan-2-yl)-N-(2-fluoro-3-hydroxybenzyl)propanamide;

2-[8-chloro-1-(2-methylphenyl)-3,4-dihydroisoquinolin-2(1H)-yl]-N-(indan-2-yl)-N-(2-fluorobenzyl)acetamide;

2-[8-chloro-1-(2-chloro-6-fluorophenyl)-3,4-dihydroisoquinolin-2(1H)-yl]-N-(indan-2-yl)-N-(2-fluorobenzyl)acetamide;

(2S)-N-(2-fluorobenzyl)-N-[2-(4-hydroxyphenyl)ethyl]-2-[(1R)-1-(1-naphthyl)-3,4-dihydroisoquinolin-2(1H)-yl]propanamide;

(2S)-N-(2-fluorobenzyl)-N-[(2-(1H-indol-3-yl)ethyl]-2-[(1R)-1-(1-naphthyl)-3,4-dihydroisoquinolin-2(1H)-yl]propanamide;

(2S)-2-[(1R)-1-(2-chlorophenyl)-3,4-dihydroisoquinolin-2(1H)-yl]-N-[3-(difluoromethoxy)-2-fluorobenzyl]-N-(indan-2-yl)propanamide;

(2S)-N-(indan-2-yl)-N-[(2-methoxypyridin-3-yl)methyl]-2[(1R)-1-(1-naphthyl)-3,4-dihydroisoquinolin-2(1H)-yl]propanamide;

(2S)-N-(2-fluorobenzyl)-N-[(2-methoxypyridin-3-yl)methyl]-2[(1R)-1-(1-naphthyl)-3,4-dihydroisoquinolin-2(1H)-yl]propanamide;

N-(indan-2-yl)-N-(2-fluorobenzyl)-2-[1-(4-hydroxyphenyl)-3,4-dihydroisoquinolin-2(1H)-yl]acetamide;

(2S)-N-(indan-2-yl)-N-[(6-methoxypyridin-2-yl)methyl]-2[(1R)-1-(1-naphthyl)-3,4-dihydroisoquinolin-2(1H)-yl]propanamide;

(2S)-N-(2-fluorobenzyl)-N-[(6-methoxypyridin-2-yl)methyl]-2-[(1R)-1-(1-naphthyl)-3,4-dihydroisoquinolin-2(1H)-yl]propanamide;

(2S)-N-(indan-2-yl)-N-[(3-fluoropyridin-2-yl)methyl]-2-[(1R)-1-(1-naphthyl)-3,4-dihydroisoquinolin-2(1H)-yl]propanamide;

(2S)-N-(indan-2-yl)-N-[(5-methoxypyridin-3-yl)methyl]-2[(1R)-1-(1-naphthyl)-3,4-dihydroisoquinolin-2(1H)-yl]propanamide; or a pharmaceutically acceptable salt thereof.

16. A compound or pharmaceutically acceptable salt according to claim 1 which is

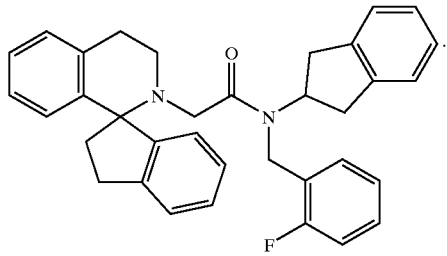

17. A pharmaceutical composition comprising at least one compound or salt according to claim 1, or a prodrug or hydrate thereof, in combination with a physiologically acceptable carrier or excipient.

18. A method for inhibiting signal-transducing activity of a cellular C5a receptor, comprising contacting a cell expressing a C5a receptor with at least one compound or salt according to claim 1, and thereby reducing signal transduction by the C5a receptor.

19. A method for treating a patient suffering from rheumatoid arthritis, psoriasis, cardiovascular disease, reperfusion injury, or bronchial asthma comprising administering to the patient a C5a receptor modulatory amount of a compound according to claim 1.

20. A method for treating a patient suffering from stroke, myocardial infarction, atherosclerosis, ischemic heart disease, or ischemia-reperfusion injury comprising administering to the patient a C5a receptor modulatory amount of a compound according to claim 1.

* * * * *